United States Patent
Lewis et al.

(10) Patent No.: US 8,309,554 B2
(45) Date of Patent: Nov. 13, 2012

(54) HYPOXIA ACTIVATED DRUGS OF NITROGEN MUSTARD ALKYLATORS

(75) Inventors: Jason Lewis, Castro Valley, CA (US); Mark Matteucci, Portola Valley, CA (US); Tao Chen, Palo Alto, CA (US); Hailong Jiao, Foster City, CA (US)

(73) Assignee: Threshold Pharmaceuticals, South San Francisco, CA (US)

( * ) Notice: Subject to any disclaimer, the term of this patent is extended or adjusted under 35 U.S.C. 154(b) by 0 days.

(21) Appl. No.: 12/992,261

(22) PCT Filed: May 14, 2009

(86) PCT No.: PCT/US2009/044038
§ 371 (c)(1),
(2), (4) Date: Mar. 28, 2011

(87) PCT Pub. No.: WO2009/140553
PCT Pub. Date: Nov. 19, 2009

(65) Prior Publication Data
US 2011/0190310 A1 Aug. 4, 2011

Related U.S. Application Data

(60) Provisional application No. 61/053,324, filed on May 15, 2008.

(51) Int. Cl.
*A61K 31/496* (2006.01)
*A61K 31/437* (2006.01)
*A61K 31/4436* (2006.01)
*A61K 31/4192* (2006.01)
*A61K 31/4178* (2006.01)
*A61K 31/4168* (2006.01)
*A61K 31/381* (2006.01)
*C07D 409/02* (2006.01)
*C07D 471/02* (2006.01)
*C07D 409/06* (2006.01)
*C07D 233/54* (2006.01)
*C07D 333/42* (2006.01)

(52) U.S. Cl. ............ 514/252.13; 514/300; 514/336; 514/359; 514/397; 514/398; 514/447; 544/379; 546/121; 546/280.4; 548/260; 548/315.1; 548/332.5; 549/68

(58) Field of Classification Search ............ 514/252.13, 514/398, 447, 336, 397, 300, 359; 548/332.5, 548/315.1, 260; 549/68; 546/280.4, 121; 544/379
See application file for complete search history.

(56) References Cited

U.S. PATENT DOCUMENTS
2007/0032455 A1 2/2007 Denny et al.

FOREIGN PATENT DOCUMENTS
WO WO 94-27954 A1 12/1994

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Seow H.A., et al., "1,2-Bis(methylsulfonyl)-I-(2-chloroethyl)-2[[I-(4-nitrophenyl)ethoxy] carbonyl]hydrazine: an anticancer agent targeting hypoxic cells." Proc. Natl. Acad. Sci. USA., Jun. 28, 2005; 102(26): 9282-9287.
Tercel M, et al., "Hypoxia-selective antitumor agents. 12. Nitrobenzyl quaternary salts as bioreductive prodrugs of the alkylating agent mechlorethamine." J. Med. Chern., Mar. 1, 1996; 39(5): 1084-1094.
Fourie J, et al., "Structure-activity study with bioreductive benzoquinone alkylating agents: effects on DT-diaphorase-mediated DNA crosslink and strand break formation in relation to mechanisms of cytotoxicity." Cancer Chemother. Pharmacol., Mar. 2004; 53(3): 191-203. Epub Nov. 12, 2003.
International search report issued on Jan. 12, 2010 for PCT/US2009/044038.

* cited by examiner

*Primary Examiner* — Kristin Bianchi
(74) *Attorney, Agent, or Firm* — Foley & Lardner LLP; Antoinette F. Konski; Photon Rao

(57) ABSTRACT

Hypoxia activated drug compounds having a structure of formula (I) are useful in the treatment of cancer and other hyperproliferative diseases.

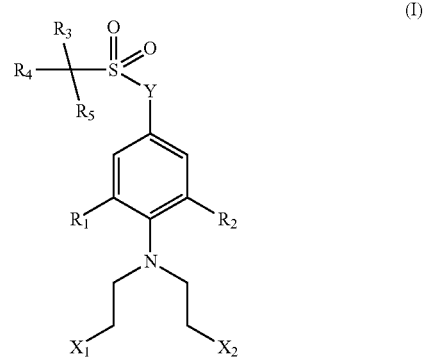

17 Claims, No Drawings

HYPOXIA ACTIVATED DRUGS OF NITROGEN MUSTARD ALKYLATORS

CROSS-REFERENCE TO RELATED APPLICATIONS

This application is a national stage application under 35 U.S.C. §371 of International Application No. PCT/US2009/044038, filed May 14, 2009, which in turn claims priority to U.S. Provisional Patent Application Ser. No. 61/053,324 filed on May 15, 2008, the contents of each of which are incorporated herein by reference in their entirety.

BACKGROUND OF THE INVENTION

1. Field of the Invention

This invention provides compositions and methods for the treatment of cancer, and generally relates to the fields of medicinal chemistry, medicine, pharmacology, molecular biology, and biology.

2. Description of Related Art

Hypoxia activated and bioreducible drugs of antineoplastic agents are useful for treating solid tumor cancers. Such hypoxia activated drugs contain a bioreductive group, an optional linker, and an antineoplastic agent, and are less cytotoxic than the corresponding antineoplastic agents without the bioreductive group attached thereto. Under hypoxic conditions or hypoxia, the bioreductive group present in the drug is reduced, and a cytotoxic antineoplastic agent is generated and/or released. Under normoxic conditions, or normoxia, such as those existing in a normal cell, a hypoxia activated drug is typically non-toxic or at least much less toxic than under hypoxic conditions, or hypoxia. Due to insufficient vascularization of the solid tumor, certain tumor cells will exist in a hypoxic state. The cytotoxic antineoplastic agents generated and/or released from a hypoxia activated drug in the hypoxic zone of the solid tumor can selectively kill cancer cells in and around that zone.

Aryl nitrogen mustards are a class of antineoplastic agents useful in the treatment of leukemias and solid tumors. Certain aryl nitrogen mustards, such as, for example, chlorambucil and melphalan, contain a substituted phenyl moiety attached to an N,N-bis-(2-chloroethyl)amino moiety.

Heretofore, the attachment of a bioreductive group optionally though a suitable linker to these aryl nitrogen mustards to provide effective anti-tumor agents was unknown.

There remains a need for additional hypoxia activated and similar bioreducible drugs for the treatment of cancer, including those containing aryl nitrogen mustards and related antineoplastic agents. The present invention meets such needs as summarized below.

BRIEF SUMMARY OF THE INVENTION

This invention is directed, in part, to the surprising discovery that certain compounds comprising an N,N-bis-(2-halo or 2-sulfonate-ethyl)aminoaryl antineoplastic agent, an optionally substituted methylene-$SO_2$—O—/methylene-$SO_2$—$NR_6$— linker, wherein $R_6$ is hydrogen or an optionally substituted alkyl moiety, and a nitroheteroaryl bioreductive group provide for effective hypoxia activated drugs when combined in the manner described below.

In one embodiment, the N,N-bis-(2-halo or 2-sulfonate-ethyl)aminoaryl group is N,N-bis-(2-chloroethyl)aminophenyl optionally substituted at the 2 and/or 6 positions with $R_1$ and $R_2$ as defined below.

In another embodiment, a methylene-$SO_2$—O—/methylene-$SO_2$—$NR_6$ linker is attached to the optionally substituted phenyl ring of the optionally substituted N,N-bis-(2-haloethyl)aminophenyl group, preferably at the para position relative to the bis-(2-haloethyl)amino substituent. The methylene-$SO_2$—O— linker is represented by the group —$CR_3R_4SO_2$—O— where the terminal oxygen is attached to the optionally substituted phenyl ring with $R_3$ and $R_4$ as defined below. The methylene-$SO_2$—$NR_6$ linker is represented by the group —$CR_3R_4SO_2$—$NR_6$— where $R_6$ is defined below and the terminal nitrogen is attached to the optionally substituted phenyl ring.

The nitroheteroaryl bioreductive group is selected from any of those well known groups as defined in detail below.

Accordingly, in one embodiment, there is provided a compound comprising an optionally substituted N,N-bis-(2-halo or 2-sulfonate-ethyl)aminoaryl antineoplastic agent, an optionally substituted methylene-$SO_2$—O—/methylene-$SO_2NR_6$— linker, and a bioreductive group, or a pharmaceutically acceptable salt thereof wherein said compound exhibits higher cytotoxicity under hypoxia than under normoxia. In an aspect of this embodiment, the bioreductive group is a nitroheteroaryl bioreductive group which is also characterized below.

In one of its compound aspects, this invention is directed to compounds of Formula I or pharmaceutically acceptable salts thereof:

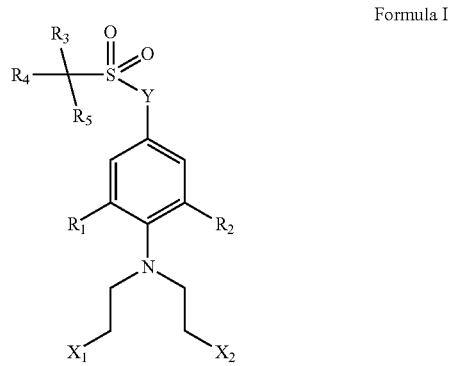

Formula I wherein each of $X_1$ and $X_2$ is independently selected from the group consisting of chloro, bromo, iodo, and sulfonate; Y is selected from the group consisting of O and $NR_6$; each of $R_1$ and $R_2$ is independently selected from the group consisting of hydrogen, halogen, and optionally substituted $C_{1-6}$alkyl; each of $R_3$ and $R_4$ is independently selected from the group consisting of hydrogen and optionally substituted $C_{1-6}$alkyl; $R_5$ is a bioreductive group selected from the group consisting of:

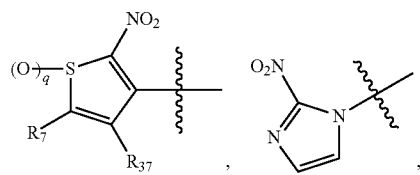

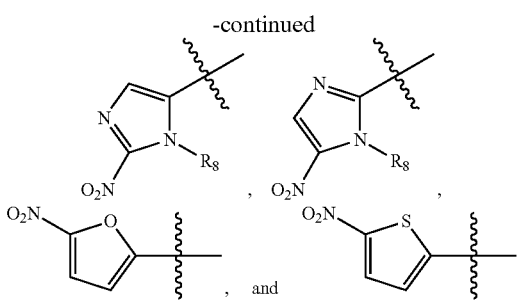

R$_6$ is selected from the group consisting of hydrogen and optionally substituted C$_{1-6}$ alkyl; R$_7$ is selected from the group consisting of hydrogen and optionally substituted C$_{1-6}$ alkyl; R$_{37}$ is hydrogen, or together with R$_7$ and the carbon atoms to which they are bonded, form an optionally substituted cycloalkyl, optionally substituted heterocyclyl, optionally substituted aryl, or optionally substituted heteroaryl moiety; R$_8$ is optionally substituted C$_{1-6}$ alkyl; and q is 0, 1, or 2.

In one of its composition aspects, this invention is directed to a pharmaceutical composition comprising a compound of Formula I or a pharmaceutically acceptable salt thereof and a pharmaceutically acceptable carrier, excipient, or diluent. In another of its composition aspects, the pharmaceutical composition comprises a therapeutically effective amount of the compound of Formula I or a pharmaceutically acceptable salt thereof.

In one of its method aspects, this invention is directed to a method of treating cancer and other hyperproliferative diseases comprising administering a therapeutically effective amount of the compound of Formula I to a patient in need of such treatment.

In still another of its method aspects, the above method of treating cancer and other hyperproliferaive diseases further comprises administering another anticancer agent or anticancer therapy in combination with a compound of Formula I to a patient in need of such treatment.

These and other aspects and embodiments of the present invention are described by the detailed description.

DETAILED DESCRIPTION OF THE INVENTION

I. Definitions

It is to be understood that the terminology used herein is for the purpose of describing particular embodiments and/or aspects only and is not intended to limit the scope of this invention. In this specification and in the claims that follow, reference will be made to a number of terms that shall be defined to have the following meanings:

"About" refers to ±20% of a quantity and in some embodiments may be ±15%, ±10%, and ±5%.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Alkyl" refers to monovalent saturated aliphatic hydrocarbyl groups having from 1 to 10 carbon atoms and, in some embodiments, from 1 to 6 carbon atoms. "C$_{x-y}$alkyl" refers to alkyl groups having from x to y carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

"Substituted alkyl" refers to an alkyl group having from 1 to 5 and, in some embodiments, 1 to 3 or 1 to 2 substituents selected from the group consisting of alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, spirocycloalkyl, SO$_3$H, substituted sulfonyl, sulfonyloxy, thioacyl, thiocyanate, thiol, alkylthio, and substituted alkylthio, wherein said substituents are as defined herein.

"Alkylidene" or "alkylene" refers to divalent saturated aliphatic hydrocarbyl groups having from 1 to 10 carbon atoms and, in some embodiments, from 1 to 6 carbon atoms. "C$_{u-v}$ alkylene" refers to alkylene groups having from u to v carbon atoms. The alkylidene and alkylene groups include branched and straight chain hydrocarbyl groups. For example, "C$_{1-6}$alkylene" is meant to include methylene, ethylene, propylene, 2-methypropylene, pentylene, and the like.

"Substituted alkylidene" or "substituted alkylene" refers to an alkylidene group having from 1 to 5 and, in some embodiments, 1 to 3 or 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, oxo, thione, spirocycloalkyl, SO$_3$H, substituted sulfonyl, sulfonyloxy, thioacyl, thiocyanate, thiol, alkylthio, and substituted alkylthio, wherein said substituents are as defined herein.

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, C$_{x-y}$alkenyl refers to alkenyl groups having from x to y carbon atoms and is meant to include for example, ethenyl, propenyl, 1,3-butadienyl, and the like.

"Substituted alkenyl" refers to alkenyl groups having from 1 to 3 substituents and, in some embodiments, 1 to 2 substituents selected from the group consisting of alkoxy, substituted alkoxy, acyl, acylamino, acyloxy, alkyl, substituted alkyl, alkynyl, substituted alkynyl, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, $C_{2-6}$alkynyl is meant to include ethynyl, propynyl, and the like.

"Substituted alkynyl" refers to alkynyl groups having from 1 to 3 substituents and, in some embodiments, from 1 to 2 substituents selected from the group consisting of alkoxy, substituted alkoxy, acyl, acylamino, acyloxy, alkyl, substituted alkyl, alkenyl, substituted alkenyl, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are as defined herein and with the proviso that any hydroxy or thiol substitution is not attached to an acetylenic carbon atom.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl), wherein substituted alkyl is as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, substituted hydrazino-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, substituted hydrazino, heteroaryl, substituted heteroaryl, heterocyclic, and substituted heterocyclic are as defined herein. Acyl includes the "acetyl" group $CH_3C(O)$—.

"Acylamino" refers to the groups —NR$^{20}$C(O)alkyl, —NR$^{20}$C(O)substituted alkyl, —NR$^{20}$C(O)cycloalkyl, —NR$^{20}$C(O)substituted cycloalkyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, C(O)heteroaryl, —NR$^{20}$C(O)substituted heteroaryl, —NR$^{20}$C(O)heterocyclic, and —NR$^{20}$C(O)substituted heterocyclic wherein R$^{20}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NR$^{21}$R$^{22}$ where R$^{21}$ and R$^{22}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R$^{21}$ and R$^{22}$ are optionally joined together with the nitrogen bound thereto to form a heterocyclic or substituted heterocyclic group, provided that R$^{21}$ and R$^{22}$ are both not hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein. When R$^{21}$ is hydrogen and R$^{22}$ is alkyl, the substituted amino group is sometimes referred to herein as alkylamino. When R$^{21}$ and R$^{22}$ are alkyl, the substituted amino group is sometimes referred to herein as dialkylamino. When referring to a monosubstituted amino, it is meant that either R$^{21}$ or R$^{22}$ is hydrogen but not both. When referring to a disubstituted amino, it is meant that neither R$^{21}$ nor R$^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —C(O)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, hydroxy, alkoxy, substituted alkoxy, amino, substituted amino, and acylamino, and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminothiocarbonyl" refers to the group —C(S)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminocarbonylamino" refers to the group —NR$^{20}$C(O)NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminothiocarbonylamino" refers to the group —NR$^{20}$C(S)NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminocarbonyloxy" refers to the group —O—C(O)NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminosulfonyl" refers to the group —SO$_2$NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminosulfonyloxy" refers to the group —O—SO$_2$NR$^{23}$R$^{24}$ where R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aminosulfonylamino" refers to the group —NR$^{20}$—SO$_2$NR$^{23}$R$^{24}$ where R$^{20}$ is hydrogen or alkyl and R$^{23}$ and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amidino" refers to the group —C(=NR$^{25}$)NR$^{23}$R$^{24}$ where R$^{25}$, R$^{23}$, and R$^{24}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and where R$^{23}$ and R$^{24}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aryl" or "Ar" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"Substituted aryl" refers to aryl groups which are substituted with 1 to 8 and, in some embodiments, 1 to 5, 1 to 3, or 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, sulfonyloxy, thioacyl, thiocyanate, thiol, alkylthio, and substituted alkylthio, wherein said substituents are defined herein.

"Aryloxy" refers to the group —O-aryl, where aryl is as defined herein, that includes, by way of example, phenoxy and naphthyloxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Azido" refers to the group —N₃.

"Bioreductive group" refers to an optionally substituted nitroaryl, nitroheteroaryl, indoloquinonyl, naphthoquinonyl, aryl- or heteroaryl-amine oxide, or a disulfide containing moiety, which can undergo in vivo and/or in vitro reduction under hypoxic conditions. Bioreductive groups are described for example in the U.S. Pat. Nos. 5,750,782; 5,780,585; 5,872,129; 6,251,933; 5,306,727; 5,403,932; 5,190,929; and 6,656,926; PCT Pat. Appl. Pub. Nos. WO 00/64864; WO 04/85361; WO 04/85421; WO 04/87075; 06/57946; and WO 07/002,931; US Pat. Appl. Pub. Nos. 2003/0008850; 2004/254103; and 2005/043244, and the references deGroot et al., 2001, Current Med. Chem. 8:1093-22; Borch et al., J. Med. Chem. 2000, 43: 2258-65; Borch et al., J. Med. Chem. 2001, 44: 69-73; Borch et al., J. Med. Chem. 2001, 44: 74-7; Hernick et al. J. Med. Chem. 2002, 45: 3540-48; Herrick et al., J. Med. Chem. 2003, 46: 148-54; Papot et al., Curr. Med. Chem., 2002, 2, 155-85; Tercel et al., J. Med. Chem. 1996, 39: 1084-94; and Tercel et al., J. Med. Chem. 2001, 44: 3511-22, each of which is incorporated herein by reference in its entirety.

"Cancer" or "solid tumors" refer to lymphomas and malignant tumors of potentially unlimited growth that can expand locally by invasion and systemically by metastasis. Examples of cancers include, but are not limited to cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor.

"Cyano" or "carbonitrile" refers to the group —CN.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)β-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR²⁰—C(O)O-alkyl, —NR²⁰—C(O)O-substituted alkyl, —NR²⁰—C(O)O-alkenyl, —NR²⁰—C(O)O-substituted alkenyl, —NR²⁰—C(O)O-alkynyl, —NR²⁰—C(O)O-substituted alkynyl, —NR²⁰—C(O)O-aryl, —NR²⁰—C(O)O-substituted aryl, —NR²⁰—C(O)β-cycloalkyl, —NR²⁰—C(O)O-substituted cycloalkyl, —NR²⁰—C(O)O-heteroaryl, —NR²⁰—C(O)O-substituted heteroaryl, —NR²⁰—C(O)O-heterocyclic, and —NR²⁰—C(O)O-substituted heterocyclic wherein R²⁰ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)β-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Compound" and "compounds" as used herein refer to a compound encompassed by the generic formulae disclosed herein, any subgenus of those generic formulae, and any forms of the compounds within the generic and subgeneric formulae, including the racemates, stereoisomers, and tautomers of the compound or compounds. In other words, "compound" and "compounds" as used herein refer to hypoxia activated drug compound(s) (or the nitrogen mustard alkylator drug(s) of the invention) of the present invention as disclosed herein.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl.

"$C_{u-v}$cycloalkyl" refers to cycloalkyl groups having u to v carbon atoms.

"Cycloalkenyl" refers to a partially saturated cycloalkyl ring having at least one site of >C=C< ring unsaturation.

"Cycloalkylene" refer to divalent cycloalkyl groups as defined herein. Examples of cycloalkylene groups include those having three to six carbon ring atoms such as cyclopropylene, cyclobutylene, cyclopentylene, and cyclohexylene.

"Substituted cycloalkyl" refers to a cycloalkyl group, as defined herein, having from 1 to 8, or 1 to 5, or in some embodiments 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are as defined herein. The term "substituted cycloalkyl" includes substituted cycloalkenyl groups.

"Cycloalkyloxy" refers to —O-cycloalkyl wherein cycloalkyl is as defined herein.

"Substituted cycloalkyloxy refers to —O-(substituted cycloalkyl) wherein substituted cycloalkyl is as defined herein.

"Cycloalkylthio" refers to —S-cycloalkyl wherein cycloalkyl is as defined herein.

"Substituted cycloalkylthio" refers to —S-(substituted cycloalkyl).

"Guanidino" or guanidine refers to the group —NHC(=NH)NH$_2$.

"Substituted guanidino" refers to —NR$^{29}$C(=NR$^{29}$)N(R$^{29}$)$_2$ where each R$^{29}$ is independently selected from the group consisting of hydrogen, alkyl, substituted alkyl, aryl, substituted aryl, heteroaryl, substituted heteroaryl, heterocyclyl, and substituted heterocyclyl and two R$^{29}$ groups attached to a common guanidino nitrogen atom are optionally joined together with the nitrogen bound thereto to form a heterocyclic or substituted heterocyclic group, provided that at least one R$^{29}$ is not hydrogen, and wherein said substituents are as defined herein.

"Halo" or "halogen" refers to fluoro, chloro, bromo, and iodo.

"Haloalkyl" refers to substitution of alkyl groups with 1 to 5 or in some embodiments 1 to 3 halo groups.

"Haloalkoxy" refers to substitution of alkoxy groups with 1 to 5 or in some embodiments 1 to 3 halo groups.

"Hydroxy" or "hydroxyl" refers to the group —OH.

"Heteroaryl" refers to an aromatic group of from 1 to 14 carbon atoms and 1 to 6 heteroatoms selected from the group consisting of oxygen, nitrogen, and sulfur and includes single ring (e.g. imidazolyl-2-yl and imidazol5-yl) and multiple ring systems (e.g. imidazopyridyl, benzotriazolyl, benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. The term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, imidazopyridyl, quinazolinonyl, benzimidazolyl, benzisoxazolyl, or benzothienyl.

"Substituted heteroaryl" refers to heteroaryl groups that are substituted with from 1 to 8 or in some embodiments 1 to 5, or 1 to 3, or 1 to 2 substituents selected from the group consisting of the substituents defined for substituted aryl.

"Heteroaryloxy" refers to —O-heteroaryl wherein heteroaryl is as defined herein.

"Substituted heteroaryloxy" refers to the group —O-(substituted heteroaryl) wherein substituted heteroaryl is as defined herein.

"Heteroarylthio" refers to the group —S-heteroaryl wherein heteroaryl is as defined herein.

"Substituted heteroarylthio" refers to the group —S-(substituted heteroaryl) wherein substituted heteroaryl is as defined herein.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from the group consisting of nitrogen, sulfur, or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In some embodiments, the nitrogen and/or sulfur atom(s) of the heterocyclic group are optionally oxidized to provide for the N-oxide, sulfinyl, sulfonyl moieties. Heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl. A prefix indicating the number of carbon atoms (e.g., $C_{3-10}$) refers to the total number of carbon atoms in the portion of the heterocyclyl group exclusive of the number of heteroatoms.

"Substituted heterocyclic" or "substituted heterocycle" or "substituted heterocycloalkyl" or "substituted heterocyclyl" refers to heterocyclic groups, as defined herein, that are substituted with from 1 to 5 or in some embodiments 1 to 3 of the substituents as defined for substituted cycloalkyl.

"Heterocyclyloxy" refers to the group —O-heterocycyl wherein heterocyclyl is as defined herein.

"Substituted heterocyclyloxy" refers to the group —O-(substituted heterocycyl) wherein substituted heterocyclyl is as defined herein.

"Heterocyclylthio" refers to the group —S-heterocycyl wherein heterocyclyl is as defined herein.

"Substituted heterocyclylthio" refers to the group —S-(substituted heterocycyl) wherein substituted heterocyclyl is as defined herein.

"Hydrazino" refers to the group —NHNH$_2$.

"Substituted hydrazino" refers to the group —NR$^{26}$NR$^{27}$R$^{28}$ where R$^{26}$, R$^{27}$, and R$^{28}$ are independently selected from the group consisting of hydrogen, alkyl, substituted alkyl, alkenyl, substituted alkenyl, alkynyl, substituted alkynyl, aryl, substituted aryl, carboxyl ester, cycloalkyl, substituted cycloalkyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R$^{27}$ and R$^{28}$ are optionally joined, together with the nitrogen bound thereto to form a heterocyclic or substituted heterocyclic group, provided that R$^{27}$ and R$^{28}$ are both not hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Hyperproliferative disease" refers to a disease characterized by cellular hyperproliferation (e.g., an abnormally increased rate or amount of cellular proliferation). Examples of hyperproliferative diseases other than cancer include, but are not limited to, allergic angiitis and granulomatosis (Churg-Strauss disease), asbestosis, asthma, atrophic gastritis, benign prostatic hyperplasia, bullous pemphigoid, coeliac disease, chronic bronchitis and chronic obstructive airway disease, chronic sinusitis, Crohn's disease, demyelinating neuropathies, dermatomyositis, eczema including atopic dermatitis, eustachean tube diseases, giant cell arteritis, graft rejection, hypersensitivity pneumonitis, hypersensitivity vasculitis (Henoch-Schonlein purpura), irritant dermatitis, inflammatory hemolytic anemia, inflammatory neutropenia, inflammatory bowel disease, Kawasaki's disease, multiple sclerosis, myocarditis, myositis, nasal polyps, nasolacrimal duct diseases, neoplastic vasculitis, pancreatitis, pemphigus vulgaris, primary glomerulonephritis, psoriasis, periodontal disease, polycystic kidney disease, polyarteritis nodosa, polyangitis overlap syndrome, primary sclerosing cholangitis, rheumatoid arthritis, serum sickness, surgical adhesions, stenosis or restenosis, scleritis, scleroderma, strictures of bile ducts, strictures (of duodenum, small bowel, and colon), silicosis and other forms of pneumoconiosis, type I diabetes, ulcerative colitis, ulcerative proctitis, vasculitis associated with connective tissue disorders, vasculitis associated with congenital deficiencies of the complement system, vasculitis of the central nervous system, and Wegener's granulomatosis.

"Leaving group" refers to a moiety that can be replaced by a nucleophile. Examples of leaving groups include but are not limited to halo and sulfonate.

"Nitro" refers to the group —NO$_2$.

"Optionally substituted" group refers to both group itself as well as the corresponding substituted group, wherein the substituted group is as defined in the disclosure. For illustration, and without limitation, an optionally substituted C$_{1-4}$alkyl refers to an alkyl group selected from the group consisting of C$_{1-4}$alkyl and substituted C$_{1-4}$alkyl as defined herein. Similarly, a C$_{1-4}$alkyl optionally substituted with up to 2 hydroxy groups refers to an alkyl group selected from the group consisting of C$_{1-4}$alkyl and C$_{1-4}$alkyl group substituted with up to 2 hydroxy groups.

"Oxo" refers to the atom (═O).

"Oxide" refers to products resulting from the oxidation of one or more heteroatoms. Examples include N-oxides, sulfoxides, and sulfones.

"Pharmaceutically acceptable carrier, excipient, or diluent" refers to a carrier, excipient, or diluent that is useful in preparing a pharmaceutical composition that is generally safe, non-toxic and neither biologically nor otherwise undesirable, and includes a carrier, excipient, or diluent that is acceptable for veterinary use as well as human pharmaceutical use. A "pharmaceutically acceptable carrier, excipient, or diluent" includes both one and more than one such carrier, excipient, or diluent.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Reduction" of a symptom or symptoms (and grammatical equivalents of this phrase) refers to decreasing the severity or frequency of the symptom(s), or elimination of the symptom(s).

"Spirocycloalkyl" refers to a 3 to 10 member cyclic substituent formed by replacement of two hydrogen atoms at a common carbon atom with an alkylene group having 2 to 9 carbon atoms, as exemplified by the following structure wherein the methylene group shown here attached to bonds marked with wavy lines is substituted with a spirocycloalkyl group:

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-cycloalkyl, —SO$_2$-substituted cylcoalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" or "sulfonate" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiol" refers to the group —SH.

"Alkylthio" refers to the group —S-alkyl wherein alkyl is as defined herein.

"Substituted alkylthio" refers to the group —S-(substituted alkyl) wherein substituted alkyl is as defined herein.

"Thiocarbonyl" refers to the divalent group —C(S)— which is equivalent to —C(=S)—.

"Thione" refers to the doubly bonded atom (=S).

"Thiocyanate" refers to the group —SCN.

"Racemates" refers to a mixture of enantiomers.

"Solvate" or "solvates" of a compound refer to those compounds, where "compounds" is as defined above, that are bound to a stoichiometric or non-stoichiometric amount of a solvent. Solvates of a compound includes solvates of all forms of the compound. In some embodiments, solvents are volatile, non-toxic, and/or acceptable for administration to humans in trace amounts. Suitable solvents include water.

"Stereoisomer" or "stereoisomers" refer to compounds that are enantiomers and/or diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N-moiety such as pyrazoles, imidazoles, benzimidazoles, triazoles, and tetrazoles.

"Therapeutically effective amount" of a drug refers to an amount of a drug that, when administered to a patient with cancer or another hyperproliferative disease, will have the intended therapeutic effect, e.g., alleviation, amelioration, palliation or elimination of one or more manifestations of cancer or another hyperproliferative disease in the patient. A therapeutic effect does not necessarily occur by administration of one dose, and may occur only after administration of a series of doses. Thus, a therapeutically effective amount may be administered in one or more administrations.

"Treating" or "treatment of" a condition or patient refers to taking steps to obtain beneficial or desired results, including clinical results. For purposes of this invention, beneficial or desired clinical results include, but are not limited to, alleviation or amelioration of one or more symptoms of cancer or another hyperproliferative disease; diminishment of extent of disease; delay or slowing of disease progression; amelioration, palliation, or stabilization of the disease state; or other beneficial results.

II. Compounds

This invention arises, in part, from the surprising discovery that certain N,N-bis-(2-halo or 2-sulfonate-ethyl)aminoaryl antineoplastic agent can be coupled to a bioreductive group optionally through a substituted methylene-SO$_2$—O—/methylene-SO$_2$NR— linker to provide for effective hypoxia activated drug compounds.

In one embodiment, there is provided a compound which comprises an optionally substituted N,N-bis-(2-halo or 2-sulfonate-ethyl)aminoaryl antineoplastic agent, an optionally substituted methylene-SO$_2$—O—/methylene-SO$_2$NR— linker, and a bioreductive group, or a pharmaceutically acceptable salt thereof wherein said compound exhibits a higher cytotoxicity under hypoxia than under normoxia. In an embodiment, the bioreductive group is a nitroheteroaryl bioreductive group.

In one embodiment, this invention provides hypoxia activated drug compounds of antineoplastic agents having formula R$_5$C(R$_3$)(R$_4$)SO$_2$-Q wherein Q is an antineoplastic agent or antiproliferative agent containing a phenolic hydroxy group and the R$_5$C(R$_3$)(R$_4$)SO$_2$ moiety is bonded to the oxygen atom of the phenolic hydroxy group of the antineoplastic agent. In one embodiment, Q is a combretastain derivative. In another embodiment, Q is etoposide. In another embodiment, Q is a duocarmycin. In another embodiment, Q is micophenolic acid. In another embodiment, Q is micophenolic acid mofentil. In another embodiment, Q is SN-38 (7-Ethyl-10-hydroxy-camptothecin). In another embodiment, Q is 10-hydroxycamptothecin.

In one aspect, there are provided compounds of Formula I or pharmaceutically acceptable salts thereof:

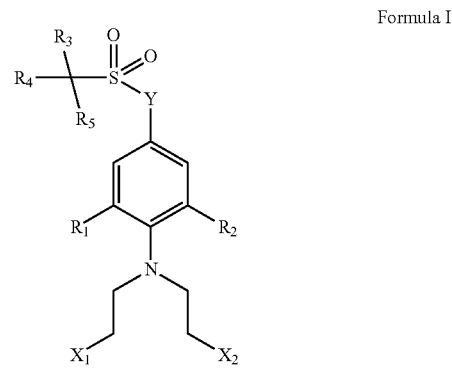

Formula I wherein each of X$_1$ and X$_2$ is independently selected from the group consisting of chloro, bromo, iodo, and sulfonate; Y is selected from the group consisting of O and NR$_6$; each of R$_1$ and R$_2$ is independently selected from the group consisting of hydrogen, halogen, and optionally substituted C$_{1-6}$alkyl; each of R$_3$ and R$_4$ is independently selected from the group consisting of hydrogen and optionally substituted C$_{1-6}$alkyl; R$_5$ is a bioreductive group selected from the group consisting of:

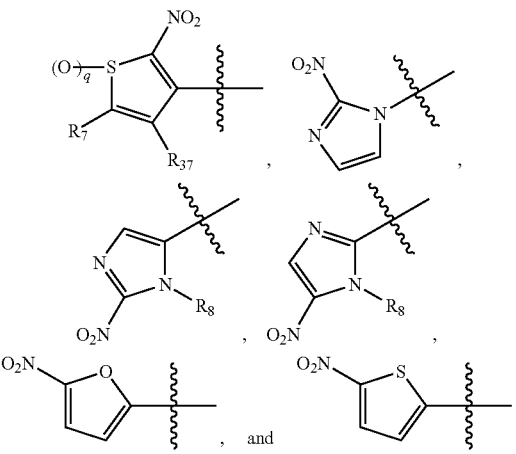

R$_6$ is selected from the group consisting of hydrogen and optionally substituted C$_{1-6}$alkyl;

R$_7$ is selected from the group consisting of hydrogen and optionally substituted C$_{1-6}$alkyl;

R$_{37}$ is hydrogen, or together with R$_7$ and the carbon atoms to which they are bonded, form an optionally substituted cycloalkyl, optionally substituted heterocyclyl, optionally substituted aryl, or optionally substituted heteroaryl moiety; R$_8$ is optionally substituted C$_{1-6}$alkyl; and q is 0, 1, or 2.

In one particular embodiment, the compounds of Formula I are represented by the formula:

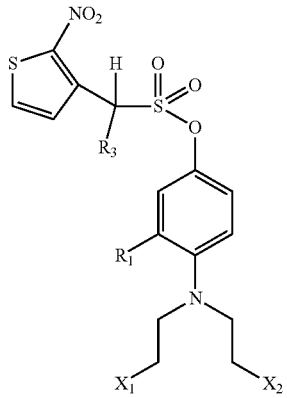

or pharmaceutically acceptable salts thereof, wherein each $X_1$ and $X_2$ independently is selected from the group consisting of chloro, bromo, and sulfonate; $R_1$ is selected from the group consisting of hydrogen and fluoro; $R_3$ is selected from the group consisting of hydrogen and an optionally substituted alkyl moiety having a structure of formula -L-$P_1$—$R_{20}$; L is optionally substituted $C_{1-4}$alkylene; $P_1$ is selected from the group consisting of a bond, —S(═O)$_2$—, and —N$R_{21}$(S═O)$_2$—; $R_{20}$ is selected from the group consisting of an optionally substituted $C_{1-4}$alkyl; optionally substituted $C_{2-4}$alkynyl; an aryl optionally substituted with a substituent selected from the group consisting of amino, substituted amino, and acylamino; optionally substituted alkoxy; optionally substituted cycloalkoxy; optionally substituted heterocyclyloxy; optionally substituted aryloxy; optionally substituted heteroaryloxy; an optionally substituted heteroaryl moiety containing a basic nitrogen atom that is either part of the heteroaryl ring or is a heteroaryl ring substituent; an optionally substituted heterocycle containing up to 2 nitrogen atoms; and $R_{21}$ is selected from the group consisting of hydrogen and optionally substituted $C_{1-4}$alkyl.

In one aspect of this embodiment, $R_1$ is hydrogen. In one aspect of this embodiment, $R_1$ is fluoro. In one aspect of this embodiment, L is an optionally substituted $C_{1-2}$alkylene. In one particular aspect of this aspect, L is optionally substituted $C_1$alkylene. In another particular aspect of this aspect, L is optionally substituted $C_2$alkylene. In one particular aspect of this aspect, L is —CH$_2$—. In one particular aspect of this aspect, L is —CH$_2$—CH$_2$—.

In one aspect of this embodiment, $R_3$ is hydrogen.

In one aspect of this embodiment, $P_1$ is a bond. In one particular aspect of this aspect, $R_{20}$ is an optionally substituted heteroaryl moiety containing a basic nitrogen atom selected from the group consisting of benzotriazolyl, imidazopyridyl, imidazolyl, and pyridyl. In one particular aspect of this aspect, $R_{20}$ is an optionally substituted $C_{2-4}$alkynyl. In one particular aspect of this aspect, $R_{20}$ is selected from the group consisting of optionally substituted alkoxy, optionally substituted cycloalkoxy, optionally substituted heterocyclyloxy, optionally substituted aryloxy, and optionally substituted heteroaryloxy.

In another particular embodiment, the compounds of Formula I are represented by the formula:

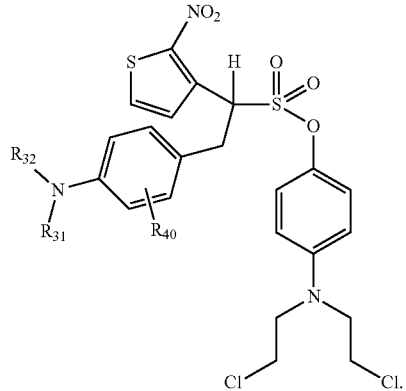

or pharmaceutically acceptable salts thereof, wherein each of $R_{31}$ and $R_{32}$ is independently selected from the group consisting of hydrogen, optionally substituted alkyl, and —C(═O)—C$R_{33}$($R_{34}$)($R_{35}$) or where one of $R_{31}$ or $R_{32}$ is selected from the group consisting of —SO$_2$-T where T is optionally substituted aryl or optionally substituted heteroaryl; $R_{33}$ is amino; $R_{34}$ is selected from the group consisting of hydrogen and optionally substituted $C_{1-4}$alkyl; $R_{35}$ is $C_{1-6}$alkyl optionally substituted with a substituent selected from the group consisting of optionally substituted amino and optionally substituted guanidine; and $R_{40}$ is selected from the group consisting of hydrogen and halogen.

In one aspect of this embodiment, $R_{31}$ is hydrogen, and $R_{32}$ is —C(═O)CH(NH$_2$)(CH$_2$)$_4$NH$_2$. In one aspect of this embodiment, $R_{40}$ is hydrogen. In another aspect of this embodiment, $R_{40}$ is halogen.

In another particular embodiment, the compounds of Formula I are represented by the formula:

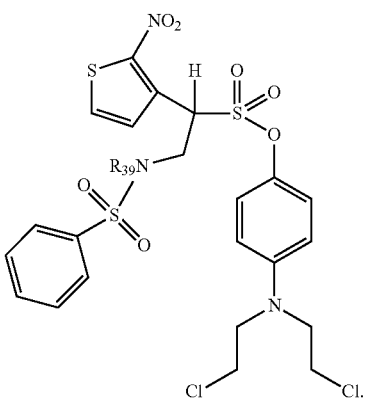

or pharmaceutically acceptable salts thereof, wherein $R_{39}$ is selected from the group consisting of hydrogen and optionally substituted $C_{1-4}$alkyl.

In another particular embodiment, the compounds of Formula I are represented by the formula:

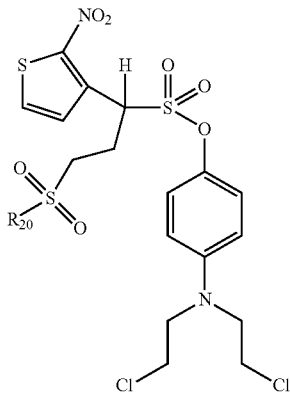

or pharmaceutically acceptable salts thereof, wherein $R_{20}$ is selected from the group consisting of $C_{1-4}$alkyl optionally substituted with up to 2 hydroxy groups; —O-T; —$NR_{38}$-T; and a nitrogen containing heterocycle wherein the point of attachment of said heterocycle to the $SO_2$ group is through a nitrogen atom, where T is as defined above and $R_{38}$ is optionally substituted $C_{1-6}$alkyl.

In one aspect of this embodiment, said nitrogen containing heterocycle is represented by the formula:

wherein $R_{22}$ is $C_{1-4}$alkyl.

In another aspect of this embodiment, $R_{20}$ is $C_{1-4}$alkyl optionally substituted with up to 2 hydroxy groups. In another aspect of this embodiment, $R_{20}$ is —O-T wherein T is optionally substituted aryl or optionally substituted heteroaryl or in other words, $R_{20}$ is selected from the group consisting of optionally substituted aryloxy and optionally substituted heteroaryloxy. In another particular embodiment, the compounds of Formula I are represented by the formula:

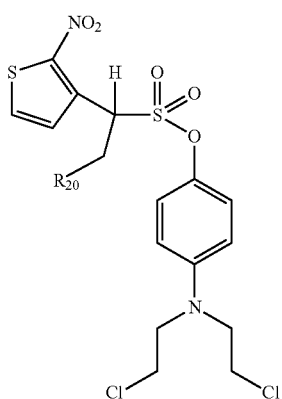

or pharmaceutically acceptable salts thereof, wherein $R_{20}$ is substituted pyridyl having the structure of formula:

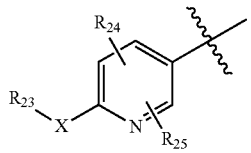

wherein $R_{23}$ is selected from the group consisting of hydrogen, $C_{1-4}$alkyl optionally substituted with up to 2 hydroxy groups, and —(C=O)$CR_{27}(R_{28})(R_{29})$; $R_{24}$ is selected from the group consisting of hydrogen and optionally substituted $C_{1-4}$alkyl; $R_{25}$ is selected from the group consisting of hydrogen and halogen; X is selected from the group consisting of $NR_{26}$, O, and a bond; each of $R_{26}$, $R_{27}$, and $R_{28}$ independently is selected from the group consisting of hydrogen and optionally substituted $C_{1-4}$alkyl; and $R_{29}$ is selected from the group consisting of hydroxy, optionally substituted alkoxy, and optionally substituted $C_{1-4}$alkyl; with the proviso that when X is a bond, $R_{23}$ is hydrogen and with the proviso that when X is O, $R_{23}$ excludes —(C=O)$CR_{27}(R_{28})(R_{29})$.

In aspect of this embodiment, X is O. In another aspect of this embodiment, X is $NR_{26}$. In an aspect within this aspect, $R_{27}$ and $R_{28}$ is methyl and $R_{29}$ is hydroxyl. In another aspect, $R_{26}$ is hydrogen.

In another particular embodiment, the compounds of Formula I are represented by the formula:

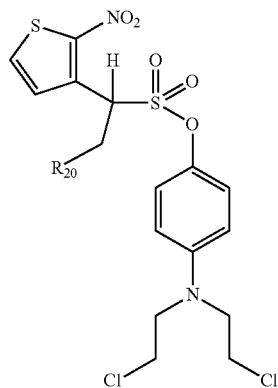

or pharmaceutically acceptable salts thereof, wherein $R_{20}$ is selected from the group consisting of:

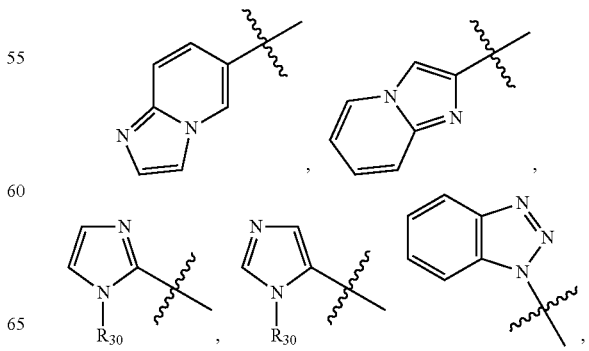

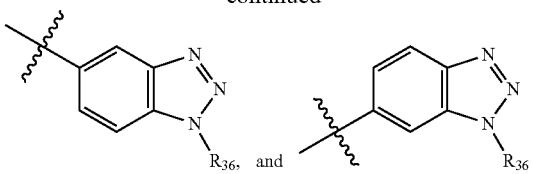

wherein $R_{30}$ is optionally substituted $C_{1-4}$alkyl and $R_{36}$ is $C_{1-4}$alkyl optionally substituted with up to 2 hydroxy groups.

Compounds of Formula I include, without limitation, compounds selected from the group consisting of:

TH-1266: 3-(4-(N,N-bis-(2-Chloroethyl)amino)phenoxysulfonyl-(2-methylsulfonyl)ethyl)methyl-2-nitrothiophene; TH-1315: 3-(4-(N,N-bis-(2-Chloroethyl)amino)phenoxysulfonyl-(2-(2-hydroxyethoxy)pyridin-5-yl-methyl))methyl-2-nitrothiophene; TH-1343: 3-(4-(N,N-bis-(2-Chloroethyl)amino)phenoxysulfonyl-(benzotriazol-1-yl-methyl))methyl-2-nitrothiophene; TH-1330: 3-(4-(N,N-bis-(2-Chloroethyl)amino)phenoxysulfonyl-(4-aminophenylmethyl))methyl-2-nitrothiophene (trifluoroacetate salt); TH-1457: 3-(4-(N,N-bis-(2-Chloroethyl)amino)phenoxysulfonyl-(1-(2-hydroxyethyl)benzotriazol-6-yl-methyl))methyl-2-nitrothiophene; TH-1292: 3-(4-(N,N-bis-(2-Chloroethyl)amino)phenoxysulfonyl-(2-phenoxysulfonylethyl))methyl-2-nitrothiophene; TH-1442: 3-(4-(N,N-bis-(2-Chloroethyl)amino)phenoxysulfonyl-((2-methylamino)pyridin-5-yl)methyl))methyl-2-nitrothiophene; TH-1451: 3-(4-(N,N-bis-(2-Chloroethyl)amino)phenoxysulfonyl-(1-(2-hydroxyethyl)benzotriazol-5-yl-methyl))methyl-2-nitrothiophene; TH-1218: 3-(4-(N,N-bis-(2-Chloroethyl)amino)phenoxysulfonyl-(phenylsulfonylaminomethyl))methyl-2-nitrothiophene; TH-1456: 3-(4-(N,N-bis-(2-Chloroethyl)amino)phenoxysulfonyl-(imidazopyridin-2-yl-methyl))methyl-2-nitrothiophene; TH-1331: 3-(4-(N,N-bis-(2-Chloroethyl)amino)phenoxysulfonyl-(pyridin-3-yl-methyl))methyl-2-nitrothiophene; TH-1305: 3-(4-(N,N-bis-(2-Chloroethyl)amino)phenoxysulfonyl-(2-hydroxypyridin-5-yl-methyl))methyl-2-nitrothiophene; TH-1354: 3-(4-(N,N-bis-(2-Chloroethyl)amino)phenoxysulfonyl-(2-(hydroxyacetylamino)pyridin-5-yl-methyl))methyl-2-nitrothiophene; TH-1465: 3-(4-(N,N-bis-(2-Chloroethyl)amino)phenoxysulfonyl-(2-(lactic acylamino)pyridine-5-yl-methyl))methyl-2-nitrothiophene; TH-1326: 3-(4-(N,N-bis-(2-Chloroethyl)amino)phenoxysulfonyl-(2-((N-methylpiperazin-4-yl)sulfonyl)ethyl))methyl-2-nitrothiophene; TH-1366: 3-(4-(N,N-bis-(2-Chloroethyl)amino)phenoxysulfonyl-(N-methylimidazol-2-yl-methyl))methyl-2-nitrothiophene; TH-1192: 3-((3-Fluoro-4-(N,N-bis-(2-chloroethyl)amino)phenoxy)sulfonyl)methyl-2-nitrothiophene; TH-1388: 3-(4-(N,N-bis-(2-Chloroethyl)amino)phenoxysulfonyl-(2-(2-hydroxyethylsulfonyl)ethyl))methyl-2-nitrothiophene; TH-1365: 3-(4-(N,N-bis-(2-Chloroethyl)amino)phenoxysulfonyl-(N-methylimidazol-5-yl-methyl))-2-nitrothiophene; TH-1255: 3-(4-(N,N-bis-(2-Chloroethyl)amino)phenoxysulfonyl-(2-aminopyridin-5-yl-methyl))methyl-2-nitrothiophene trifluoroacetate; TH-1435: 3-(4-(N,N-bis-(2-Chloroethyl)amino)phenoxysulfonyl-(imidazopyidin-5-yl-methyl))methyl-2-nitrothiophene; TH-1475: 3-(4-(N,N-bis-(2-Chloroethyl)amino)phenoxysulfonyl-(2-(2-hydroxyethoxy)-4-chloro-6-methylpyridin-5-yl-methyl))methyl-2-nitrothiophene; TH-1478: 3-(4-(N,N-bis-(2-Chloroethyl)amino)phenoxysulfonyl-(2-(N-methoxyacetyl-N-methylamino)pyridin-5-yl-methyl))methyl-2-nitrothiophene; TH-1405: 3-(4-(N,N-bis-(2-Chloroethyl)amino)phenoxysulfonyl-(2-(lysylamino)pyridine-5-yl-methyl))methyl-2-nitrothiophene (dihydrochloride salt); and TH-1504: 3-(4-(N,N-bis-(2-Chloroethyl)amino)phenoxysulfonyl-(2-chloro-4-aminophenyl-methyl))methyl-2-nitrothiophene (trifluoroacetate salt);

In another embodiment, this invention provides for intermediates of the formula:

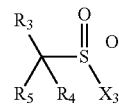

wherein $X_3$ is selected from the group consisting of halo and sulfonate; and $R_3$, $R_4$, and $R_5$ is defined as in Formula I above.

In one aspect, $R_5$ is

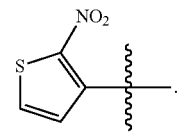

In another aspect, $X_3$ is chloro or bromo. These compounds are useful for masking phenolic hydroxy groups, in presence of amino or aliphatic hydroxy groups. These compounds are also useful for masking amino groups, in presence of hydroxy groups. One of skill in the art, upon reading this disclosure and methods described in the literature, will be able to select an appropriate $R_5C(R_3)(R_4)SO_2$—$X_3$ compound as provided herein for masking or protecting amino, alkylamino, and phenolic hydroxy groups. After the $R_5C(R_3)(R_4)SO_2$ moiety is placed on the amino, alkylamino, and/or phenolic hydroxy group to provide, for example, and without limitations, for compounds of the formula $R_5C(R_3)(R_4)SO_2O$—Z or $R_5C(R_3)(R_4)SO_2NR^{21}$—Z where Z is an optionally substituted aryl or heteroaryl group and $NHR^{21}$ is a monosubstituted amino group as defined above, the $R_5C(R_3)(R_4)SO_2$ moiety can subsequently be removed under mild reductive conditions to provide the $H_2N$—Z, HR'N—Z, or HO—Z compound. Thus, compounds of the formula $R_5C(R_3)(R_4)SO_2$—$X_3$ are useful in organic synthesis as a phenolic, amino, or alkylamino masking group.

In certain other embodiments, the present invention provides a compound of the present invention in a substantially pure form. In various embodiments, the compound is up to 80%, up to 90%, up to 99%, and greater than 99% pure. In another embodiment, the present invention provides a pharmaceutical formulation comprising a compound of the present invention, as provided hereinabove, and a pharmaceutically acceptable carrier, excipient, or diluent.

Synthetic Methods

The compounds disclosed herein can be prepared by following the general procedures and examples set forth below. It will be appreciated that where typical or preferred process conditions (i.e., reaction temperatures, times, mole ratios of reactants, solvents, pressures, and the like) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

If the compounds of this invention contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like. Specific exemplification of the synthesis of the compounds of this invention are provided in the EXAMPLES section below. The following general synthetic section provides a generic pathway for the synthesis of such compound.

Specifically, in the methods provided below, an intermediate is alkylated in presence of a hydroxide and tertiary butoxide to yield the compounds of the invention.

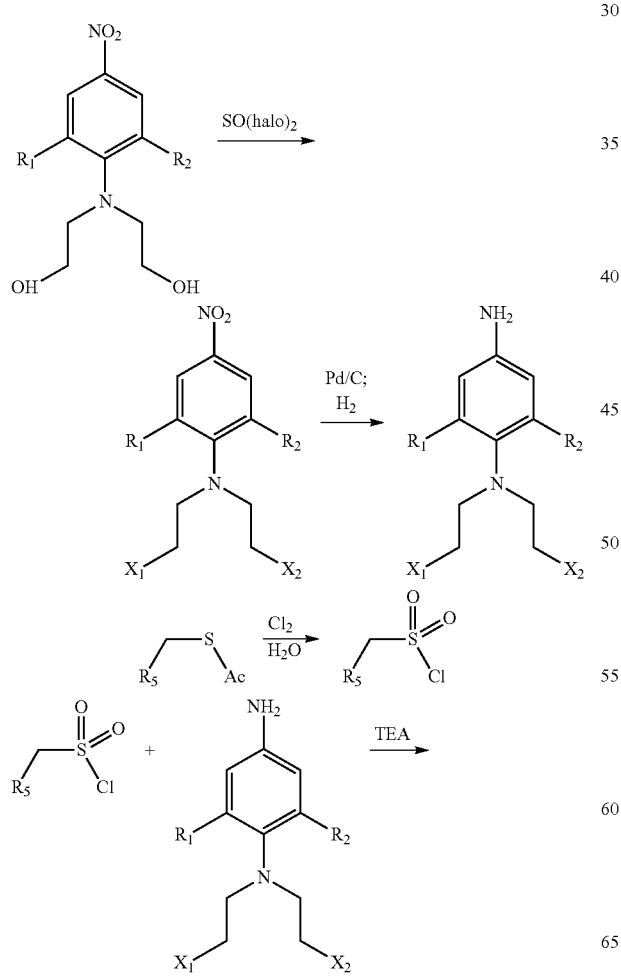

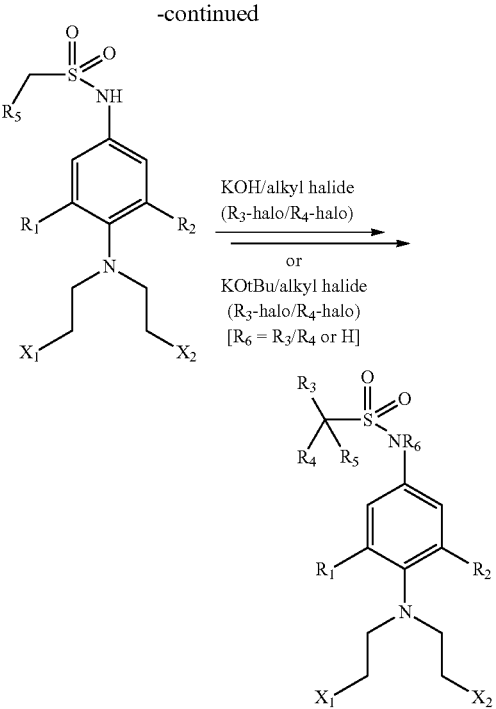

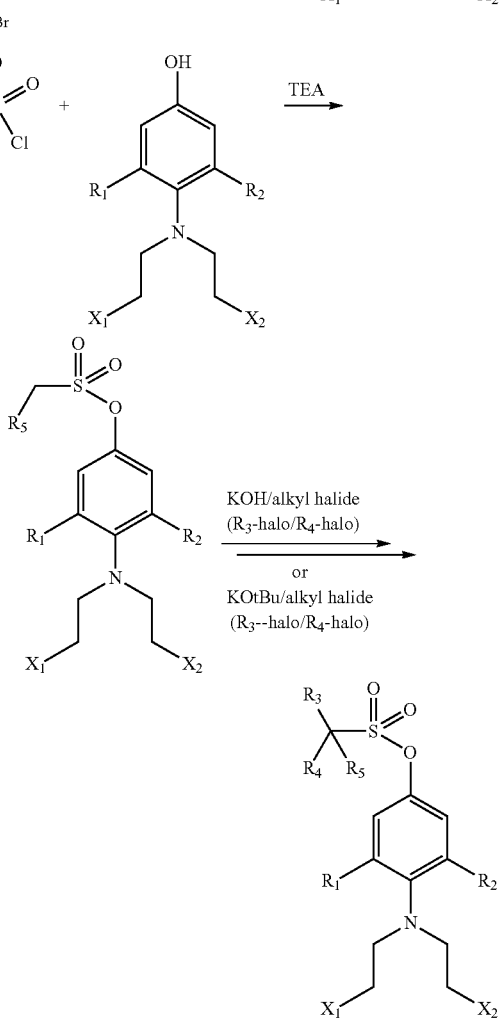

In the methods provided below, a Mitsunobu reaction and a Michael addition are employed to yield the compounds of the invention.

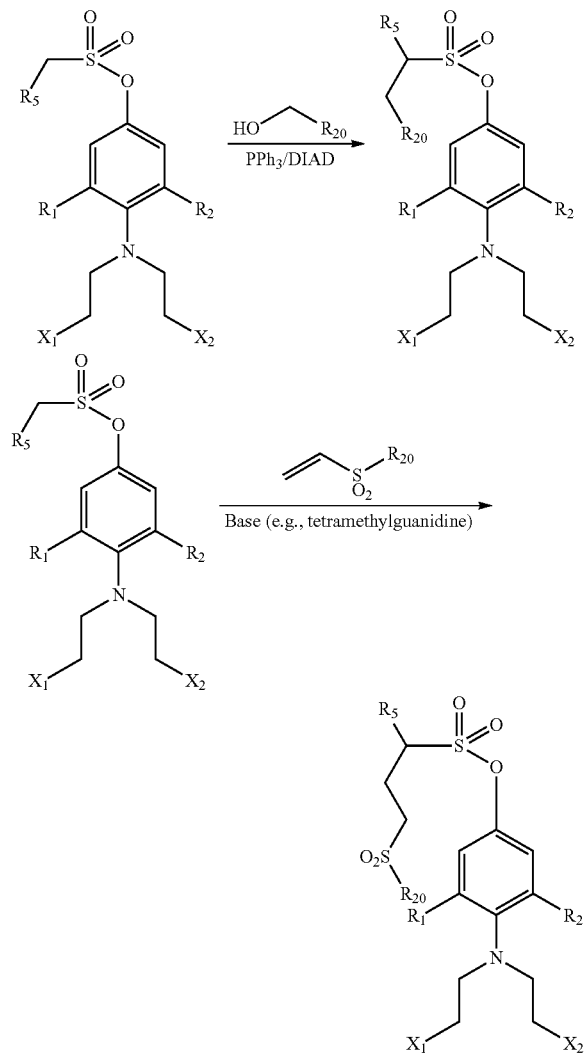

In another embodiment, the present invention provides methods of synthesizing the compounds of the present invention as described above and in the EXAMPLES section.

Methods of making hypoxia activated drug compounds of the present invention wherein the antineoplastic agents are agents other than N,N-bis(2-halo/2-sulfonate-ethyl)-aryl/heteroaryl compounds will be apparent to one of skill in the art upon reading this disclosure and from methods known in literature.

Methods for synthesizing a variety of bioreductive groups, other than those described here, and useful is the synthesis of the compounds of the present invention, are provided in PCT Pat. Pub. No. WO 09/033,165, WO 09/018,163, WO 08/151,253, WO 00/064864, WO 04/087075, WO 06/057946, WO 07/002,931, WO 07/137,196 and WO 08/083,101, and can be adapted in accordance with the present methods by one of skill in the art upon reading this disclosure.

Treatment Methods

TH 1315 and certain other nitrogen mustard alkylator drugs of the present invention are effective in treating cancer as demonstrated by treating xenograft solid tumors in mice. The in vivo results are described in Example 2C below.

Thus, in another embodiment, the present invention provides a method of treating cancer and other hyperproliferative diseases comprising administering a therapeutically effective amount of a compound of the present invention to a patient in need of such treatment. In one embodiment, the therapeutically effective amount of the compound administered is a daily dose in the range of 1 mg/m$^2$-10,000 mg/m$^2$, 5 mg/m$^2$-5000 mg/m$^2$, mg/m$^2$-3000 mg/m$^2$, 100 mg/m$^2$-2000 mg/m$^2$, 200 mg/m$^2$-1000 mg/m$^2$, and 400 mg/m$^2$-800 mg/m$^2$. For an adult human patient, 1 mg/m$^2$ is equal to about 1.7 mg/kg. In another embodiment, this invention provides the use of a compound of this invention in the manufacture of a medicament for treating cancer in a patient.

In one embodiment, the compounds of the present invention are administered in the form of pharmaceutically acceptable formulations. In another embodiment, the pharmaceutical formulations are administered parenterally. In another embodiment, the pharmaceutical formulations are administered by i.v. or i.p. injection or by infusion. In another embodiment, the pharmaceutical formulations are administered orally (p.o.).

The compounds of the present invention can be administered in accordance with any of a variety of dosing schedules including but not limited to daily or once every other day or once a week to the patient. Multiple daily administrations of a compound of the present invention can also be employed in the methods of the invention. Depending on the dose selected by the practitioner and the convenience of the patient, the entire daily dose may be administered once daily or the daily dose may be administered in multiple smaller doses throughout the course of a day. The compounds of the present invention need not, however, be administered daily; for example a daily dose used for some patients or indications may be, in other patients or for other indications, given every other day, or less frequently.

In one embodiment, the daily dose is repeatedly administered over a period of time. In this embodiment, the administration of the therapeutically effective daily dose is continued for multiple days, typically for at least three consecutive days, or for at least a week, or for several weeks, or for several months, or for several years, or until cancer (or another hyperproliferative disease) or one or more of its symptoms disappears or substantially abates, or up to the rest of the patient's life. As is well understood in the field of medicine, treatment can be suspended temporarily if toxicity is observed or for the convenience of the patient without departing from the scope of the invention.

In various embodiments, the compounds of the present invention are administered qd, bid, tid, qid, qod, q2d, twice weekly, q7d, or qweek, and treatment is continued for a period ranging from three days to the longer periods enumerated above.

The methods of cancer treatment employing hypoxia activated drugs of nitrogen mustard alkylators (nitrogen mustard alkylator drugs) of the present invention are effective in killing the most difficult to kill cancer cells growing in the hypoxic region of a tumor. After administering the nitrogen mustard alkylator drugs to a cancer patient, the hypoxic regions of the cancer act as a drug-factory to produce an alkylator for killing cancer cells, relative to normal tissues, and leading to a higher concentration of the nitrogen mustard alkylator within and near the tumor. While cancer cells in the hypoxic region of the tumor are destroyed by the action of the nitrogen mustard alkylator drugs of the present invention, normoxic cancer cells can be killed by the nitrogen mustard alkylator generated from the corresponding nitrogen mustard alkylator drug of this invention, or by other anticancer agents administered in combination with the nitrogen mustard alkylator drug. The administration in combination, or coadministration, of a nitrogen mustard alkylator drug of the present invention with another anti cancer agent is described in the following section and exemplified in Example 2C.

Combination Therapies

In another embodiment, the present invention provides a method of treating cancer and other hyperproliferative diseases comprising administering a therapeutically effective amount of a compound of the present invention in combination with another anticancer agent or anticancer therapy to a patient in need of such treatment. In another embodiment, this invention provides the use of a compound of this invention in the manufacture of a medicament for treating cancer in a patient, wherein the medicament is for use in combination with the administration of another anticancer agent or anticancer therapy.

In accordance with the methods of the invention, a nitrogen mustard alkylator drug of the present invention (or a nitrogen mustard alkylator drug, or the compounds of the present invention) can be coadministered in combination with other anti cancer agents. Without intending to be bound by any particular mechanism or effect, such coadministration can in some cases provide one or more of several advantages over known cancer therapies. For example, coadministration of a nitrogen mustard alkylator drug and another anticancer agent has a synergistic effect on induction of cancer cell death. Two drugs can be said to possess therapeutic synergy if a combination dose regimen of the two drugs produces a significantly better tumor cell kill than the sum of the constituent single agents at optimal or maximum tolerated doses.

The degree of synergy can be defined as net log of tumor cell kill by the optimum combination regimen minus net log of tumor cell kill by the optimal dose of the most active single agent. Differences in cell kill of greater than ten-fold (one log) can indicate therapeutic synergy. Those of skill in the art can readily determine the anti cancer drugs that act synergistically with a nitrogen mustard alkylator drug as described herein. For example, the references Vendetti, "Relevance of Transplantable Animal-Tumor Systems to the Selection of New Agents for Clinical Trial," Pharmacological Basis of Cancer Chemotherapy, Williams and Wilkins, Baltimore, 1975, and Simpson Herren et al., 1985, "Evaluation of In Vivo Tumor Models for Predicting Clinical Activity for Anticancer Drugs," Proc. Am. Assoc. Cancer Res. 26: 330, each of which is incorporated herein by reference, describe methods to aid in the determination of whether two drugs act synergistically. While synergy is not required for therapeutic benefit in accordance with the methods described herein, in one embodiment, the present invention provides a method of cancer treatment, wherein there is synergy between a nitrogen mustard alkylator drug and another anticancer agent.

In general, coadministration of anti cancer agents in accordance with the present methods provides a better therapeutic result than administration of the anticancer agent alone. Such coadministration can provide greater alleviation or amelioration of one or more symptoms of the cancer, diminishment of extent of disease, delay or slowing of disease progression, amelioration, palliation or stabilization of the disease state, partial or complete remission, prolonged survival or other beneficial therapeutic results.

As used herein, a nitrogen mustard alkylator drug is coadministered with another anticancer agent (also referred to herein as, "Agent") when a nitrogen mustard alkylator drug and Agent are administered as part of the same course of therapy. The coadministration of a nitrogen mustard alkylator drug increases the sensitivity of cancer cells to the other anticancer agent, allowing lower doses of the anticancer agent to be administered to the patient, or allowing an anticancer agent to be used for treatment of cells otherwise resistant to the anticancer agent or otherwise refractory to treatment. One of skill in the art will appreciate upon reading this disclosure that, while the known anti cancer agents in general targets the rapidly dividing cells in the normoxic region, the nitrogen mustard alkylator drugs of the invention target the hypoxic cells in the regions of tumors that are not efficiently killed by the anticancer agent alone.

In one embodiment, a nitrogen mustard alkylator drug is first administered prior to administration of the Agent, (i.e., the initiation of the other cancer therapy), and treatment with a nitrogen mustard alkylator drug is continued throughout the course of administration of the Agent (i.e., the course of the other therapy). In another embodiment, a nitrogen mustard alkylator drug is administered after the initiation or completion of the other cancer therapy. In other embodiments, a nitrogen mustard alkylator drug is administered contemporaneously with the initiation of the other cancer therapy. Therefore, when a nitrogen mustard alkylator drug is used in combination with one or more of the additional therapies, a nitrogen mustard alkylator drug and additional therapy can be administered at the same time or can be administered separately. See, for example, combination therapy as described in Example 2C.

In one embodiment, a nitrogen mustard alkylator drug is first administered prior to administration of the Agent, and treatment with a nitrogen mustard alkylator drug is continued after the cessation of administration of the Agent. In one embodiment, a nitrogen mustard alkylator drug is first administered prior to administration of the Agent, and treatment with a nitrogen mustard alkylator drug is continued during part of the period of administration of the Agent. For certain drugs, such as certain topoisomerase inhibitors, a nitrogen mustard alkylator drug administration can be initiated and completed prior to the administration of the second drug.

Anticancer drug therapy typically involves multiple rounds, or cycles, of administration of the anti cancer agent(s). In the context of administering a nitrogen mustard alkylator drug, each cycle of administration (as well as a complete set of cycles) can be viewed as administration of a second drug. A nitrogen mustard alkylator drug can be administered in any or all of the multiple cycles of treatment with the other Agent; in general, a nitrogen mustard alkylator drug is administered on a daily basis for at least two or more days during each cycle. In one embodiment of the invention, a nitrogen mustard alkylator drug is coadministered with the Agent according to a schedule repeated at each round.

In some embodiments, the drug coadministered with a nitrogen mustard alkylator drug will be delivered at a lower dose, and optionally for longer periods, than would be the case in the absence of a nitrogen mustard alkylator drug administration. Such "low dose" therapies can involve, for example, administering an anti cancer drug, including, but not limited to, paclitaxel, docetaxel, doxorubicin, cisplatin, carboplatin, or alimta, at a lower than approved dose and for a longer period of time together with a nitrogen mustard alkylator drug administered in accordance with the methods described herein.

These methods can be used to improve patient outcomes over currently practiced therapies by more effectively killing cancer cells or stopping growth of cancer cell as well as diminishing unwanted side effects of the other therapy. When employed in combination with a nitrogen mustard alkylator drug, the additional anti cancer agent(s) is dosed using either the standard dosages employed for those Agents (i.e., when used without a nitrogen mustard alkylator drug) or are less than those standard dosages.

The administration of a nitrogen mustard alkylator drug in accordance with the methods described herein, can therefore allow the physician to treat cancer with existing (or later approved) drugs at lower doses (than currently used), thus ameliorating some or all of the toxic side effects of such drugs. The exact dosage for a given patient varies from patient to patient, depending on a number of factors including the drug combination employed, the particular disease being treated, and the condition and prior history of the patient, but can be determined using only the skill of the ordinarily skilled artisan in view of the teachings herein.

Specific dose regimens for known and approved chemotherapeutic agents or antineoplastic agents (i.e., the recommended effective dose) are known to physicians and are given, for example, in the product descriptions found in the Physician's Desk Reference 2003, (Physicians' Desk Reference, 57th Ed) Medical Economics Company, Inc., Oradell, N.J.; Goodman and Gilman's The pharmacological basis of therapeutics. Eds. Hardman et al., McGraw-Hill. New York. (US) 1996, 9th Ed., and/or are available from the Federal Drug Administration. Illustrative dosage regimens for certain anti cancer drugs are also provided below.

In one embodiment of the method of treating cancer using the a nitrogen mustard alkylator drug, a nitrogen mustard alkylator drug is administered in combination with an effective amount of one or more chemotherapeutic agents, an effective amount of radiotherapy, an appropriate surgery procedure, or any combination of such additional therapies. The Agents can be administered as the same or different formulations and can be administered via the same or different routes.

Cancer drugs or Agents can generally be classified as alkylators, anthracyclines, antibiotics, aromatase inhibitors, bisphosphonates, cyclo-oxygenase inhibitors, estrogen receptor modulators, folate antagonists, inorganic aresenates, microtubule inhibitors, modifiers, nitrosoureas, nucleoside analogs, osteoclast inhibitors, platinum containing compounds, retinoids, topoisomerase 1 inhibitors, topoisomerase 2 inhibitors, and tyrosine kinase inhibitors. In accordance with the methods described herein, a nitrogen mustard alkylator drug can be coadministered with any anti cancer drug from any of these classes or can be administered prior to or after treatment with any such drug or combination of such drugs. In addition, a nitrogen mustard alkylator drug can be administered in combination with a biologic therapy (e.g., treatment with interferons, interleukins, colony stimulating factors and monoclonal antibodies). Biologics used for treatment of cancer are known in the art and include, without limitation, avastin, trastuzumab (Herceptin), tositumomab [131]I (Bexxar), and rituximab (Rituxan).

In one embodiment, the Agent is a chemotherapeutic agent that can be used in combination with the nitrogen mustard alkylator drug of the invention. Such chemotherapeutic agents include, but are not limited to, busulfan, improsulfan, piposulfan, benzodepa, carboquone, 2-deoxy-D-glucose, lonidamine and analogs thereof, glufosfamide, gemcitibine, erlotinib, meturedepa, uredepa, altretamine, imatinib, triethylenemelamine, triethylenephosphoramide, triethylenethiophosphoramide, trimethylolomelamine, chlorambucil, chlornaphazine, estramustine, ifosfamide, gefitinib, mechlorethamine, mechlorethamine oxide hydrochloride, melphalan, novembichin, phenesterine, prednimustine, trofosfamide, uracil mustard, carmustine, chlorozotocin, fotemustine, nimustine, ranimustine, dacarbazine, mannomustine, mitobronitol, mitolactol, pipobroman, aclacinomycins, actinomycin, anthramycin, azaserine, bleomycin, cactinomycin, carubicin, carzinophilin, chromomycin, dactinomycin, daunorubicin, daunomycin, 6-diazo-5-oxo-1-norleucine, mycophenolic acid, nogalamycin, olivomycin, peplomycin, plicamycin, porfiromycin, puromycin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, 5-fluorouracil, tegafur, L-asparaginase, pulmozyme, aceglatone, aldophosphamide glycoside, aminolevulinic acid, amsacrine, bestrabucil, bisantrene, cisplatin, oxoplatin, carboplatin, defofamide, demecolcine, diaziquone, elformithine, elliptinium acetate, etoglucid, flutamide, gallium nitrate, hydroxyurea, interferon-alpha, interferon-beta, interferon-gamma, interleukin-2, lentinan, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, paclitaxel, tamoxifen, erlotonib, teniposide, tenuazonic acid, triaziquone, 2,2',2"-trichlorotriethylamine, urethan, vinblastine, cyclophosphamide, and vincristine. Combination treatment including various nitrogen mustard alkylator drugs of the present invention and Agents are further disclosed below.

In one embodiment, a nitrogen mustard alkylator drug described herein can be used in combination with an angiogenesis inhibitor (anti angiogenic agent) including, but not limited to, avastin and similar therapeutics. In one embodiment of the combination treatment methods, a subject is treated with an angiogenesis inhibitor and subsequently treated with a nitrogen mustard alkylator drug. In one embodiment of the combination treatment methods, a subject is treated with an angiogenesis inhibitor and subsequently treated with a nitrogen mustard alkylator drug with another chemotherapeutic agent, including, but not limited to, cisplatin, and carboplatin. In one embodiment of these combination methods of treatment using an angiogenesis inhibitor, the method is used to treat breast cancer.

In another embodiment, a nitrogen mustard alkylator drug is administered with an anti angiogenic agent, including, but not limited to, anti angiogenic agents selected from the group consisting of angiostatin, an agent that inhibits or otherwise antagonizes the action of VEGF, batimastat, captopril, cartilage derived inhibitors, genistein, endostatin, interleukin, lavendustin A, medroxyprogesterone acetate, recombinant human platelet factor 4, taxol, tecogalan, thalidomide, thrombospondin, TNP-470, and avastin. Other useful angiogenesis inhibitors for purposes of the combination therapies provided by the present methods and compositions described herein include Cox-2 inhibitors like celecoxib (Celebrex), diclofenac (Voltaren), etodolac (Lodine), fenoprofen (Nalfon), indomethacin (Indocin), ketoprofen (Orudis, Oruvail), ketorolac (Toradol), oxaprozin (Daypro), nabumetone (Relafen), sulindac (Clinoril), tolmetin (Tolectin), rofecoxib (Vioxx), ibuprofen (Advil), naproxen (Aleve, Naprosyn), aspirin, and acetaminophen (Tylenol).

In another embodiment, a nitrogen mustard alkylator drug is administered with an anti cancer agent that acts, either directly or indirectly, to inhibit the epidermal growth factor or EGFR receptor. EGFR inhibitors suitable for coadministration with a nitrogen mustard alkylator drug of the invention include gefitinib and erlotonib.

In another embodiment, a nitrogen mustard alkylator drug is administered with an anti cancer agent that acts, either directly or indirectly, to inhibit hypoxia-inducible factor 1 alpha (HIF1α) or to inhibit a protein or enzyme, such as a glucose transporter or VEGF, whose expression or activity is increased upon increased HIF1α levels. HIF1α inhibitors suitable for use in this embodiment of the methods and compositions described herein include P1 3 kinase inhibitors; LY294002; rapamycin; histone deacetylase inhibitors such as [(E)-(1S,4S,10S,21R)-7-[(Z)-ethylidene]-4,21-diisopropyl-2-oxa-12,13-dithia-5,8,20,23-tetraazabicyclo-[8,7,6]-tricos-16-ene-3,6,9,19,22-pentanone (FR901228, depsipeptide); heat shock protein 90 (Hsp90) inhibitors such as geldanamycin, 17-allylamino-geldanamycin (17-AAG), and other geldanamycin analogs, and radicicol and radicicol derivatives such as KF58333; genistein; indanone; staurosporin; protein kinase-1 (MEK-I) inhibitors such as PD98059 (2'-ammo-3'-methoxyflavone); PX-12 (1-methylpropyl 2-imidazolyl disulfide); pleurotin PX-478; quinoxaline 1,4-dioxides; sodium butyrate (NaB); sodium nitropurruside (SNP) and other NO donors; microtubule inhibitors such as novobiocin, panzem (2-methoxyestradiol or 2-ME2), vincristines, taxanes, epothilones, discodermolide, and derivatives of any of the foregoing; coumarins; barbituric and thiobarbituric acid analogs; camptothecins; and YC—I, a compound described in Biochem. Pharmacol., 15 Apr. 2001, 61(β):947-954, incorporated herein by reference, and its derivatives.

Alkylators useful in the practice of the combination treatment methods described herein include, but are not limited to, busulfan (Myleran, Busulfex), chlorambucil (Leukeran), ifosfamide (with or without MESNA), cyclophosphamide (Cytoxan, Neosar), glufosfamide, melphalan, L-PAM (Alkeran), dacarbazine (DTIC-Dome), and temozolamide (Temodar). In accordance with the methods described herein, a nitrogen mustard alkylator drug is coadministered with an alkylator to treat cancer. In one embodiment, the compounds of the present invention are co-administered with TH-302. In one embodiment, the cancer is chronic myelogenous leukemia, multiple myeloma, or anaplastic astrocytoma.

In one embodiment, the present invention provides a method of treating cancer treatable by administering an alkylator by administering the nitrogen mustard alkylator drugs of the present invention, alone, and in combination with at least another alkylator or a drug thereof. Such alkylators include, without limitation, cyclophosphamide, ifosfamide, glufosfamide, mechlorethamine, melphalan, chlorambucil, dacarbazine, temozolomide, carmustirie, streptozocin, bendamustin, busulfan, thiotepa, cisplatin, carboplatin, and oxaliplatin. Types of cancers treated using any one of such alkylators alone or in combination with other anti cancer or chemoprotective agents are described for example in the reference Hardman et al. (supra).

In one embodiment, the present invention provides a method of treating cancer by coadministering a nitrogen mustard alkylator drug with at least the alkylator cyclophosphamide, in the treatment of Stages III and IV malignant lymphomas, multiple myeloma, leukemia, mycosis fungoides, neuroblastoma, ovarian adenocarcinoma, retinoblastoma, and carcinoma of the breast. Cyclophosphamide is administered for induction therapy in doses of 1500-1800 mg/m² that are administered intravenously in divided doses over a period of three to five days; for maintenance therapy, 350-550 mg/m² are administered every 7-10 days, or 110-185 mg/m² are administered intravenously twice weekly. In accordance with the methods described herein, cyclosphosphamide is coadministered with a nitrogen mustard alkylator drug at such doses or at lower doses and/or for a longer duration than normal for administration of cyclosphosphamide alone.

In one embodiment, the present invention provides a method of treating cancer by administering a nitrogen mustard alkylator drug of the invention together with a cancer treatment regimen using at least the alkylator mechlorethamine. For example, mechlorethamine is used in the combination chemotherapy regimen MOPP (mechlorethamine, Oncovin (vincristine), procarbazine, and prednisone) in patients with Hodgkin's disease and administered by intravenous bolus administration is doses 6 mg/m² on days 1 and 8 of the 28 day cycles of each course of treatment.

In one embodiment, the present invention provides a method of treating cancer by administering a nitrogen mustard alkylator drug of the invention with a cancer treatment regimen using at least the alkylator ifosfamide. Ifosfamide is used to treat pediatric and adult sarcomas, carcinomas of cervix and lung, and in combination with other drugs for germ cell testicular cancer. Ifosfamide is used as part of the ICE (ifosfamide, carboplatin, and etoposide) and RICE (rituxan and ICE) regimens for treating lymphomas (see Hardman et al., supra).

In one embodiment, the present invention provides a method of treating cancer by administering a nitrogen mustard alkylator drug of the invention with a cancer treatment regimen using at least the alkylator glufosfamide. Glufosfamide can be used for treating pancreatic cancer or Gemzar resistant pancreatic cancer, breast cancer, Morbus Hodgkin, gastrointestinal tract cancer, or as part of the GCE (glufosfamide, carboplatin, and etoposide) or RGCE (rituxan and GCE) regimen, lymphomas. (See, e.g., U.S. Pat. No. 5,622,936 and PCT Pat. Pub. No. WO 2005/076888, each of which is incorporated in their entirety herein by reference).

In one embodiment, the present invention provides a method of treating cancer by administering a nitrogen mustard alkylator drug of the invention with a cancer treatment regimen using at least an alkylator selected from the group consisting of ethylenimines and methylmelamines. In another embodiment, the ethylenimine is triethylenemelamine or thiotepa.

Thiotepa can be used to treat adenocarcinomas of the breast, ovary, and bladder, malignant lymphomas, bronchiogenic carcinomas, and Wilms' tumor. Thiotepa was used at high doses in combination chemotherapy with cyclophosphamide in patients with refractory malignancies treated with autologous bone transplantation and to treat a variety of cancers including bladder, ovarian, breast, lung, brain, and lymphomas (see, International Agency for Research on Cancer, Monographs on the Evaluation of Carcinogenic Risk of Chemicals to Humans, 1975, 9: 286, Lyon, France; International Agency for Research on Cancer, Monographs on the Evaluation of Carcinogenic Risk of Chemicals to Humans, 1990, 50: 415, Lyon, France; and MEDLINEplus, 2003, Drug Information: Thiotepa, National Library of Medicine). The methylmelamine, altretamine, is used to treat advanced ovarian cancer after failure of first round therapies.

In one embodiment, the present invention provides a method of treating cancer by administering a nitrogen mustard alkylator drug of the invention with a cancer treatment regimen using at least the alkylator melphalan, chlorambucil, or bendamustine. Melphalan is used to treat multiple myolema and can be administered orally. Chlorambucil is used to treat chronic lymphocytic leukemia and primary macroglobulinemia. Bendamustine can be used to treat hematological malignancies, such as, for example, non-Hodgkin's lymphoma, chronic lymphocytic leukemia, and multiple myeloma.

In one embodiment, the present invention provides a method of treating cancer by administering a nitrogen mustard alkylator drug of the invention with a cancer treatment regimen using at least the alkylator busulfan. Busulfan is used to treat chronic granulocytic leukemia and chronic myelogenous leukemia. High doses of busulfan can be used in combination with cyclophosphamide to treat patients with acute myelogenous leukemia before bone marrow transplantation.

In one embodiment, the present invention provides a method of treating cancer by administering a nitrogen mustard alkylator drug of the invention with a cancer treatment regimen using at least a nitrosourea alkylator. In another embodiment, the nitrosourea alkylator is carmustine. Carmustine can be used to treat Hodgkin's disease, lymphomas, myelomas, malignant astrocytomas, metastatic tumors of the brain, melanoma, and gastrointestinal tumors. In another embodiment, the nitrosourea is streptozocin which is used to treat pancreatic islet cell carcinoma.

In one embodiment, the present invention provides a method of treating cancer by administering a nitrogen mustard alkylator drug of the invention with a cancer treatment regimen using at least a triazene alkylator. In one embodiment, the triazene alkylator is dacarbazine. Dacarbazine is used to treat malignant melanoma, Hodgkin's disease, and adult sarcoma. In another embodiment, the triazene alkylator is temozolomide. Temozolomide can be used to treat malignant gliomas.

In one embodiment, the present invention provides a method of treating cancer by administering a nitrogen mustard alkylator drug of the invention with a cancer treatment regimen using at least a platinum coordination complex alkylator. In one embodiment, the platinum coordination complex alkylator is cisplatin. Cisplatin can be used to treat cancer of bladder, head and neck, endometrium, small cell carcinoma of the lung, and some neoplasms of childhood. Cisplatin alone or with cyclophosphamide is used to treat advanced ovarian cancer. Combination chemotherapy of cisplatin with bleomycin, etoposide, and vinblastine is used to treat advanced testicular cancer; and with one of paclitaxel, cyclophosphamide, or doxorubicin to treat ovarian carcinoma.

Anthracyclines useful in the practice of the methods described herein include, but are not limited to, doxorubicin (Adriamycin, Doxil, Rubex), mitoxantrone (Novantrone), idarubicin (Idamycin), valrubicin (Valstar), and epirubicin (Ellence). In accordance with the methods described herein, a nitrogen mustard alkylator drug is coadministered with an anthracycline to treat cancer. In one embodiment, the cancer is acute nonlymphocytic leukemia, Kaposi's sarcoma, prostate cancer, bladder cancer, metastatic carcinoma of the ovary, or breast cancer.

Doxorubicin has been used successfully to produce regression in disseminated neoplastic conditions such as acute lymphoblastic leukemia, acute myeloblastic leukemia, Wilm's tumor, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma. Doxorubicin is typically administered in a dose in the range of 30-75 mg/m$^2$ as a single intravenous injection administered at 21-day intervals; weekly intravenous injection at doses of 20 mg/m$^2$; or 30 mg/m$^2$ doses on each of three successive days repeated every four weeks. In accordance with the methods of the methods described herein, a nitrogen mustard alkylator drug is coadministered starting prior to and continuing after the administration of doxorubicin at such doses (or at lower doses).

Antibiotics useful in the practice of the methods described herein include, but are not limited to, dactinomycin, actinomycin D (Cosmegen), bleomycin (Blenoxane), daunorubicin (Cerubidine, DanuoXome). In accordance with the methods described herein, a nitrogen mustard alkylator drug is coadministered with an antibiotic to treat cancer. In one embodiment, the cancer is a cancer selected from the group consisting of acute lymphocytic leukemia, other leukemias, and Kaposi's sarcoma.

Aromatase inhibitors useful in the practice of the methods described herein include, but are not limited to, anastrozole (Arimidex) and letroazole (Femara). In accordance with the methods described herein, a nitrogen mustard alkylator alkylator drug is coadministered with an aromatase inhibitor to treat cancer. In one embodiment, the cancer is breast cancer.

Bisphosphonate inhibitors useful in the practice of the methods described herein include, but are not limited to, zoledronate (Zometa). In accordance with the methods described herein, a nitrogen mustard alkylator drug is coadministered with a biphosphonate inhibitor to treat cancer. In one embodiment, the cancer is a cancer selected from the group consisting of multiple myeloma, bone metastases from solid tumors, and prostate cancer.

Cyclooxygenase inhibitors useful in the practice of the methods described herein include, but are not limited to, celecoxib (Celebrex). In accordance with the methods described herein, a nitrogen mustard alkylator drug is coadministered with a cyclo-oxygenase inhibitor to treat cancer. In one embodiment, the cancer is colon cancer or a precancerous condition known as familial adenomatous polyposis.

Estrogen receptor modulators useful in the practice of the methods described herein include, but are not limited to, tamoxifen (Nolvadex) and fulvestrant (Faslodex). In accordance with the methods described herein, a nitrogen mustard alkylator drug is coadministered with an estrogen receptor modulator to treat cancer. In one embodiment, the cancer is breast cancer or the treatment is administered to prevent the occurrence or reoccurrence of breast cancer.

Folate antagonists useful in the practice of the methods described herein include, but are not limited to, methotrexate, pematrexed (alimta), and trimetrexate. In accordance with the methods described herein, a nitrogen mustard alkylator drug is co-administered with a folate antagonist to treat cancer. In one embodiment, the cancer is osteosarcoma.

Methotrexate, an antifolate drug, has been used in the treatment of gestational choriocarcinoma and in the treatment of patients with chorioadenoma destruens and hydatiform mole. It is also useful in the treatment of advanced stages of malignant lymphoma and in the treatment of advanced cases of mycosis fungoides. Methotrexate is administered as follows.

For choriocarcinoma, intramuscular injections of doses of 15 to 30 mg are administered daily for a five-day course, such courses repeated as needed with rest period of one or more weeks interposed between courses of therapy. For leukemias, twice weekly intramuscular injections are administered in doses of 30 mg/m$^2$. For mycosis fungoides, weekly intramuscular injections of doses of 50 mg or, alternatively, of 25 mg are administered twice weekly. In accordance with the methods described herein, a nitrogen mustard alkylator drug is coadministered with methotrexate administered at such doses (or at lower doses). Trimetrexate is another antifolate drug that can be coadministered with a nitrogen mustard alkylator drug.

Inorganic arsenates useful in the practice of the methods described herein include, but are not limited to, arsenic trioxide (Trisenox). In accordance with the methods described herein, a nitrogen mustard alkylator drug is coadministered with an inorganic arsenate to treat cancer. In one embodiment, the cancer is refractory acute promyelocytic leukemia (APL).

Microtubule inhibitors (as used herein, a microtubule inhibitor is any agent that interferes with the assembly or disassembly of microtubules) useful in the practice of the methods described herein include, but are not limited to, vincristine (Oncovin), vinblastine (Velban), paclitaxel (Taxol, Paxene), vinorelbine (Navelbine), docetaxel (Taxotere), epothilone B or D or a derivative of either, and discodermolide or its derivatives. In accordance with the methods described herein, a nitrogen mustard alkylator drug is coadministered with a microtubule inhibitor to treat cancer. In one embodiment, the cancer is ovarian cancer, breast cancer, non-small cell lung cancer, Kaposi's sarcoma, and metastatic cancer of breast or ovary origin. As one example, vincristine is useful in the treatment of acute leukemia. It has also been shown to be useful in combination with other oncolytic agents in the treatment of Hodgkin's disease, lymphosarcoma, reticulum-cell sarcoma, rhabdomyosarcoma, neuroblastoma, and Wilm's tumor. Vincristine is administered in weekly intravenous doses of 2 mg/m$^2$ for children and 1.4 mg/m$^2$ for adults. In accordance with the methods described herein, a nitrogen mustard alkylator drug is coadministered with vincristine administered at such doses. In one embodiment, a nitrogen mustard alkylator drug is not administered prior to treatment with a microtubule inhibitor, such as a taxane, but rather, administration of a nitrogen mustard alkylator drug is administered simultaneously with or within a few days to a week after initiation of treatment with a microtubule inhibitor.

Modifiers useful in the practice of the methods described herein include, but are not limited to, leucovorin (Wellcovorin), which is used with other drugs such as 5-fluorouracil to treat colorectal cancer. In accordance with the methods described herein, a nitrogen mustard alkylator drug is coadministered with a modifier and another anti cancer agent to treat cancer. In one embodiment, the cancer is colon cancer. In one embodiment, the modifier is N-hydroxyurea. In another such embodiment, a nitrogen mustard alkylator drug is coadministered with nitric oxide or a nitric oxide precursor, such as an organic nitrite or a spermineNONOate, to treat cancer, as the latter compounds stimulate the uptake of glucose.

Nitrosoureas useful in the practice of the methods described herein include, but are not limited to, procarbazine (Matulane), lomustine (CCNU or CeeBU), carmustine (BCNU, BiCNU, Gliadel Wafer), and estramustine (Emcyt). In accordance with the methods described herein, a nitrogen mustard alkylator drug is coadministered with a nitrosourea to treat cancer. In one embodiment, the cancer is prostate cancer or glioblastoma, including recurrent glioblastoma multiforme.

Nucleoside analogs useful in the practice of the methods described herein include, but are not limited to, mercaptopurine (6-MP, Purinethol), fluorouracil (5-FU, Adrucil), thioguanine, (6-TG, Thioguanine), cytarabine (Cytosar-U, DepoCyt), floxuridine (FUDR), fludarabine (Fludara), azacytidine (Vidaza), pentostatin (Nipent), cladribine (Leustatin, 2-CdA), gemcitabine (Gemzar), and capecitabine (Xeloda). In accordance with the methods described herein, a nitrogen mustard alkylator drug is coadministered with a nucleoside analog to treat cancer. In one embodiment, the cancer is B-cell lymphocytic leukemia (CLL), hairy cell leukemia, adenocarcinoma of the pancreas, metastatic breast cancer, non-small cell lung cancer, or metastatic colorectal carcinoma. As one example, 5-fluorouracil is an antimetabolite nucleoside analog effective in the palliative management of carcinoma of the colon, rectum, breast, stomach, and pancreas in patients who are considered incurable by surgical or other means. 5-Fluorouracil is administered in initial therapy in doses of 12 mg/m$^2$ given intravenously once daily for 4 successive days with the daily dose not exceeding 800 mg. If no toxicity is observed at any time during the course of the therapy, 6 mg/kg are given intravenously on the 6th, 8th, 10th, and 12th days. No therapy is given on the 5th, 7th, 9th, or 11th days. In poor risk patients or those who are not in an adequate nutritional state, a daily dose of 6 mg/kg is administered for three days, with the daily dose not exceeding 400 mg. If no toxicity is observed at any time during the treatment, 3 mg/kg can be given on the 5th, 7th, and 9th days. No therapy is given on the 4th, 6th, or 8th days. A sequence of injections on either schedule constitutes a course of therapy. In accordance with the methods described herein, a nitrogen mustard alkylator drug is coadministered with 5-FU administered at such doses or with the drug form xeloda with correspondingly adjusted doses. As another example, 6-thioguanine, is a nucleoside analog effective in the therapy of acute non-pymphocytic leukemias. 6-Thioguanine is orally administered in doses of about 2 mg/kg of body weight per day. The total daily dose can be given at one time. If after four weeks of dosage at this level there is no improvement, the dosage can be cautiously increased to 3 mg/kg/day. In accordance with the methods described herein, a nitrogen mustard alkylator drug is coadministered with 6-TG administered at such doses (or at lower doses).

Osteoclast inhibitors useful in the practice of the methods described herein include, but are not limited to, pamidronate (Aredia). In accordance with the methods described herein, a nitrogen mustard alkylator drug is coadministered with an osteoclast inhibitor to treat cancer. In one embodiment, the cancer is osteolytic bone metastases of breast cancer, and one or more additional anti cancer agents are also coadministered with a nitrogen mustard alkylator drug.

Platinum compounds useful in the practice of the methods described herein include, but are not limited to, cisplatin (Platinol) and carboplatin (Paraplatin). In accordance with the methods described herein, a nitrogen mustard alkylator drug is coadministered with a platinum compound to treat cancer. In one embodiment, the cancer is metastatic testicular cancer, metastatic ovarian cancer, ovarian carcinoma, and transitional cell bladder cancer. As one example, cisplatin, is useful in the palliative treatment of metastatic testicular and ovarian tumors, and for the treatment of transitional cell bladder cancer which is not amenable to surgery or radiotherapy. Cisplatin, when used for advanced bladder cancer, is administered in intravenous injections of doses of 50-70 mg/m$^2$ once every three to four weeks. In accordance with the methods described herein, a nitrogen mustard alkylator drug is coadministered with cisplatin administered at these doses (or at lower doses). One or more additional anti cancer agents can be coadministered with the platinum compound and a nitrogen mustard alkylator drug. As one example, platinol, blenoxane, and velbam can be coadministered with a nitrogen mustard alkylator drug. As another example, platinol and adriamycin can be coadministered with a nitrogen mustard alkylator drug.

Pyruvic acid plays a role in angiogenesis and other means of cancer cell proliferation. Pyruvate mimics and glycolytic inhibitors like halopyruvates, including bromopyruvate, can be used in combination with an anti angiogenic compound and a nitrogen mustard alkylator drug to treat cancer.

Retinoids useful in the practice of the methods described herein include, but are not limited to, tretinoin, ATRA (Vesanoid), alitretinoin (Panretin), and bexarotene (Targretin). In accordance with the methods described herein, a nitrogen mustard alkylator drug is coadministered with a retinoid to treat cancer. In one embodiment, the cancer is a cancer selected from the group consisting of APL, Kaposi's sarcoma, and T-cell lymphoma.

Topoisomerase 1 inhibitors useful in the practice of the methods described herein include, but are not limited to, topotecan (Hycamtin) and irinotecan (Camptostar). In accordance with the methods described herein, a nitrogen mustard alkylator drug is coadministered with a topoisomerase 1 inhibitor to treat cancer. In one embodiment, the cancer is metastatic carcinoma of the ovary, colon, or rectum, or small cell lung cancer. As noted above, however, in one embodiment of the methods described herein, administration of a nitrogen mustard alkylator drug either precedes or follows, or both, administration of a topoisomerase 1 inhibitor but is not administered concurrently therewith.

Topoisomerase 2 inhibitors useful in the practice of the methods described herein include, but are not limited to, etoposide, VP-16 (Vepesid), teniposide, VM-26 (Vumon), and etoposide phosphate (Etopophos). In accordance with the methods described herein, a nitrogen mustard alkylator drug is coadministered with a topoisomerase 2 inhibitor to treat cancer. In one embodiment, the cancer is a cancer selected from the group consisting of refractory testicular tumors, refractory acute lymphoblastic leukemia (ALL), and small cell lung cancer. As noted above, however, in one embodiment of the methods described herein, administration of a nitrogen mustard alkylator drug either precedes or follows, or both, administration of a topoisomerase 2 inhibitor but is not administered concurrently therewith.

Tyrosine kinase inhibitors useful in the practice of the methods described herein include, but are not limited to, imatinib (Gleevec). In accordance with the methods described herein, a nitrogen mustard alkylator drug is coadministered with a tyrosine kinase inhibitor to treat cancer. In one embodiment, the cancer is CML or a metastatic or unresectable malignant gastrointestinal stromal tumor.

Treatment of Hyperproliferative Diseases

In some embodiments of the invention, a compound of the present invention is administered to treat a hyperproliferative disease other than cancer selected from the group consisting of psoriasis, multiple sclerosis, rheumatoid arthritis, restenosis, and benign prostatic hyperplasia. In one embodiment, the hyperpriliferative disease treated is psoriasis, a disease characterized by the cellular hyperproliferation of keratinocytes which builds up on the skin to form elevated, scaly lesions. In another embodiment, the hyperproliferative disease treated is multiple sclerosis, a disease characterized by progressive demyelination in the brain. In another embodiment, the hyperproliferative diseases treated is rheumatoid arthritis, a multisystem chronic, relapsing, inflammatory disease that can lead to destruction and ankylosis of joints affected. In another embodiment, the compounds of the present invention are administered to prevent a hyperproliferative disease resulting from cellular proliferation on a prosthesis implanted in a subject by coating the prosthesis with a composition containing a compound of the present invention. In another embodiment, the hyperproliferative disease treated is benign prostatic hyperplasia, a disease in which prostate epithelial cells grow abnormally and thereby block urine flow.

The invention, having been described in summary and in detail, is illustrated but not limited by the Examples below, which describe methods for synthesizing hypoxia activated drug compounds of this invention and pharmaceutical formulations of this invention, and demonstrate the efficacy of the hypoxia activated drug compounds of this invention.

III. Examples

The following abbreviations are used in the following examples and in the disclosure:

Ac: acetyl; Bn: benzyl; Boc: tertiarybutyloxycarbonyl; DCM: dichloromethane; DIAD: diisopropyl azodicarboxylate; DIEA: diisopropyl ethyl amine; DMF: dimethyl formamide; Et: ethyl; EtOAc: ethyl acetate; EtOH: ethyl alcohol; Et$_2$O: diethyl ether; HATU: the peptide coupling agent O-(7-Azabenzotriazol-1-yl)-N,N,N',N'-tetramethyluronium hexafluorophosphate; KO$^t$Bu: potassium tertiary butoxide; MCPBA: meta chloro peroxybenzoic acid; Me: methyl; μL: micro liter; mL: milli liter; MsCl: methanesulfonyl chloride; Ph: phenyl; TEA: triethyl amine; MeCN: acetonitrile; THF: tetrahydrofuran; RT or rt: room temperature; R$_f$: retention factor; TFA: trifluoroacetic acid; and TBDMS: teriarybutyldimethylsilyl.

Example 1

Synthesizing Hypoxia Activated Drug Compounds of the Present Invention

A. TH 1104

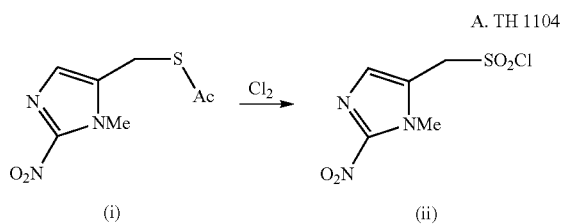

To a biphasic solution of compound (i) (prepared by reacting the corresponding bromide and KSAc) in DCM (10 mL) and water (2.1 mL) was bubbled Cl$_2$ at 0° C. for 10 min. Subsequently, air was bubbled through the reaction mixture to remove dissolved Cl$_2$. The reaction mixture was poured in to EtOAc and washed with water and brine. The EtOAc layer was dried over MgSO$_4$, filtered, the filtrate concentrated and coevaporated with toluene to a final volume of about 2 mL. DCM (1 mL) was added to it and this solution containing compound (ii) was used for the reactions described herein.

Other such sulfonyl chloride compounds, such as for example,

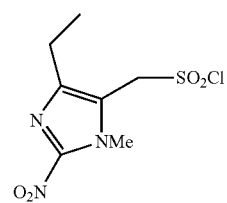

were synthesized similarly starting from the corresponding bromide (or chloride),

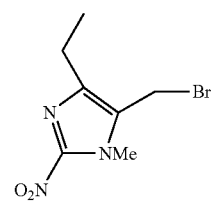

that was obtained from the corresponding alcohol as described in PCT Pat. Pub. No. WO 08/151,253.

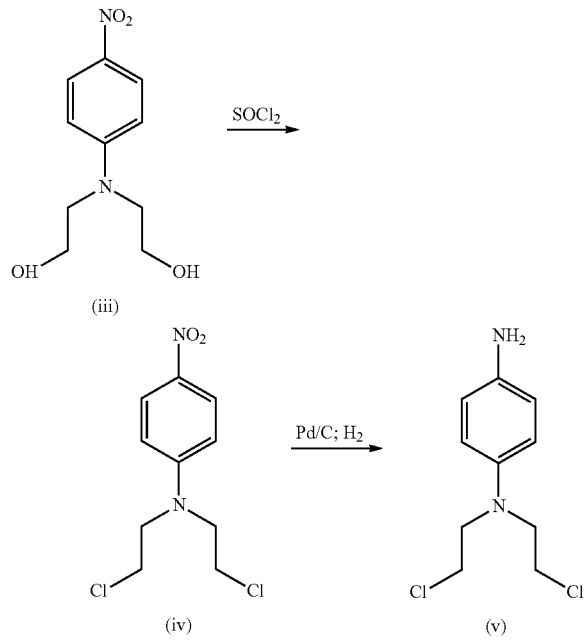

To a suspension of compound (iii) (2 g) in dichloromethane (DCM, 20 mL) maintained at 0° C. was added pyridine (1.3 mL) and, slowly, $SOCl_2$ (1.5 mL). The reaction mixture was warmed at 60° C. for 1 h, poured into ice, and extracted with DCM. The DCM layer was separated, dried, and volatiles removed to yield 2.2 g of compound iv whose structure was confirmed by $^1$H-NMR and which was used in the next reaction without further purification.

To a solution of compound iv (2.2 g) in EtOH (50 mL) was added Pd/C (300 mg) and the mixture stirred in presence of hydrogen at room temperature (rt) for 2 h. The mixture was filtered through a celite pad, volatiles removed from the filtrate, to yield a residue. The residue was dissolved in EtOH (40 mL) and $Et_2O$ (80 mL) and acidified with 12M aqueous HCl (HCl/dioxane was also used). The precipitated solid was filtered, the residue washed with $EtOH/Et_2O$ (1:2). Volatiles were removed from the residue to yield 1.5 g of the hydrochloride salt of compound v whose structure was confirmed by $^1$H-NMR and which was used without further purification for the synthesis of various hypoxia activated drug compound of the present invention as described herein.

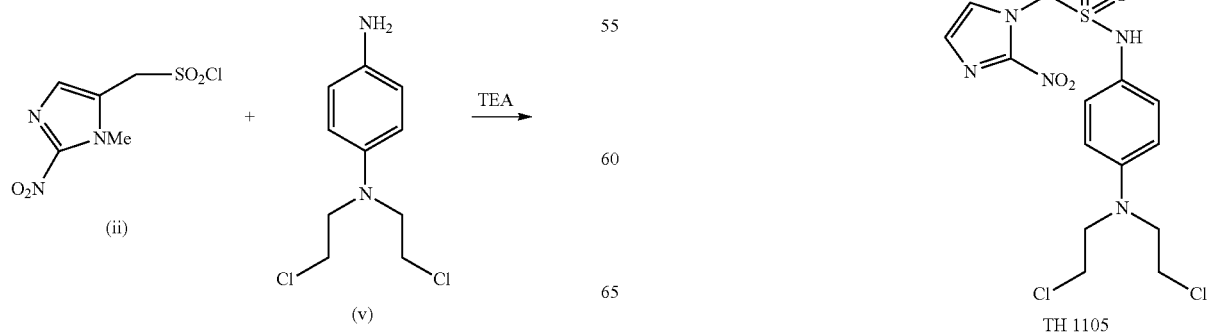

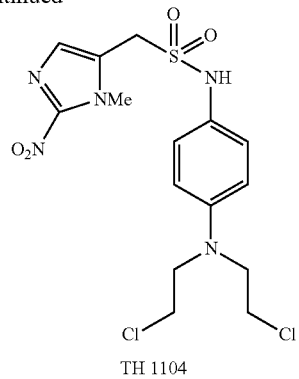

TH 1104

To a solution of compound v (143 mg) in DCM (4 mL) was added triethyl amine (TEA, 130 µL) followed by the addition of the solution of compound (II) (synthesized as described above). The reaction mixture was stirred at rt for 2 h. Volatiles were removed and the residue was separated by column chromatography using EtOAc/Hexane (1:1) as eluent to yield 130 mg of TH 1104.

B. TH 1105

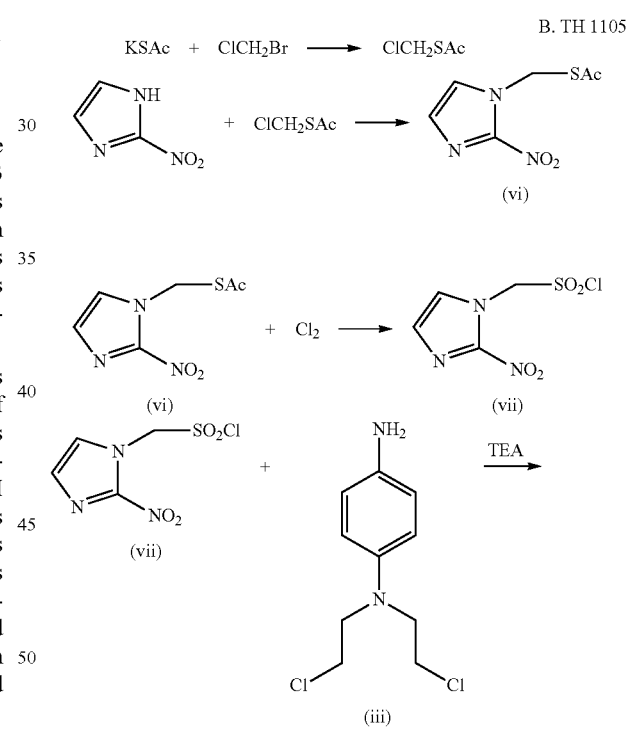

TH 1105

To a suspension of KSAc (4.6 g) in MeCN (200 mL) placed under argon was added BrCH$_2$Cl (12 mL) at room temperature (rt) and stirred for 12 h. The reaction mixture was filtered, the filtrate concentrated to yield a residue. The residue was diluted with ether, filtered and concentrated to yield the volatile chloromethylthioacetate.

To a solution of the chloromethylthioacetate in MeCN (100 mL) was added 2-nitroimidazole (3 g), NaI (1 g) and diisopropylethyl amine (DIEA) and refluxed. A precipitate formed after 3 h. Additional DIEA (3 mL) was added to the reaction mixture and refluxed for 4 h. Volatiles were removed, EtOAc (300 mL) added to the residue, and the ensuing mixture filtered. The filtrate was washed with water, 1M aqueous citric acid, brine, and concentrated to yield a residue. The residue was separated by column chromatography using 0-90% EtOAc/Hexane as eluent to yield 1-thioacetylmethyl-2-nitroimidazole (vi, 3.15 g) that was chlorinated as described above in Example 1A to yield compound vii.

To a mixture of compound (iii) (200 mg) and triethyl amine (TEA, 190 µL) in DCM (6 mL) was added at 0° C. 0.68 mmol of compound vii. The reaction mixture was warmed up to rt and adsorbed on silica gel. Volatiles were removed from the silica gel and separated by column chromatography using EtOAc/Hexane (1:1) as eluent to yield 120 mg of TH 1105.

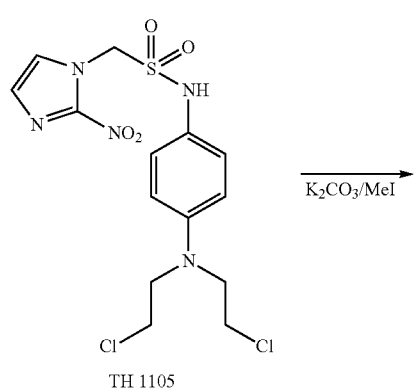

To a solution of TH 1105 (50 mg) in dimethyl formamide (DMF, 3 mL) was added K$_2$CO$_3$ (18 mg) and MeI (32 µl). The reaction mixture was stirred overnight and poured in to brine and extracted twice with EtOAC. The combined EtOAc layers were washed with brine, dried, and volatiles removed to yield a residue. The residue was separated by column chromatography on silica gel using EtOAc/Hexane (1:1) as eluent to yield 30 mg of TH 1107.

D. TH 1103

To a solution of 2-nitrothiophene (12.9 mg) and compound viii, prepared according to the method described in Example G, 36 mg) in tetrahydrofuran (THF, 1 mL) at −50° C. was added a 1 M solution of KOtBu (0.3 mL) in THF and the dark colored solution stirred for 30 min. Acetic acid (16 µL) was added to the reaction mixture, the reaction mixture adsorbed on silica gel, volatiles removed, and the silica gel portion separated by column chromatography using 0-25% of 10% acetone/DCM—50% hexanes/DCM and re-separated using 0-10% of 10% acetone/DCM—50% hexanes/DCM as eluent to yield 25 mg of TH 1103.

TH 1131 was synthesized starting from 2-methyl-5-nitrothiophene (18 mg) and compound viii (46 mg) employing the method used for synthesizing TH 1103.

E. TH 1120

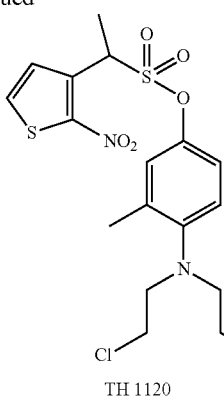

TH 1120

To a solution of TH 1103 (26.8 mg) and MeI (37 µL) in DMF (0.6 mL) was added drop wise a 1 M solution of KOtBu (0.12 mL) in THF and stirred at rt for 3 h. The reaction mixture was diluted with water and extracted with EtOAc. The EtOAc layer was washed with water and brine, dried, and volatiles removed to yield a residue that was separated by preparative thick layer chromatography using 25% EtOAc/Hexane to yield 14 mg of TH 1120.

F. TH 1126

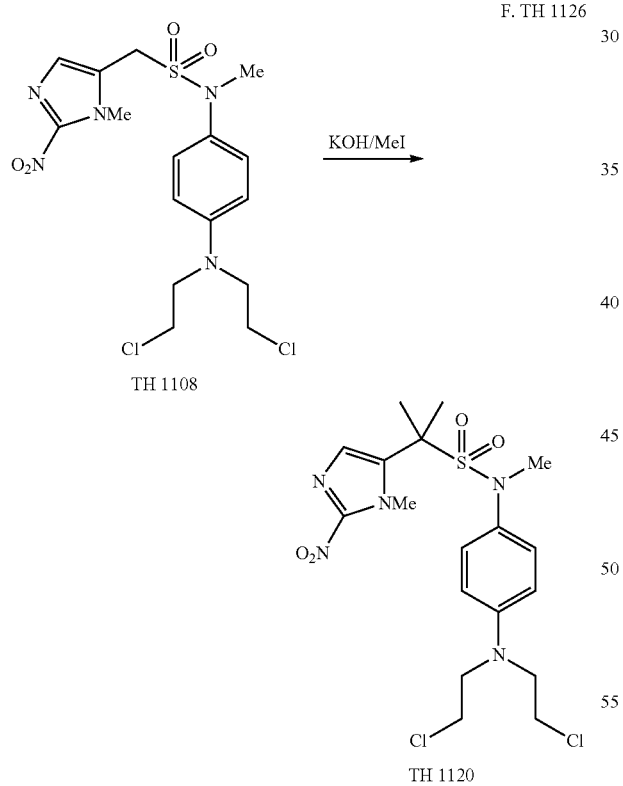

TH 1126 was synthesized from TH 1108; TH 1108 was synthesized by alkylating TH 1103 according to the method described in Example 1C. To a solution of TH 1108 (28 mg) in DMF (2 mL) was added and MeI (0.2 mL) and KOH (40 mg) and stirred at 40° C. for about 16 h. The reaction mixture was diluted with water and extracted with EtOAc. The EtOAc layer was washed with water and brine, dried, and volatiles removed to yield a residue that was separated by preparative thick layer chromatography using 0-60% EtOAc/Hexane to yield 14 mg of TH 1126.

TH 1127 (14 mg) was synthesized by reacting TH 1107 (28 mg), MeI (0.15 mL), KOH (41 mg), and DMF (2 mL) employing the method described in Example 1F. TH 1132 (5 mg) was synthesized from TH 1131 (30 mg), MeI (0.2 mL), KOH (41 mg), and DMF (1 mL) employing the method described in Example 1F. TH 1131 was synthesized following the method described in Example 1D and using the appropriate methylnitrothiphene.

Scheme I.

G. TH-1152

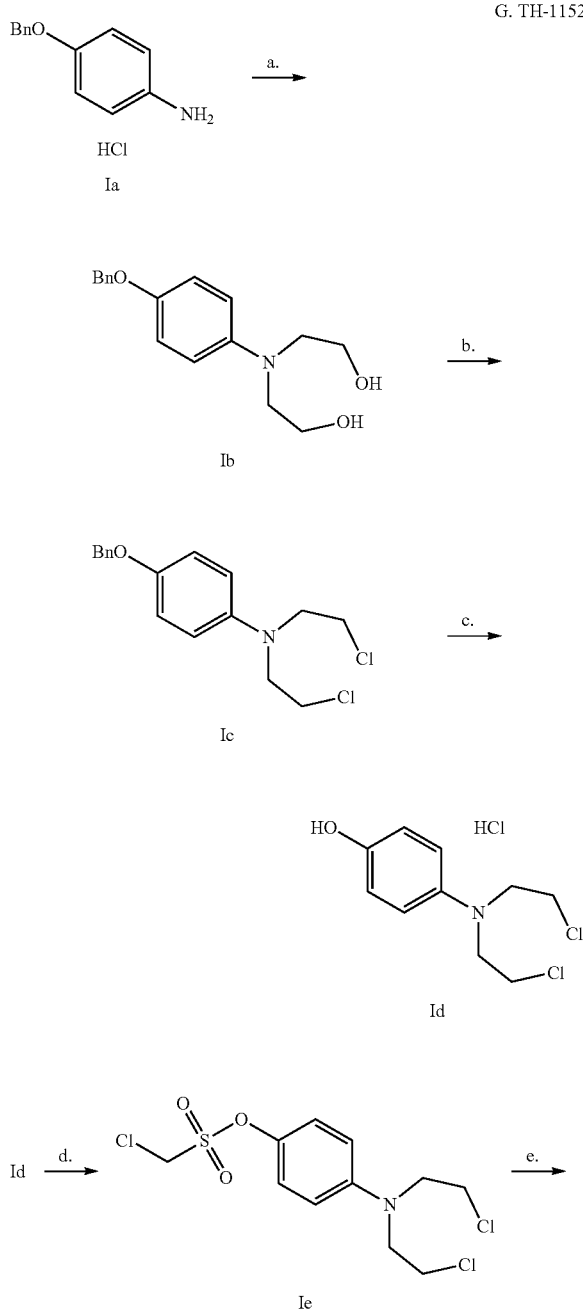

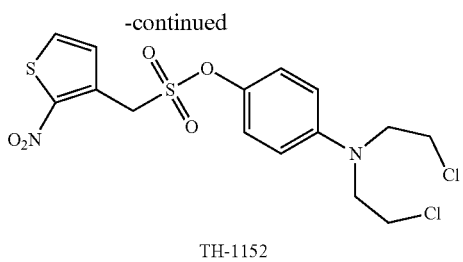

TH-1152 a. i. MeOH, aq. NaOH ii. ethylene oxide, HOAc, H₂O
b. POCl₃
c. H₂, Pd/C EtOAc, EtOH, aq. HCl
d. chloromethylsulfonyl chloride, TEA, DCM
e. 2-nitrothiophene t-BuOK, THF.

A solution of 4-benzyloxyaniline hydrochloride (compound Ia, 12 g) in MeOH (200 mL) was treated with aqueous NaOH (2.04 g in 80 mL deionized water) and the resulting clear solution was concentrated to dryness to provide a residue of crude aniline free base. A suspension of the crude aniline residue in 1:1 AcOH/deionized water (80 mL), in a pressure tube maintained at 0° C., was treated with liquid ethylene oxide (18 g) condensed at −78° C. The pressure tube was sealed and the reaction mixture allowed to warm up to room temperature (RT). The reaction mixture was stirred at RT for 48 h and cooled. The precipitate was collected by filtration and washed twice with water and dried to furnish compound Ib (8.6 g). The filtrate was evaporated to dryness and purified by silica gel chromatography (0-100% EtOAc/Hexanes) to provide additional product (2.6 g).

A solution of compound Ib (8.2 g) in POCl₃ (40 mL) was heated to 100° C. for 1 h. Excess POCl₃ was removed by evaporation then the remaining mixture poured into ice, cautiously neutralized with solid NaHCO₃ and extracted with EtOAc. The combined organic layers were washed with saturated aq. NaHCO₃, brine, dried and concentrated until crystallization occurred. The solid crystalline product was collected by filtration and washed with EtOAc/hexanes. Additional material was obtained by evaporation of the filtrate followed by purification of the residue by silica gel chromatography 0-60% EtOAc/Hexanes to provide combined compound Ic (8 g).

A solution of compound Ic (8 g) in EtOH (100 mL), EtOAc (100 mL) and conc. HCl (2 mL), and 10% Pd/C was stirred under H₂ atmosphere for 3 h. The reaction mixture was filtered through a pad of celite, treated with conc. HCl (5 mL), and evaporated to dryness and further dried under high vacuum to yield compound Id (7 g).

To a 0° C. solution of compound Id (7 g) and TEA (9 mL) in DCM (50 mL) was slowly added a solution of chloromethylsulfonyl chloride, the reaction mixture was allowed to warm to RT, and stirred for 2 h. The reaction mixture was poured into brine and the organic layer separated, dried, volatiles removed and the residue separated by column chromatography using 0-80% EtOAc/Hexanes to provide compound Ie (7.8 g).

To a −50° C. solution of 2-nitrothiophene (3.4 g) and compound Ie (7.8 g) in DCM (THF, 100 mL) was added a 1 M solution of KOtBu in THF (8.0 mL), dropwise, over 30 minutes, and the reaction mixture stirred for 30 min. Acetic acid (2.6 mL) was added to the reaction mixture, the reaction mixture adsorbed on silica gel, volatiles removed, and the silica gel portion separated by column chromatography using 0-100% EtOAc/Hexanes to provide TH-1152 (7.6 g). ¹H NMR (400 MHz, CDCl₃) δ 7.57 (d, J=5.5 Hz, 1H), 7.36 (d, J=5.6 Hz, 1H), 7.08 (d, J=9.2 Hz, 2H), 6.63 (d, J=9.2 Hz, 2H), 5.13 (s, 2H), 3.73 (t, J=7.0 Hz, 4H), 3.62 (t, J=6.7 Hz, 4H).

H. TH-1192

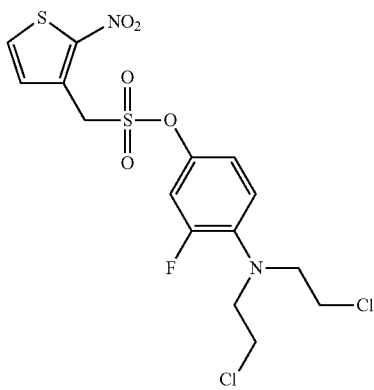

A solution of 2-fluoro-4-hydroxyaniline hydrochloride (3 g) in MeOH (50 mL) was treated with aqueous NaOH (0.74 g in 10 mL deionized water) and the resulting clear solution was concentrated to dryness to provide a residue of crude aniline free base. A 0° C. solution of the crude aniline residue in 1:1 AcOH/deionized water (32 mL) in a pressure tube was treated with liquid ethylene oxide condensed at −78° C. (7.8 g), the tube was sealed, and the reaction mixture allowed to warm up to RT. The reaction mixture was stirred at RT 48 h then cooled, evaporated to dryness and purified by silica gel chromatography (0-7% MeOH/DCM) to provide N,N-bis-(2-hydroxyethyl)-2-fluoro-4-hydroxyaniline (2 g) as a grey powder.

To a solution of N,N-bis-(2-hydroxyethyl)-2-fluoro-4-hydroxyaniline (2 g) and KOH (0.64 g, 10.0 mmole) in EtOH (13 mL) was added BnBr (1.1 mL, 9.1 mmole) and the reaction mixture stirred at reflux for 3 h. The reaction mixture was cooled, evaporated to in dryness and purified by silica gel chromatography (0-7% MeOH/DCM) to provide N,N-bis-(2-hydroxyethyl)-2-fluoro-4-benzyloxyaniline (2.26 g) as a yellow syrup.

The synthesis of TH-1192 from the intermediate N,N-bis-(2-hydroxyethyl)-2-fluoro-4-benzyloxyaniline was performed in the same way as that of TH-1152. ¹H NMR (400 MHz, CDCl₃) δ 7.59 (d, J=5.5 Hz, 1H), 7.32 (d, J=5.5 Hz, 1H), 7.22 (dd, J=8.8, 5.6 Hz, 1H), 7.07-6.94 (m, 2H), 5.27 (s, 2H), 3.52 (s, 8H).

Scheme II.

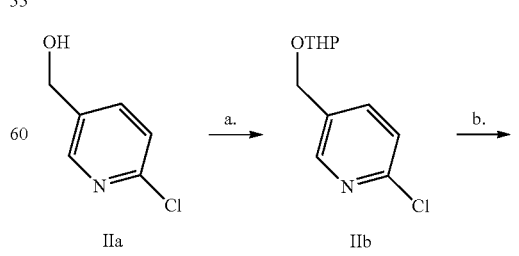

I. TH-1315

-continued

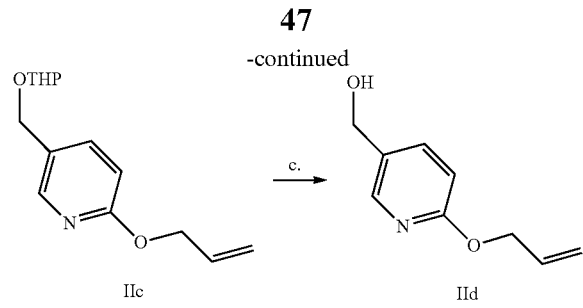

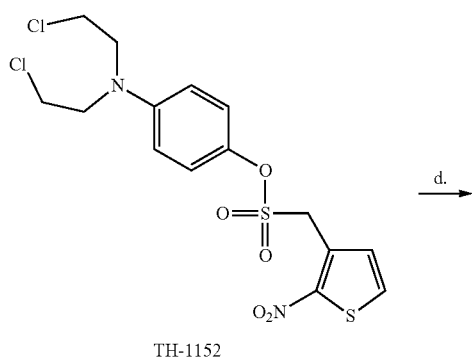

TH-1152

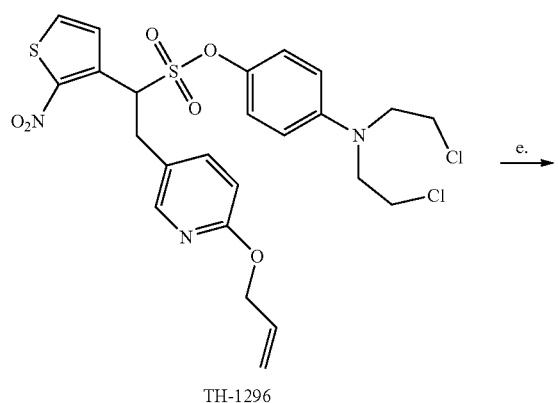

TH-1296

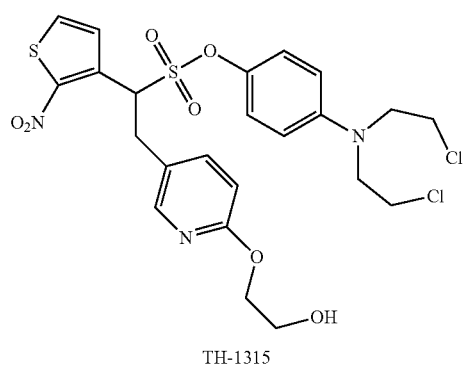

TH-1315

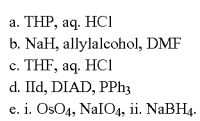

a. THP, aq. HCl
b. NaH, allylalcohol, DMF
c. THF, aq. HCl
d. IId, DIAD, PPh₃
e. i. OsO₄, NaIO₄, ii. NaBH₄.

To a solution of 6-chloro-3-pyridinemethanol (2 g, 13.5 mmol) in $Et_2O$ (40 mL) was added 3,4-dihydropyridone (1.6 mL) followed by 2 drops of conc. HCl. The reaction mixture was stirred for 24 h. Additional 3,4-dihydropyridone (3 mL) followed by 3 drops conc. HCl was added and the reaction mixture was stirred for 48 h. The reaction mixture was neutralized with solid KOH pellets, filtered, and volatiles removed. The residue was purified by column chromatography using 0-30% EtOAc/Hexanes to provide compound IIb (3 g).

To a suspension of pentane washed sodium hydride (368 mg, 15.4 mmol) in DMF (20 mL) was added allyl alcohol (1.05 mL, 15.4 mmol), dropwise, and the reaction mixture stirred for 15 min until a homogenous solution resulted. A solution of IIb (1 g, 4.4 mmol) in DMF (10 mL) was added to the reaction mixture which was heated to 90° C. for 2 h. The reaction mixture was diluted with EtOAc (150 mL) and the organic layer washed with 1:1 water/saturated $NaHCO_3$ (2×50 mL), water (2×100 mL), brine, dried over $Na_2SO_4$ and volatiles removed. The residue was purified by column chromatography using 0-20% EtOAc/Hexanes to provide compound IIc (0.9 g).

To a 75° C. solution of IIc (0.84 g, 13.5 mmol) in 75% aq. THF (100 mL) was added conc. HCl (5 mL) and stirred for 2.5 h. The reaction mixture was cooled to RT and neutralized with solid $NaHCO_3$ and the volume reduced to 10 mL. The aq. layer was washed with DCM, the organic phase dried over $Na_2SO_4$ and volatiles removed. The residue was purified by column chromatography using 0-60% EtOAc/Hexanes to provide compound IId as a clear oil (0.45 g).

To a 0° C. solution of IId (1.7 g, 10.3 mmol), TH-1152 (2.3 g, 5.33 mmol), and $PPh_3$ (2.7 g, 10.3 mmol), in anhydrous toluene (25 mL) was added DIAD (2.1 mL, 10.3 mmol), dropwise, the reaction mixture was stirred for 5 min, allowed to come to RT and stirred for 3 h. Silica was added to the reaction mixture and volatiles removed. The residue was purified by column chromatography using 0-40% EtOAc/Hexanes followed by a second chromatography (2:1 Hexanes/DCM to 5:45:50 acetone/DCM/Hexanes) to provide TH-1296 as a yellow oil (2.52 g).

To a 40° C. solution of TH-1296 (2.52 g, 4.3 mmol) in 66% aq. dioxane (200 mL) was added 4% aq. $OsO_4$ (2.7 mL) dropwise, followed by 80 mL ddi water and $NaIO_4$ (2.75 g, 12.9 mmol) the reaction mixture was stirred for 1.5 h. Dioxane was removed from the reaction mixture. The aq. layer was washed with DCM (4×50 mL), the organic phase dried over $Na_2SO_4$ and volatiles removed then co-evaporated (2×24 mL) EtOH. The residue was dissolved in EtOH (80 mL), cooled to 0° C., and $NaBH_4$ (162 mg, 4.3 mmol) was added in portions. The reaction mixture was stirred for 30 min, quenched with AcOH (0.5 mL) and silica gel, and the solvents were removed. The residue was purified by column chromatography (2:1 Hexanes/DCM to 10:90 MeOH/DCM) to provide TH-1315 as a yellow foam (1.78 g). $^1H$ NMR (400 MHz, $CDCl_3$) δ 7.74 (d, J=2.2 Hz, 1H), 7.55 (dt, J=18.4, 9.2 Hz, 2H), 7.35 (dd, J=8.5, 2.4 Hz, 1H), 6.99 (d, J=9.2 Hz, 2H), 6.67 (d, J=8.5 Hz, 1H), 6.60 (d, J=9.2 Hz, 2H), 6.18 (dd, J=10.8, 4.5 Hz, 1H), 4.42-4.35 (m, 2H), 3.90 (s, 2H), 3.81-3.67 (m, 5H), 3.61 (t, J=6.7 Hz, 4H), 3.33 (dd, J=14.2, 10.9 Hz, 2H).

J. TH-1305

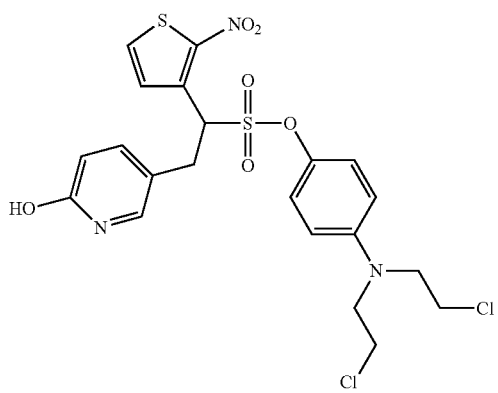

To a solution of TH-1296 (622 mg, 10.6 mmol) and Pd(PPh$_3$)$_4$ (180 mg) under argon was added a solution of triethylsilane (6 mL) in DCE (60 mL) and the reaction mixture was stirred for 45 min. Methanol (10 mL) and silica were added to the reaction mixture followed by 1M aq. HCl (50 µL) and the reaction mixture stirred for 15 min. Solvents were removed and the residue was purified by column chromatography (1:1 Hexanes/DCM to 10:90 MeOH/DCM) to provide TH-1305 as a tan solid (330 mg). $^1$H NMR (400 MHz, CDCl$_3$) δ 13.00 (Br s, 0.5H), 7.59 (d, J=5.6 Hz, 1H), 7.48 (d, J=5.7 Hz, 1H), 7.25-7.22 (m, 1H), 7.02 (d, J=2.0 Hz, 1H), 6.96 (d, J=9.2 Hz, 2H), 6.60 (d, J=9.2 Hz, 2H), 6.46 (d, J=9.4 Hz, 1H), 6.10 (dd, J=10.3, 4.8 Hz, 1H), 3.71 (t, J=6.8 Hz, 4H), 3.64-3.56 (m, 5H), 3.15 (dd, J=14.4, 10.4 Hz, 1H).

K. TH-1255

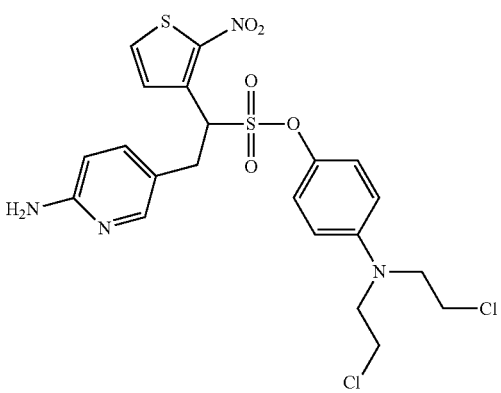

2-(Boc-amino)-5-pyridinemethanol (3.8 g, 17.1 mmol), TH-1152 (5 g, 11.4 mmol), and PPh$_3$ (5.97 g, 22.8 mmol), were co-evaporated from anhydrous toluene and dried under high vacuum for 10 min. The residue was taken up in THF (50 mL), DIAD (4.5 mL, 0.91 mmol) was added, the reaction mixture was stirred for 1 h, diluted with EtOAc, and washed with water and brine. The organic layer was dried over Na$_2$SO$_4$ and volatiles removed. The residue was purified by column chromatography using 0-60% EtOAc/Hexanes to provide crude TH-1254.

To a 0° C. solution of TH-1254 in DCM (15 mL) was added TFA (20 mL) the reaction mixture was stirred overnight at RT and volatiles removed. The residue was diluted with EtOAc and washed with saturated NaHCO$_3$ (×2) and brine (×2) dried over Na$_2$SO$_4$ and volatiles removed. The residue was purified by column chromatography using 0-100% EtOAc/Hexanes to provide TH-1255 as a yellow solid (6 g). $^1$H NMR (400 MHz, CDCl$_3$) δ 7.65 (d, J=2.0 Hz, 1H), 7.54 (q, J=5.7 Hz, 2H), 7.18 (dd, J=8.4, 2.4 Hz, 1H), 6.99 (d, J=9.2 Hz, 2H), 6.60 (d, J=9.2 Hz, 2H), 6.37 (d, J=8.4 Hz, 1H), 6.16 (dd, J=11.0, 4.4 Hz, 1H), 4.35 (s, 2H), 3.77-3.67 (m, 5H), 3.61 (t, J=6.7 Hz, 4H), 3.26 (dd, J=14.1, 11.1 Hz, 1H).

L. TH-1330

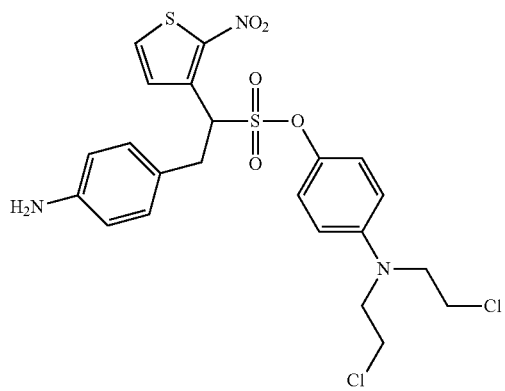

The synthesis of TH-1330 was performed as that of TH-1255 upon appropriate substitution of starting material. $^1$H NMR (400 MHz, CDCl$_3$) δ 7.52 (dd, J=9.2, 5.2 Hz, 1H), 6.99 (d, J=9.2 Hz, 2H), 6.92 (d, J=8.0 Hz, 2H), 6.79 (d, J=8.0 Hz, 2H), 6.61 (d, J=9.2 Hz, 2H), 6.21 (dd, J=11.2, 4.4 Hz, 1H), 6.00-5.68 (m, 3H), 3.85-3.58 (m, 1H), 3.70 (t, J=6.4 Hz, 4H), 3.60 (t, J=6.4 Hz, 4H), 3.40-3.27 (m, 1H).

Scheme III.

M. TH-1442

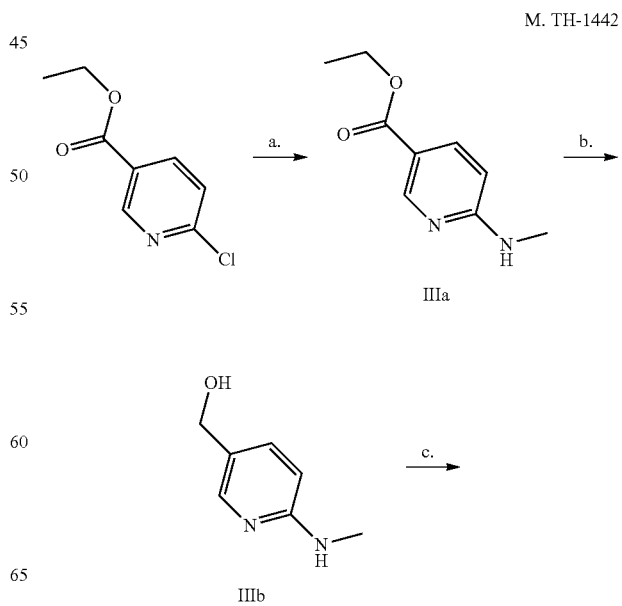

-continued

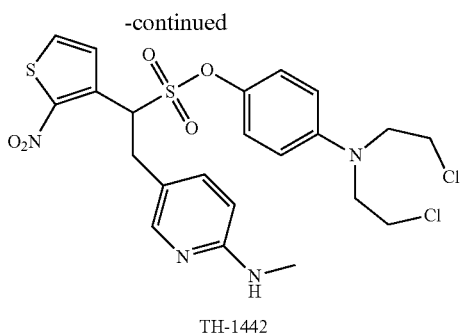

TH-1442 a. MeNH₂, EtOH, DMF
b. LiAlH₄
c. TH-1152, DIAD, PPh₃.

To a solution of ethyl-6-chloro-3-pyridinecarboxylate (2 g) in DMF (20 mL) was added MeNH₂ (2.0 mL, 33% in EtOH), the vessel sealed, and the reaction mixture was heated to 50° C. and stirred for 2 h. Additional MeNH₂ (2.0 mL, 33% in EtOH) was added and stirring continued for 24 h. The reaction mixture was diluted with EtOAc, the organic layer washed with saturated NaHCO₃, water, brine, dried over Na₂SO₄ and volatiles removed. The residue was purified by column chromatography using 0-40% EtOAc/Hexanes to provide compound IIIa (715 mg).

To a 0° C. solution of IIIa (1.5 g) in THF (25 mL) was added lithium aluminum hydride (6.1 mL, 2M in THF) dropwise stirred for 40' 5 mL MeOH was added cautiously followed by silica gel, solvents were removed. The residue was purified by column chromatography using 0-20% MeOH/DCM to provide compound IIIb as a colorless solid (1.3 g).

To a solution of IIIb (32 mg, 0.23 mmol), TH-1152 (100 mg, 0.23 mmol), and PPh₃ (120 mg, 0.44 mmol) in THF (3 mL), DIAD (90 μL, 0.44 mmol) was added and the reaction mixture was stirred 10' diluted with EtOAc and washed with water and brine, dried over Na₂SO₄ and volatiles removed. The residue was purified by column chromatography using 0-100% EtOAc/Hexanes followed by a second chromatography 0 to 70% acetone/toluene to provide TH-1442 (80 mg). ¹H NMR (400 MHz, CDCl₃) δ 7.66 (d, J=2.0 Hz, 1H), 7.54-7.50 (m, 2H), 7.30-7.21 (m, 2H), 7.20-7.11 (m, 3H), 7.00 (d, J=9.2 Hz, 2H), 6.59 (d, J=9.2 Hz, 2H), 6.24 (d, J=8.6 Hz, 1H), 6.16 (dd, J=11.1, 4.3 Hz, 1H), 4.53 (dd, J=9.7, 4.6 Hz, 1H), 3.74-3.66 (m, 5H), 3.60 (t, J=6.7 Hz, 4H), 3.25 (dd, J=14.1, 11.2 Hz, 1H), 2.83 (d, J=5.2 Hz, 3H).

N. TH-1331

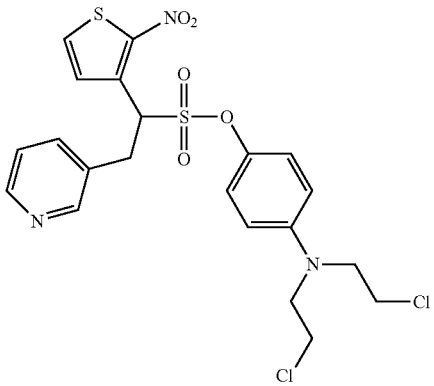

To a 0° C. solution of 3-pyridylcarbinol (115 μL, 1.2 mmol), TH-1152 (350 mg, 0.8 mmol) and PPh₃ (314 mg, 1.2 mmol), in anhydrous toluene (4 mL) was added DIAD (242 μL, 1.2 mmol), dropwise, and the reaction mixture was stirred for 10 min. The reaction mixture was allowed to come to RT and stirred for 3 h, silica was added and volatiles removed. The residue was purified by column chromatography using 0-85% EtOAc/Hexanes followed by a second chromatography (2:1 Hexanes/DCM to 20% acetone/DCM), and a third column (0-50% acetone toluene) to provide TH-1331 as a yellow oil (305 mg). ¹H NMR (400 MHz, CDCl₃) δ 8.45 (dd, J=4.7, 1.3 Hz, 1H), 8.26 (d, J=1.8 Hz, 1H), 7.57 (dd, J=13.1, 5.7 Hz, 2H), 7.46 (d, J=7.9 Hz, 1H), 7.18 (dd, J=7.8, 4.8 Hz, 1H), 6.98 (d, J=9.2 Hz, 2H), 6.60 (d, J=9.2 Hz, 2H), 6.24 (dd, J=10.8, 4.6 Hz, 1H), 3.86 (dd, J=14.1, 4.6 Hz, 1H), 3.71 (t, J=6.8 Hz, 4H), 3.61 (t, J=6.7 Hz, 4H), 3.40 (dd, J=14.0, 10.9 Hz, 1H).

O. TH-1365

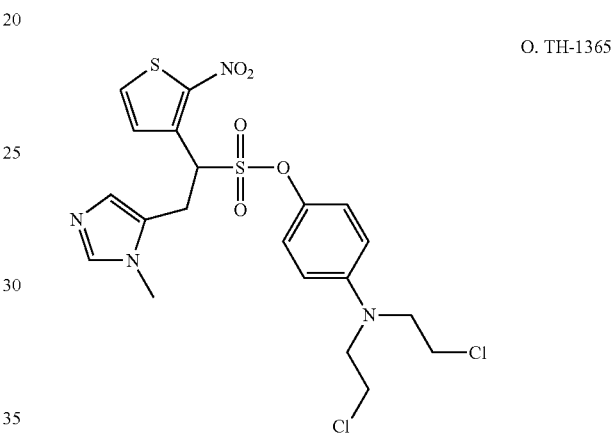

To a 0° C. suspension of 5-hydroxymethyl-1-methyl-1H-imidazole (38 mg, 0.34 mmol), TH-1152 (100 mg, 0.23 mmol) and PPh₃ (120 mg, 0.46 mmol), in anhydrous toluene (5 mL) was added DIAD (90 μL, 0.46 mmol), dropwise. The reaction mixture was stirred for 5 min, allowed to come to RT and stirred overnight. Silica was added to the reaction mixture and volatiles removed. The residue was purified by column chromatography using 0-100% acetone/toluene to provide TH-1365 (50 mg). ¹H NMR (400 MHz, CDCl₃) δ 7.59 (d, J=5.7 Hz, 1H), 7.50 (d, J=5.7 Hz, 1H), 7.36 (s, 1H), 6.86 (d, J=9.2 Hz, 2H), 6.59 (d, J=9.2 Hz, 2H), 7.50 (s, 1H), 6.16 (dd, J=11.1, 4.3 Hz, 1H), 3.77-3.68 (m, 5H), 3.64-3.58 (m, 7H), 3.51-3.47 (m, 1H).

Scheme IV.

P. TH-1456

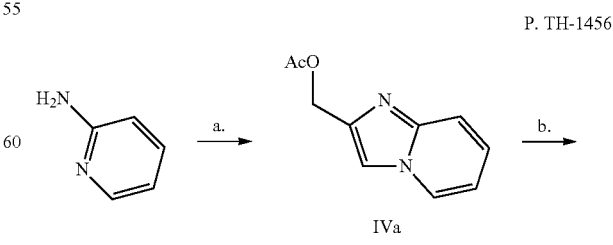

IVa

-continued

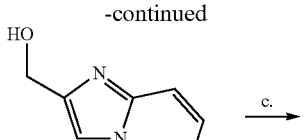

IVb

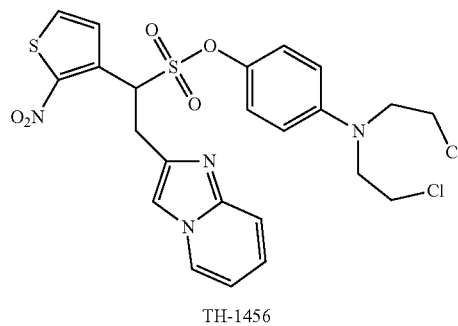

TH-1456 a. 3-acetoxychloroacetone, NaI, MeCN
b. MeOH, MeONa
c. TH-1152, DIAD, PPh₃

To a solution of 3-acetoxychloroacetone (1 g, 6.6 mmol) and NaI (749 mg, 5.0 mmol) in MeCN (100 mL) was slowly added 2-aminopyridine (1.9 g, 19.9 mmol) the reaction mixture was allowed to warm to 80° C. and stirred for 20 h. The reaction mixture was taken up on silica, volatiles removed and the residue separated by column chromatography (2:1 Hexanes/DCM to 20% acetone/DCM) to yield the crude intermediate. To the crude intermediate in MeOH (40 mL) was added a catalytic amount of NaOMe (50 mg) and stirred for 45 min. The reaction mixture was taken up on silica, volatiles removed and the residue separated by column chromatography (2:1 Hexanes/DCM to 10% MeOH/DCM) to provide compound IVa (440 mg).

To a 0° C. solution of IVa (237 mg, 1.6 mmol), TH-1152 (550 mg, 1.3 mmol), and PPh₃ (427 mg, 1.6 mmol), in anhydrous toluene (5 mL) was added DIAD (330 μL, 1.6 mmol) in anhydrous toluene, dropwise. The reaction mixture was stirred for 30 min, allowed to come to RT, stirred for 2 h, silica added to it and volatiles removed. The residue was purified by column chromatography using 0-50% acetone toluene then 0-70% EtOAc/Hexanes to provide TH-1456 (310 mg). ¹H NMR (400 MHz, CDCl₃) δ 7.98 (d, J=6.8 Hz, 1H), 7.57-7.49 (m, 2H), 7.46 (d, J=9.1 Hz, 1H), 7.31 (s, 1H), 7.17-7.10 (m, 1H), 7.08 (d, J=9.2 Hz, 2H), 6.73 (t, J=6.7 Hz, 1H), 6.60 (d, J=9.6 Hz, 2H), 6.51 (dd, J=10.9, 4.2 Hz, 1H), 4.08-3.99 (m, 1H), 3.78-3.54 (m, 9H).

Q. TH-1435

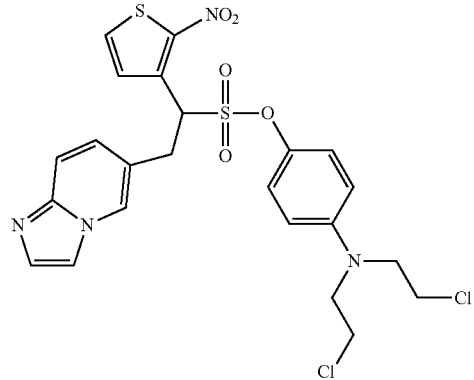

To a 0° C. solution of imidazo[1,2-a]pyridinyl-6-methanol (76 mg, 0.51 mmol), TH-1152 (150 mg, 0.34 mmol), and PPh₃ (134 mg, 0.51 mmol), in anhydrous toluene (1.5 mL) was added DIAD (103 μL, 0.51 mmol). The reaction mixture was stirred for 5 min, allowed to come to RT, stirred 3 h, silica was added to it and volatiles removed. The residue was purified by column chromatography using 2:1 Hexanes/DCM to 20% acetone/DCM a second column 0-50% acetone/toluene. The residue was triturated with EtOAc to provide TH-1435 as a yellow crystalline solid (65 mg). ¹H NMR (400 MHz, CDCl₃) δ 7.74 (d, J=2.2 Hz, 1H), 7.55 (dd, J=16.2, 5.7 Hz, 2H), 7.29 (dd, J=8.6, 2.4 Hz, 1H), 6.99 (d, J=9.2 Hz, 2H), 6.64 (d, J=8.5 Hz, 1H), 6.60 (d, J=9.2 Hz, 2H), 6.18 (dd, J=11.0, 4.4 Hz, 1H), 4.38-4.24 (m, 2H), 3.79-3.68 (m, 5H), 3.66-3.60 (m, J=13.5, 6.0 Hz, 4H), 3.37-3.25 (m, 1H).

R. TH-1478

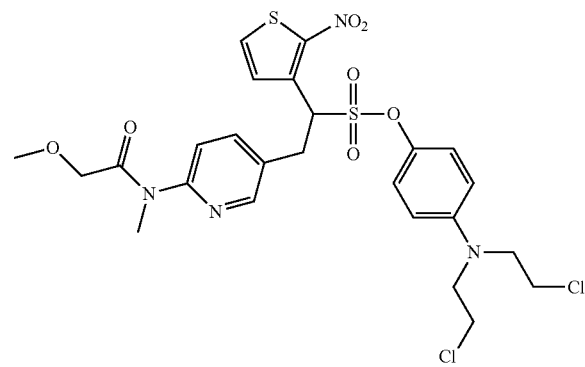

To a 0° C. solution of TH-1442 (50 mg, 0.09 mmol) and TEA (38 μL, 0.27 mmol) in DCM (3 mL) was slowly added a solution of methoxyacetylchloride (17 μL, 0.18 mmol) the reaction mixture was allowed to warm to RT and stirred for 1 h. The reaction mixture was taken up on silica, volatiles removed and the residue separated by column chromatography using 0-100% EtOAc/Hexanes to provide compound TH-1478 (37 mg) ¹H NMR (400 MHz, CDCl₃) δ 8.06 (d, J=2.2 Hz, 1H), 7.73-7.40 (m, 4H), 6.98 (d, J=9.2 Hz, 2H), 6.60 (d, J=9.2 Hz, 2H), 6.19 (dd, J=10.7, 4.7 Hz, 1H), 4.08 (s, 2H), 3.85 (dd, J=14.1, 4.7 Hz, 1H), 3.72 (t, J=6.8 Hz, 4H), 3.61 (t, J=6.7 Hz, 4H), 3.38-3.33 (m, 7H).

S. TH-1354

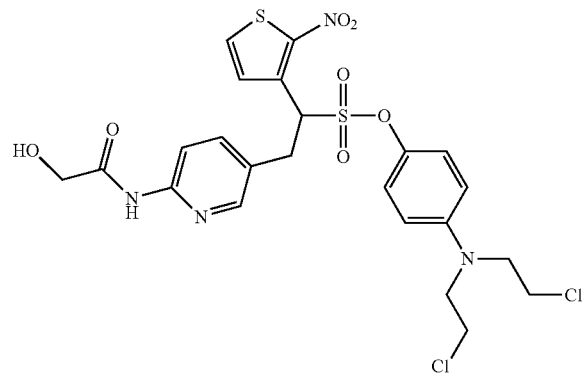

T. TH-1405

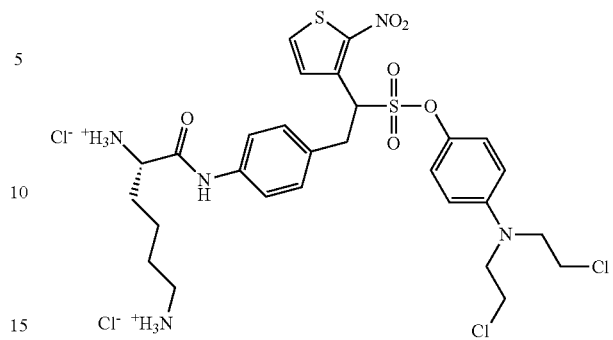

To a 0° C. solution of TH-1255 (80 mg, 0.15 mmol) and TEA (24 µL, 0.44 mmol) in DCM (5 mL) was slowly added a solution of acetoxyacetylchloride (82 µL, 0.36 mmol). The reaction mixture was allowed to warm to RT and stirred for 2 h. The reaction mixture was taken up on silica, volatiles removed and the residue separated by column chromatography using 0-80% EtOAc/Hexanes to provide compound TH-1344 (20 mg) and TH-1345 (50 mg).

To a mixture of TH-1344 (45 mg) in MeOH (2 mL) was added catalytic NaOMe (10 µL, 25% in MeOH) and stirred 30 min. The reaction mixture was neutralized with AcOH, solvents removed, and the residue separated by column chromatography using 0-100% EtOAc/Hexanes to provide compound TH-1354 (35 mg). $^1$H NMR (400 MHz, CDCl$_3$) δ 8.85 (s, 1H), 8.13 (d, J=8.4 Hz, 1H), 7.97 (d, J=1.9 Hz, 1H), 7.57 (dd, J=15.5, 5.7 Hz, 2H), 7.44-7.40 (m, 1H), 6.98 (d, J=9.2 Hz, 2H), 6.60 (d, J=9.2 Hz, 2H), 6.20 (dd, J=10.7, 4.6 Hz, 1H), 4.25 (s, 2H), 3.83 (dd, J=14.1, 4.6 Hz, 1H), 3.72 (t, J=6.9 Hz, 4H), 3.62 (t, J=6.7 Hz, 4H), 3.40-3.34 (m, 1H), 2.96 (s, 1H).

To a 0° C. solution of TH-1330 (120 mg, 0.19 mmol), α-Boc-Lysine-(ε-Boc)-OH (97 mg, 0.28 mmol) in DMF (3 mL) was added DIEA (130 µL, 0.75 mmol) followed by HATU (142 mg, 0.37 mmol). The reaction mixture was stirred at RT overnight. The reaction mixture was diluted with brine, extracted with EtOAc (2×). The organic layer was washed with brine (2×), dried over Na$_2$SO$_4$ and volatiles removed. The residue was purified by column chromatography using 0-100% EtOAc/Hexanes to provide compound TH-1404 (170 mg).

To a solution of TH-1404 in DCM (3 mL) was added TFA (3 mL) the reaction mixture was stirred for 1 h at RT and volatiles removed. The residue was co-evaporated from toluene, dissolved in MeOH, 4M HCl in dioxane (1 ml) added to it, and volatiles removed. The residue was co-evaporated from toluene, sonicated in anhydrous Et$_2$O, filtered and the solid washed with Et$_2$O to provide TH-1405 as a yellow solid (130 mg). $^1$H NMR (400 MHz, CD$_3$OD) δ 7.84 (d, J=5.7 Hz, 1H), 7.63 (d, J=5.7 Hz, 1H), 7.49 (d, J=7.6 Hz, 2H), 7.05 (dd, J=14.0, 8.8 Hz, 4H), 6.74 (d, J=9.2 Hz, 2H), 6.20 (dd, J=11.5, 4.0 Hz, 1H), 5.49 (s, 2H), 4.03 (t, J=6.5 Hz, 1H), 3.87-3.57 (m, 11H), 3.51-3.36 (m, 1H), 2.98-2.90 (m, 2H), 2.07-1.86 (m, 2H), 1.72 (dt, J=15.2, 7.7 Hz, 2H), 1.62-1.42 (m, 2H).

Scheme V.

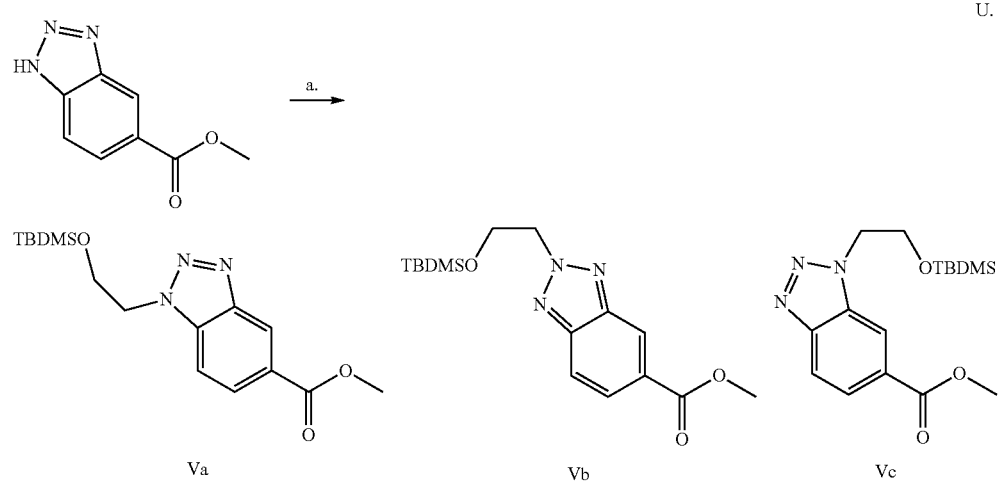

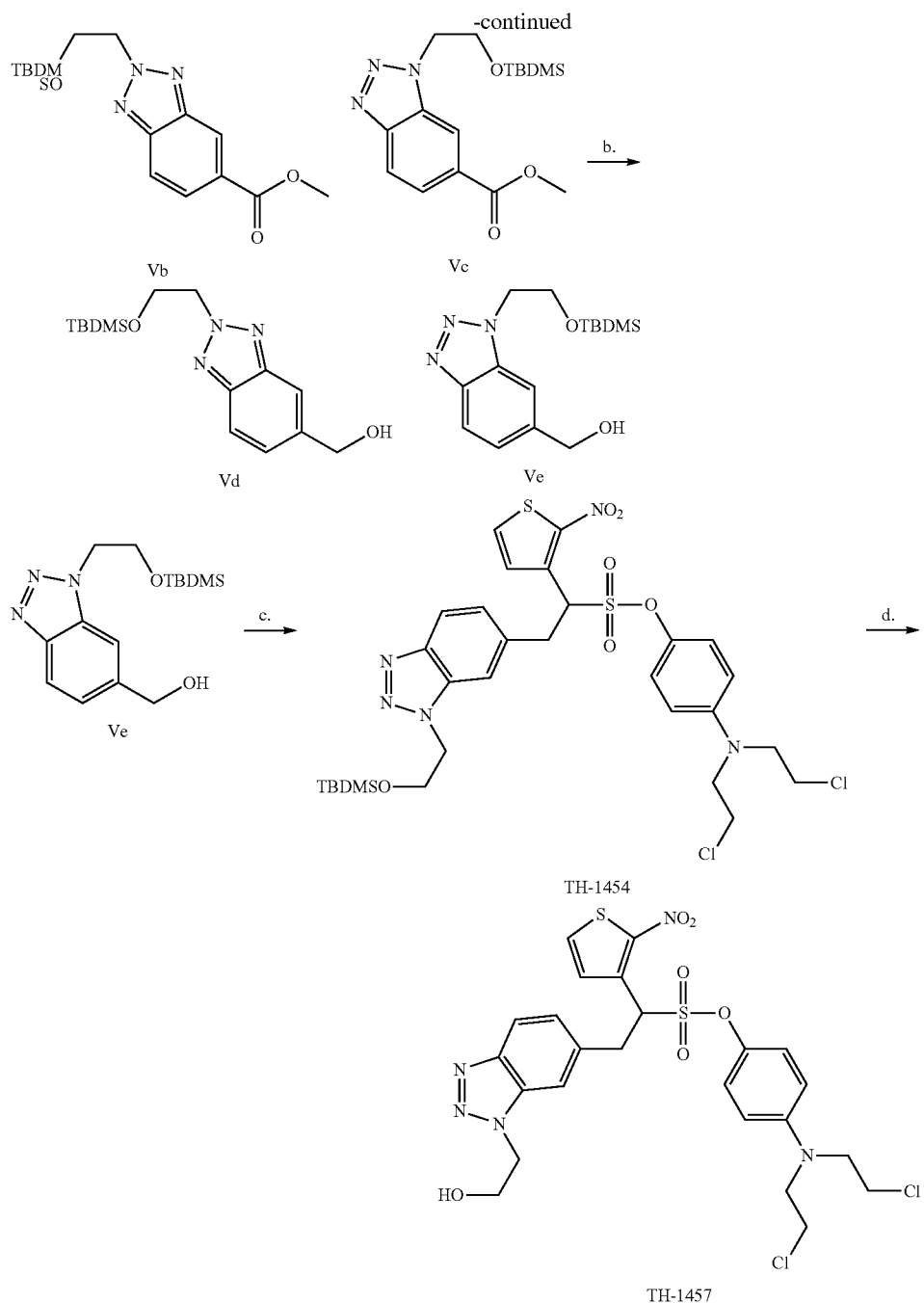

a. (2-bromoethoxy)-tert-butyldimethylsilane, NaH, DMF
b. LiAlH₄
c. TH-1152, DIAD, PPh₃
d. EtOH, aq. HCl.

To a 0° C. suspension of pentane washed sodium hydride (223 mg, 5.6 mmol) in DMF (8 mL) was added methyl 1,2,3-benzotriazole-5-carboxylate (0.94 g) in DMF (12 mL), the reaction mixture was stirred for 15 min, and allowed to come to room temperature.

A solution of (2-bromoethoxy)-tert-butyldimethylsilane (1.36 mL, 6.36 mmol) was added to the reaction mixture which was stirred for 1 h, and heated to 50° C. for 18 h. The reaction mixture was diluted with EtOAc, the organic layer washed with 1:1 water/saturated NaHCO₃ (2×), water, brine, dried over Na₂SO₄ and volatiles removed. The residue was purified by column chromatography using 0-30% EtOAc/Hexanes to provide compound Va (617 mg) and a mixture of Vb and Vc (0.91 g).

To a 0° C. solution of a mixture of Vb and Vc (0.91 g) in DCM (25 mL) was added diisobutylaluminumhydride (11.9 mL, 1M in hexanes, 11.9 mmol), dropwise, stirred for 40 min. 5 mL EtOAc was added to the reaction mixture cautiously followed a saturated solution of sodium potassium tartrate (200 μL). The reaction mixture was diluted with DCM, dried with Na$_2$SO$_4$, filtered trough celite and solvents were removed. The residue was purified by column chromatography using 0-80% EtOAc/Hexanes to provide Vd high R$_f$ (155 mg) and Ve low R$_f$ (133 mg) as a colorless solids and mixed fractions of Vd and Ve (290 mg).

To a solution of Ve (85 mg, 0.27 mmol), TH-1152 (100 mg, 0.23 mmol), and PPh$_3$ (120, 0.46 mmol) in THF (3 mL), was added DIAD (90 µL, 0.46 mmol) and the reaction mixture was stirred over night. The reaction mixture was diluted with EtOAc and washed with water and brine, dried over Na$_2$SO$_4$ and volatiles removed. The residue was purified by column chromatography using 0-40% EtOAc/Hexanes to provide TH-1454.

To a solution of TH-1454 in EtOH (5 mL) was added conc. HCl (1 mL), stirred for 0.5 h, and volatiles removed. The residue was treated with sat. NaHCO$_3$ and extracted with EtOAc, dried over Na$_2$SO$_4$, volatiles removed and the resulting residue purified by column chromatography using 0-100% EtOAc/Hexanes followed by a second column 0-60% acetone/toluene to provide TH-1457 (70 mg). $^1$H NMR (400 MHz, CDCl$_3$) δ 7.71 (d, J=9.1 Hz, 2H), 7.56 (t, J=5.3 Hz, 2H), 7.21-7.08 (m, 1H), 7.01 (d, J=9.2 Hz, 2H), 6.60 (d, J=9.2 Hz, 2H), 6.35 (dd, J=11.1, 4.3 Hz, 1H), 5.07-4.88 (m, 1H), 4.85-4.73 (m, 2H), 4.50-4.20 (m, 2H), 4.00 (dd, J=13.9, 4.3 Hz, 1H), 3.70 (t, J=6.9 Hz, 4H), 3.60 (t, J=6.7 Hz, 4H), 3.52 (dd, J=13.9, 11.3 Hz, 1H), 3.22 (t, J=6.3 Hz, 1H).

V. TH-1451

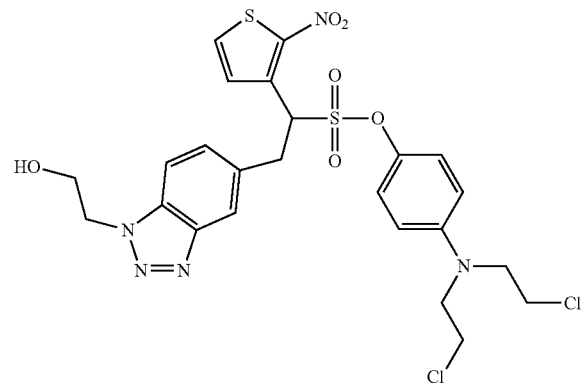

The synthesis of TH-1451 was conducted as that of TH-1457 using intermediate Va. $^1$H NMR (400 MHz, CD$_3$OD) δ 7.64-7.60 (m, 2H), 7.47 (d, J=5.7 Hz, 1H), 7.40 (s, 1H), 7.06-6.99 (m, 1H), 6.85 (d, J=9.2 Hz, 2H), 6.54 (d, J=9.2 Hz, 2H), 6.18 (dd, J=11.2, 4.4 Hz, 1H), 4.51 (t, J=5.2 Hz, 2H), 3.87 (dd, J=13.8, 4.4 Hz, 1H), 3.77 (t, J=5.2 Hz, 2H), 3.61-3.44 (m, 9H).

W. TH-1343

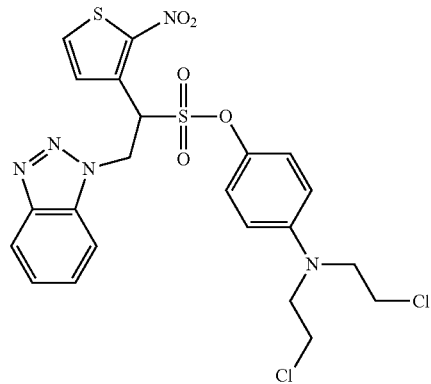

To a solution of TH-1152 (75 mg, 0.17 mmol) and DIEA (119 µL, 0.86 mmol) in MeCN (2 mL) was slowly added a solution of chloromethylbenzotriazole (56 mg, 0.34 mmol). The reaction mixture was allowed to warm to 60° C., NaI (10 mg) was added to it and the reaction mixture stirred overnight. Silica was added to it, volatiles removed and the residue separated by column chromatography using 2:1 Hexanes/DCM to 10% acetone/DCM followed by a second chromatography 0-50% EtOAc/Hexanes to provide TH-1343 as a yellow foam (20 mg). $^1$H NMR (400 MHz, CDCl$_3$) δ 8.01 (d, J=8.4 Hz, 1H), 7.57 (dd, J=3.5 Hz, 2H), 7.54-7.43 (m, 2H), 7.37 (t, J=7.1 Hz, 1H), 6.99 (dd, J=9.1, 2.2 Hz, 2H), 6.65-6.56 (m, 3H), 5.63 (dd, J=14.8, 3.1 Hz, 1H), 5.45-5.35 (m, 1H), 3.70 (t, J=6.6 Hz, 4H), 3.59 (t, J=6.4 Hz, 4H).

X. TH-1266

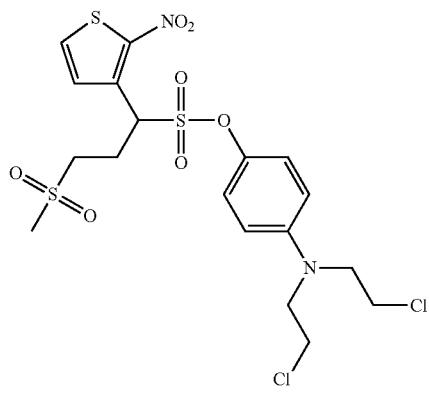

A solution of TH-1152 (50 mg, 0.114 mmol), methylvinylsulfone (11 µL, 0.125 mmol), and tetramethylguanidine (6.4 µL) in MeCN (1 mL) was stirred for 5 h. Additional tetramethylguanidine (6.4 µL) in MeCN (0.5 mL) was added and the reaction stirred overnight. Silica was added and volatiles removed. The residue was purified by column chromatography using 0-100% EtOAc/Hexanes followed by preparative TLC 50% EtOAc/Hexanes to provide TH-1266 as a yellow syrup (19 mg). $^1$H NMR (400 MHz, CDCl$_3$) δ 7.64 (d, J=5.6 Hz, 1H), 7.48 (t, J=7.4 Hz, 1H), 7.00 (d, J=9.2 Hz, 2H), 6.61 (d, J=9.2 Hz, 2H), 6.03 (dd, J=9.0, 4.9 Hz, 1H), 3.72 (t, J=6.9 Hz, 4H), 3.60 (dd, J=16.2, 9.3 Hz, 4H), 3.31-3.17 (m, 1H), 3.07-2.98 (m, 2H), 2.95 (s, 3H), 2.79-2.64 (m, 1H).

Y. TH-1292

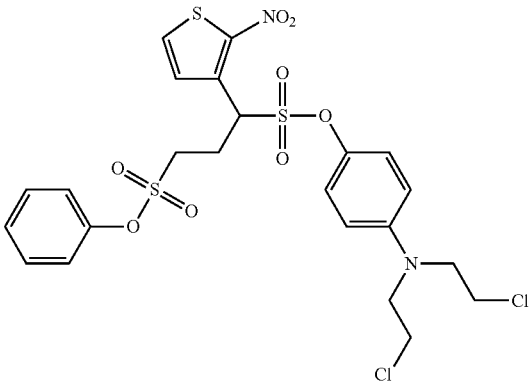

The synthesis of TH-1292 was conducted as that of TH-1266 upon appropriate substitution of starting material.

$^1$H NMR (400 MHz, CDCl$_3$) δ 7.64 (d, J=5.6 Hz, 1H), 7.48-7.37 (m, 3H), 7.34 (t, J=7.4 Hz, 1H), 7.25 (dd, J=6.9, 5.8 Hz, 2H), 7.00 (d, J=9.2 Hz, 2H), 6.60 (d, J=9.2 Hz, 2H), 6.05 (dd, J=8.7, 5.9 Hz, 1H), 3.79-3.66 (m, 4H), 3.66-3.56 (m, 4H), 3.47 (ddd, J=14.3, 10.6, 5.7 Hz, 1H), 3.37-3.25 (m, 1H), 3.16 (ddd, J=14.4, 10.9, 5.6 Hz, 1H), 2.91-2.71 (m, 1H).

Scheme VI.

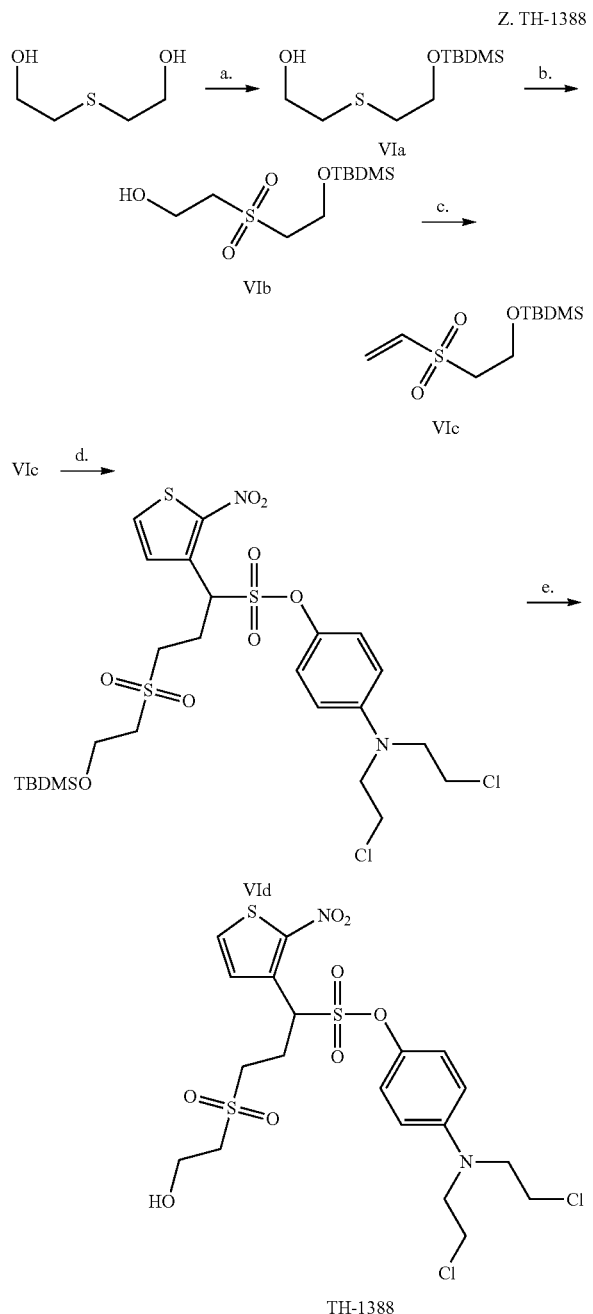

a. TBDMSCl, NaH, THF
b. MCPBA
c. MsCl, TEA
d. TH-1152, tetramethylguanidine, MeCN
e. EtOH, aq. HCl.

To a suspension of sodium hydride (60% in mineral oil, 387 mg, 9.7 mmol) in THF (19 mL) was added 2,2'-thiodiethanol (1.0 mL, 9.7 mmol) the reaction mixture was stirred for 1 h. A solution of TBDMSCl (1.46 g, 9.7 mmol) was added to the reaction mixture which was stirred overnight. The reaction mixture was diluted with Et$_2$O and the organic layer washed with 1:1 water/brine (1×), water brine (1×), dried over Na$_2$SO$_4$ and volatiles removed. The residue was purified by column chromatography using 0-20% EtOAc/Hexanes to provide compound VIa (1.3 g).

To a solution of VIa (254 mg, 1.08 mmol) in DCM (10 mL) was added MCPBA (482 mg, 77%, 2.15 mmol) the reaction mixture was stirred for 2 h. The reaction mixture was diluted with EtOAc and the organic layer washed with saturated NaHCO$_3$ (2×), brine (1×), dried over Na$_2$SO$_4$ and volatiles removed to provide compound VIb as a clear semi-solid (300 mg).

To a solution of VIb (268 mg, 1.08 mmol) in DCM (4 mL) was added TEA (375 μL, 2.7 mmol) and MsCl (100 μL, 1.3 mmol). The reaction mixture was stirred overnight. Silica was added to the reaction mixture and volatiles removed the residue was purified by column chromatography using 0-80% EtOAc/Hexanes to provide compound VIc as a clear oil (173 mg).

A solution of TH-1152 (100 mg, 0.23 mmol), VIc (80 mg, 0.32 mmol), and tetramethylguanidine (14.2 μL, 0.11 mmol) in MeCN (1 mL) was stirred overnight and volatiles removed. The residue was purified by column chromatography using 0-40% EtOAc/Hexanes to provide VId (65 mg).

To a solution of VId (65 mg) in EtOH (3 mL) was added 4M HCl (130 μL), stirred for 3 h, and volatiles removed. The residue was treated with TEA (0.5 ml) volatiles removed and the resulting residue purified by column chromatography using 0-100% EtOAc/Hexanes to provide TH-1388 (46 mg).
$^1$H NMR (400 MHz, CDCl$_3$) δ 7.63 (d, J=5.7 Hz, 1H), 7.46 (d, J=5.7 Hz, 1H), 7.02 (d, J=9.2 Hz, 2H), 6.60 (d, J=9.2 Hz, 2H), 6.06-6.01 (m, 1H), 4.12 (dt, J=8.4, 6.2 Hz, 2H), 3.72 (t, J=6.8 Hz, 4H), 3.62 (t, J=6.7 Hz, 4H), 3.38-3.29 (m, 1H), 3.22 (dd, J=5.7, 2.9 Hz, 2H), 3.15-3.01 (m, 2H), 2.79-2.64 (m, 1H).

Scheme VII.

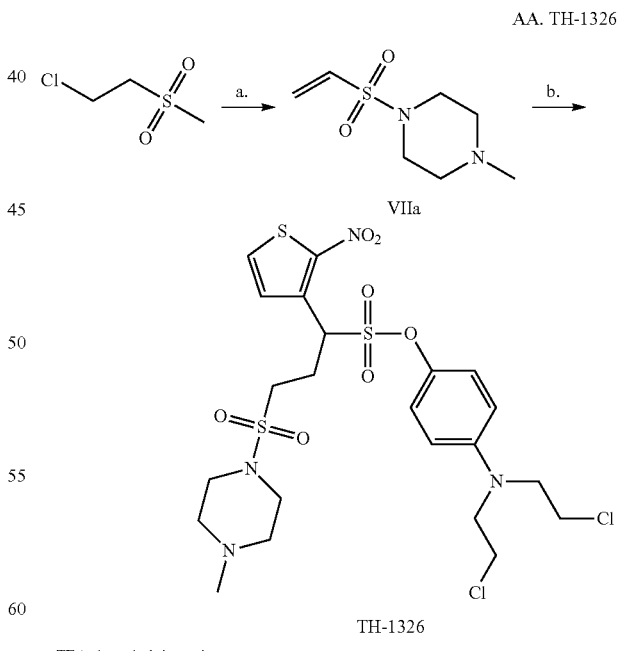

a. TEA, 1-methylpiperazine
b. TH-1152, tetramethylguanidine, MeCN.

To a 0° C. solution of 1-methylpiperazine (1.9 ml, 13.5 mmol) and TEA (0.75 ml, 6.6 mmol) in DCM (20 mL) was added and 2-chloroethylsulfonylchloride (0.64 ml, 6.1 mmol), dropwise, the reaction mixture was allowed to warm up to room temperature and stirred overnight. Silica was added to the reaction mixture, volatiles removed, and the residue was purified by column chromatography using 0-8% MeOH/DCM to provide compound VIIa as a clear oil (173 mg).

A solution of TH-1152 (100 mg, 0.23 mmol), VIIa (60 mg, 0.32 mmol), and tetramethylguanidine (14.3 µL, 0.11 mmol) in MeCN (1 mL) was stirred overnight and volatiles removed. The residue was purified by column chromatography using 0-10% MeOH/DCM to provide Synthesis of TH-1326 (33 mg). $^1$H NMR (400 MHz, CDCl$_3$) δ 7.63 (d, J=5.6 Hz, 1H), 7.45 (d, J=5.6 Hz, 1H), 7.00 (d, J=9.1 Hz, 2H), 6.61 (d, J=9.1 Hz, 2H), 6.02 (dd, J=8.7, 5.4 Hz, 1H), 3.72 (t, J=6.8 Hz, 4H), 3.62 (t, J=6.7 Hz, 4H), 3.29 (s, 4H), 3.15-2.87 (m, 3H), 2.73-2.58 (m, 1H), 2.47 (s, 4H), 2.32 (s, 3H).

Scheme VIII.

BB. TH-1475

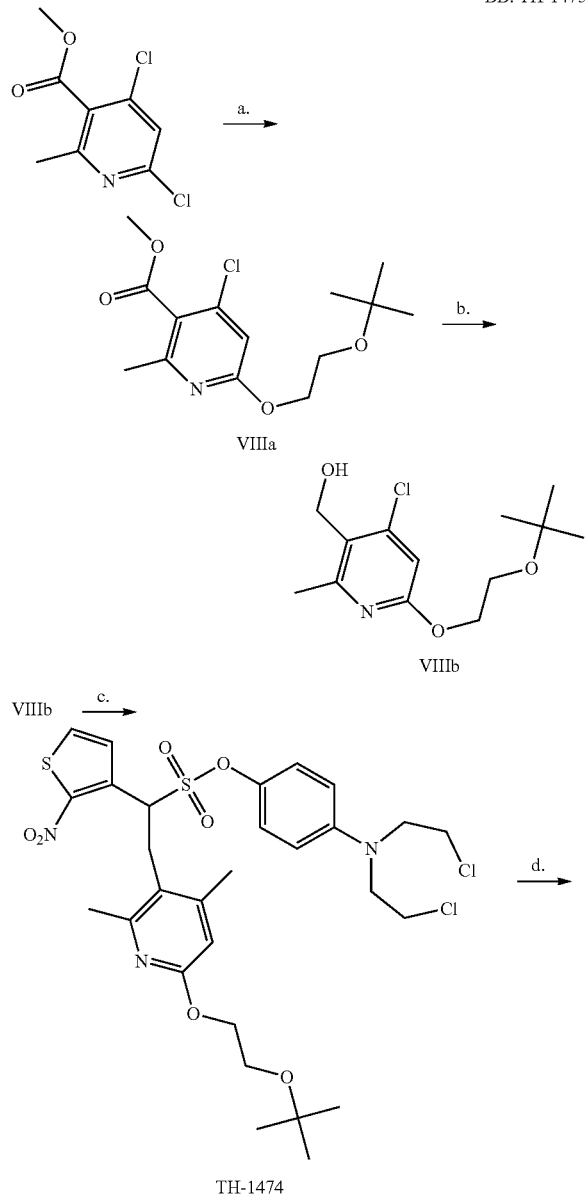

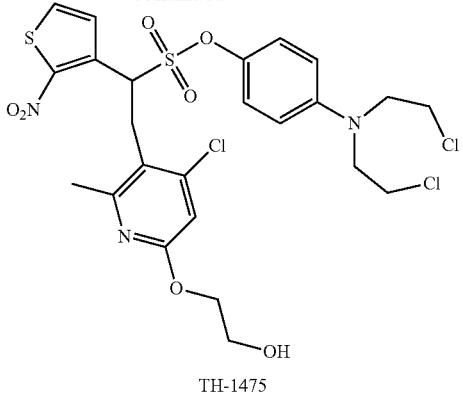

TH-1475 a. ethyleneglycolmono t-butyl ether, NaH, DMF
b. LiAlH$_4$
c. TH-1152, DIAD, PPh$_3$
d. TFA.

To a stirred suspension of sodium hydride (60% in mineral oil, 85 mg, 2.14 mmol) in DMF (4 mL) was added, dropwise, ethyleneglycol mono t-butyl ether (278 mg, 2.35 mmol). the reaction mixture was stirred for 25 min. A solution of 4,6-dichloro-2-methyl-nicotinic acid methylester (0.5 g, 2.14 mmol) in DMF (1.5 mL) was added to the reaction mixture was stirred at RT overnight. The reaction mixture was quenched with water, extracted with EtOAc, the organic layer washed with water, brine, dried over Na$_2$SO$_4$ and volatiles removed. The residue was purified by column chromatography using 0-50% EtOAc/Hexanes to provide compound VIIIa (260 mg).

To a 0° C. solution of VIIIa (260 mg) in THF (2 mL) was added lithium aluminum hydride (0.82 mL, 2M in THF), dropwise, stirred for 30 min and the reaction mixture quenched with MeOH. The reaction mixture was diluted with EtOAc and the organic layer washed with saturated NH$_4$Cl (1×), brine (1×), dried over Na$_2$SO$_4$ and volatiles removed. The residue was purified by column chromatography using 0-100% MeOH/DCM to provide compound VIIIb as a clear syrup (160 mg).

To a 0° C. solution of VIIIb (72 mg, 0.34 mmol), TH-1152 (75 mg, 0.17 mmol), and PPh$_3$ (72 mg, 0.24 mmol) in anhydrous toluene (25 mL) was added, dropwise, DIAD (54 µL, 10.3 mmol). The reaction mixture was stirred for 5 min, allowed to come to RT and stirred for 3 h. Silica was added and volatiles removed. The residue was purified by column chromatography (1:1 Hexanes/DCM to 10% acetone/DCM) to provide TH-1474 as a yellow solid (98 mg).

To TH-1474 was added TFA (8 mL) and water (80 µL), the reaction mixture was stirred for 1 h at RT, and volatiles removed. The residue was purified by column chromatography using 0-80% EtOAc/Hexanes to provide compound TH-1475 as a yellow solid (40 mg). $^1$H NMR (400 MHz, CDCl$_3$) δ 7.70 (d, J=5.7 Hz, 1H), 7.61 (d, J=5.7 Hz, 1H), 6.90 (d, J=9.2 Hz, 2H), 6.68 (s, 1H), 6.57 (d, J=9.2 Hz, 2H), 6.32 (dd, J=9.9, 3.7 Hz, 1H), 4.21-4.08 (m, 3H), 4.04-3.86 (m, 3H), 3.71 (t, J=6.8 Hz, 4H), 3.60 (t, J=6.7 Hz, 4H), 3.28 (dd, J=13.9, 10.0 Hz, 1H), 2.46 (s, 2H), 2.11 (s, 3H).

CC. TH-1504

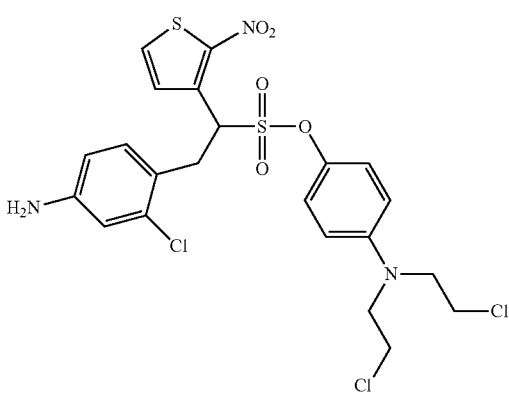

To a −40° C. solution of methyl-2-chloro-4-amino-benzoate (0.6 g, 3.23 mmol), Boc$_2$O (2.12 g, 9.6 mmol) and TEA (1.8 ml, 6.6 mmol) in MeCN (8 mL) was added and DMAP (47 mg, 6.1 mmol). The reaction mixture was allowed to warm gradually to room temperature and stirred for 48 h and volatiles removed. The residue was purified by column chromatography using 0-50% EtOAc/Hexanes to provide compound methyl-2-chloro-4-(bis-Boc-amino)-benzoate as a clear syrup (830 mg).

To a 0° C. solution of methyl-2-chloro-4-(bis-Boc-amino)-benzoate (491 mg) in THF (4 mL) was added lithium aluminum hydride (1.27 mL, 2M in THF), dropwise, the reaction mixture was stirred for 30 min and quenched with MeOH. The reaction mixture was diluted with EtOAc, the organic layer washed with saturated NH$_4$Cl (1×), brine (1×), dried over Na$_2$SO$_4$ and volatiles removed. The residue was purified by column chromatography using 0-60% EtOAc/Hexanes to provide compound 2-chloro-4-(boc-amino)-benzylalcohol as a clear syrup (259 mg).

The synthesis of TH-1504 from intermediate 4-(boc-amino)-2-chlorobenzylalcohol was conducted as that of TH-1255. $^1$H NMR (400 MHz, CDCl$_3$) δ 7.54 (dd, J=14.5, 5.6 Hz, 2H), 7.03 (d, J=9.1 Hz, 2H), 6.70 (dd, J=10.8, 5.0 Hz, 2H), 6.60 (d, J=9.1 Hz, 2H), 6.41 (dd, J=8.1, 1.9 Hz, 1H), 6.34 (dd, J=10.6, 4.4 Hz, 1H), 4.18 (s, 2H), 3.90 (dd, J=13.9, 4.5 Hz, 1H), 3.71 (t, J=6.9 Hz, 4H), 3.61 (t, J=6.8 Hz, 4H), 3.38 (dd, J=13.8, 10.8 Hz, 1H).

DD. TH-1545

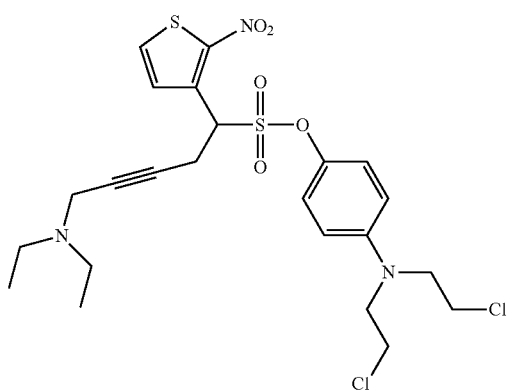

The synthesis of TH-1545 from TH-1152 and 4-diethylamino-2-butyn-1-ol was conducted as that of TH-1331. $^1$H NMR (400 MHz, CDCl$_3$) δ 7.59 (d, J=5.6 Hz, 1H), 7.47 (d, J=5.6 Hz, 1H), 7.02 (d, J=9.2 Hz, 2H), 6.61 (d, J=9.2 Hz, 2H), 6.14 (dd, J=10.6, 4.4 Hz, 1H), 3.72 (t, J=6.8 Hz, 4H), 3.62 (t, J=6.7 Hz, 4H), 3.41-3.34 (m, 3H), 3.24-3.10 (m, 1H), 2.41 (q, J=7.1 Hz, 4H), 1.00 (t, J=7.2 Hz, 6H).

EE. TH-1465

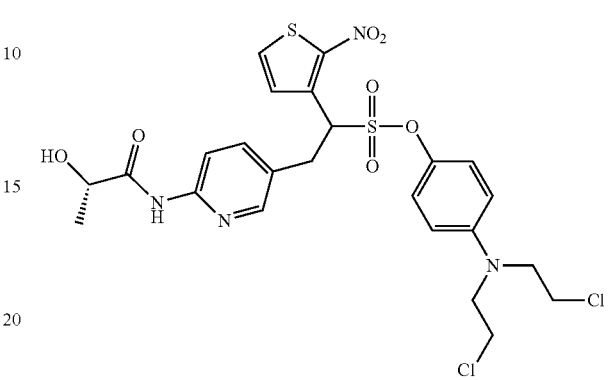

The synthesis of TH-1465 from TH-1255 was conducted as that of TH-1354 upon appropriate substitution of starting material. $^1$H NMR (400 MHz, CDCl$_3$) δ 9.33 (s, 1H), 8.15 (d, J=8.6 Hz, 1H), 7.95 (dd, J=6.4, 2.0 Hz, 1H), 7.56 (dd, J=21.1, 5.6 Hz, 2H), 7.46-7.39 (m, 1H), 6.98 (d, J=9.2 Hz, 2H), 6.60 (d, J=9.2 Hz, 2H), 6.20 (dd, J=10.6, 4.7 Hz, 1H), 4.80-4.75 (m, 1H), 4.36 (dd, J=6.4, 3.5 Hz, 1H), 3.82 (dd, J=14.2, 4.6 Hz, 1H), 3.71 (t, J=6.9 Hz, 4H), 3.61 (t, J=6.7 Hz, 4H), 3.37 (dd, J=14.1, 10.8 Hz, 1H), 1.50 (d, J=6.8 Hz, 3H).

FF. TH-1521

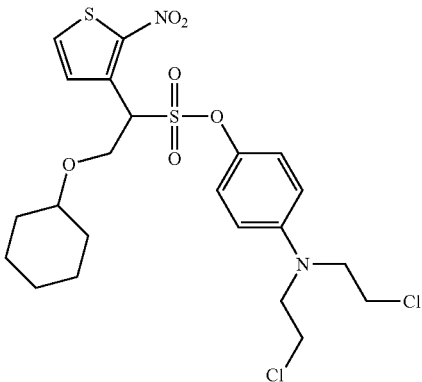

The synthesis of TH-1521 from TH-1152 and chloromethyl cyclohexyl ether was conducted as that of TH-1343. $^1$H NMR (400 MHz, CDCl$_3$) δ 7.51 (t, J=5.7 Hz, 2H), 7.06 (d, J=9.1 Hz, 2H), 6.61 (d, J=9.1 Hz, 2H), 6.15 (t, J=5.9 Hz, 1H), 4.25 (dd, J=10.3, 5.2 Hz, 1H), 4.15 (dd, J=10.3, 6.7 Hz, 1H), 3.77-3.53 (m, 8H), 3.43-3.25 (m, 1H), 1.95-(m, 10H).

Example 2

Anti Cancer Efficacy of the Hypoxia Activated Drug Compounds of the Present Invention A. Anti Cancer Efficacy as Measured in Cellular Monolayers This example demonstrates the cytotoxicities of hypoxia activated drug compounds of the present invention employing an AlamarBlue fluorescence intensity based detection of cell survival. H460 (20,000 cells/well/500 μL, ATCC HTB-177) were seeded in glass inserts on 24-well plates in RPMI1640 medium supplemented with 10% FBS and 1% Penicillin/Streptomycin (Invitrogen Corporation, Carlsbad, Calif.). The cells were incubated for 24 h at 37° C. in 5% $CO_2$, 95% air and 100% relative humidity (these incubation conditions were used throughout the experiment unless otherwise mentioned) and divided into 2 groups: a "control group" (no test compound), and "treatment groups" (in which the cells were kept in contact with the test compound at various concentrations for 2 h).

The control fluorescence intensity, or $F_0$, proportional to the cell population of the control group at the beginning of the experiment, was determined following an AlamarBlue assay ($\lambda_{ex}$=550 nm and $\lambda_{em}$=590 nm). See also, Invitrogen Corporation, Tech Application Notes, Use of Alamar Blue in the measurement of Cell Viability and Toxicity, Determining $IC_{50}$. The cells in the treatment groups were incubated for 2 hours with 6 different concentrations of a test compound (in the concentration ranges of about 10 nM-10 μM, 10 nM-300 μM, and/or 10 nm-1000 μM depending on the cytotoxicity of the tested compound; the more the cytotoxicity of the tested compound, the narrower was the concentration range tested), under hypoxia (5% $CO_2$, 5% $H_2$, 90% $N_2$) or normoxia (5% $CO_2$, 95% air), media containing the test compound removed, fresh media added, and the cells incubated for 3 days. The fluorescence intensities of the various treatment group cells incubated with different concentrations of the test compound and having different cell populations, and the control group cells at the end of the experiment ($F_t$) having the highest cell population among all the groups, was determined following an AlamarBlue assay. The fluorescence intensities determined were background corrected by subtracting $F_0$, and normalized by dividing with $F_t$-$F_0$. The background corrected and normalized fluorescence intensities of the control group after 3 days of incubation, and the various treatment groups after 3 days of incubation, were plotted against the corresponding concentrations of the test compound. The $IC_{50}$ value for the test compound, i.e., the concentration of the test compound that killed, or made unviable, 50% of the cells, was calculated based on a best-fit plot using an F test (GraphPad Prism4 software, San Diego, Calif.). Using a similar method, the cytotoxicities of hypoxia activated drug compounds of the present invention were also demonstrated in HT29 cell lines.

The results, tabulated below, demonstrate that compounds or hypoxia activated drug compounds of the present invention are more cytotoxic under hypoxia than under normoxia. The relative cytotoxicity of a compound under noromoxia and hypoxia is expressed by its hypoxia cytotoxicity ratio or HCR. The higher the HCR, the greater the hypoxia selective toxicity of the compound. Certain compounds, under the conditions and in the cell line tested, may not show enhanced cytotoxicity under hypoxia than under normoxia. However, these compounds can be more cytotoxic under hypoxia than under normoxia when different test conditions and/or cell lines are used. Such different test conditions and cell lines useful for these purposes can be adapted by one of skill in the art from conditions and methods reported in literature upon reading this disclosure.

TABLE 1

| TH-# | Structure | 2 h Air H460 monolayer $IC_{50}$ μM | 2 h $N_2$ H460 monolayer $IC_{50}$ μM | 2 h Air H460 spheroid $IC_{50}$ μM | 2 h $N_2$ H460 spheroid IC50 μM |
|---|---|---|---|---|---|
| 1103 | [structure: 2-nitrothiophene-CH2-SO2-O-phenyl(methyl)-N(CH2CH2Cl)2] | 0.7 | 0.1 | | |
| 1104 | [structure: 2-nitro-1-methylimidazole-CH2-SO2-NH-phenyl-N(CH2CH2Cl)2] | 7.4 | 6.1 | | |
| 1105 | [structure: 2-nitroimidazole-CH2-SO2-NH-phenyl-N(CH2CH2Cl)2] | 7.6 | 4.2 | | |

TABLE 1-continued

| TH-# | Structure | 2 h Air H460 monolayer IC$_{50}$ μM | 2 h N$_2$ H460 monolayer IC$_{50}$ μM | 2 h Air H460 spheroid IC$_{50}$ μM | 2 h N$_2$ H460 spheroid IC50 μM |
|---|---|---|---|---|---|
| 1106 | 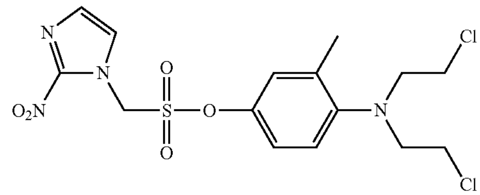 | 0.9 | 0.2 | | |
| 1107 | 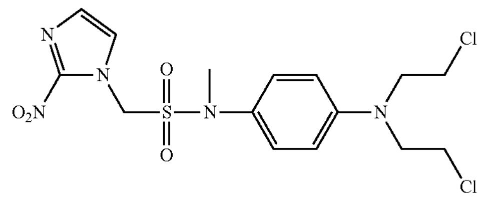 | 113.4(33) | 7.9(7.2) | <0.69 | <0.69 |
| 1108 | 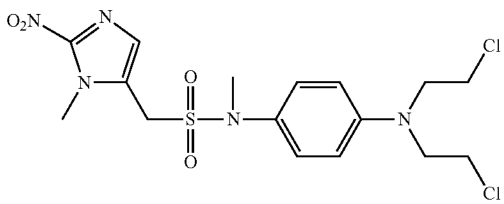 | 15 | 11 | | |
| 1110 | 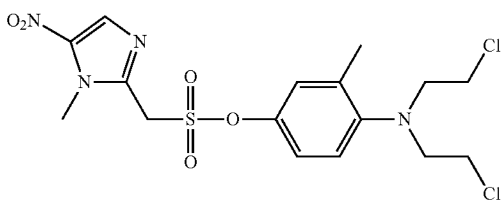 | 1.4 | 2.1 | | |
| 1111 | 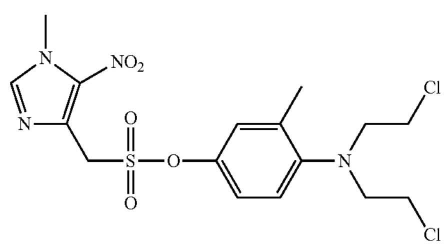 | 4.7 | 2.5 | | |
| 1112 | 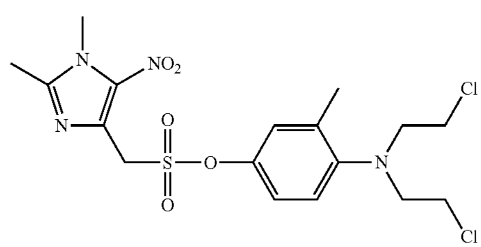 | 1.4 | 1.7 | | |
| 1115 | 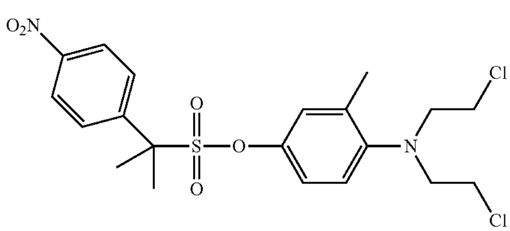 | 13 | 3 | | |

TABLE 1-continued
| TH-# | Structure | 2 h Air H460 monolayer IC$_{50}$ μM | 2 h N$_2$ H460 monolayer IC$_{50}$ μM | 2 h Air H460 spheroid IC$_{50}$ μM | 2 h N$_2$ H460 spheroid IC50 μM |
|---|---|---|---|---|---|
| 1116 | 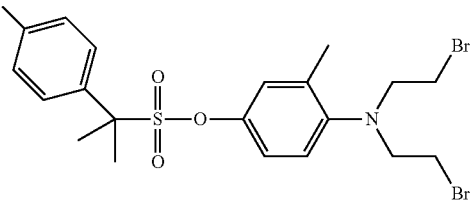 | 1.1 | 0.6 | | |
| 1117 | 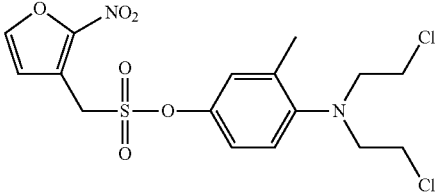 | 2.3 | 1.1 | | |
| 1118 | 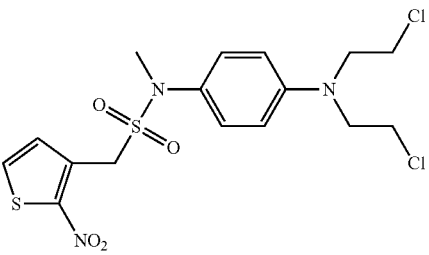 | 12.9 | 6.7 | | |
| 1119 | 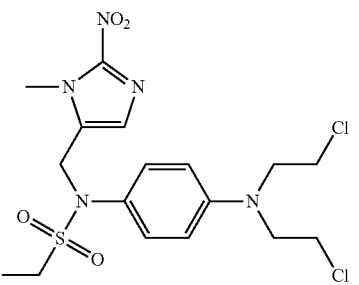 | >300 | >300 | | |
| 1120 | 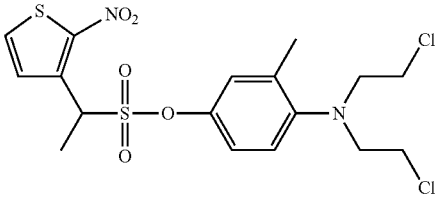 | 2.4 | 0.3 | <0.08 | <0.08 |
| 1121 | 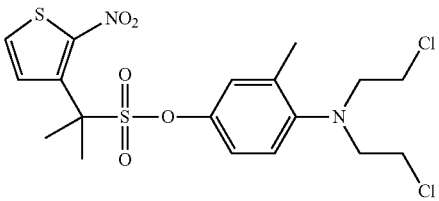 | 1.3 | 0.3 | | |

TABLE 1-continued

| TH-# | Structure | 2 h Air H460 monolayer IC$_{50}$ μM | 2 h N$_2$ H460 monolayer IC$_{50}$ μM | 2 h Air H460 spheroid IC$_{50}$ μM | 2 h N$_2$ H460 spheroid IC50 μM |
|---|---|---|---|---|---|
| 1122 | 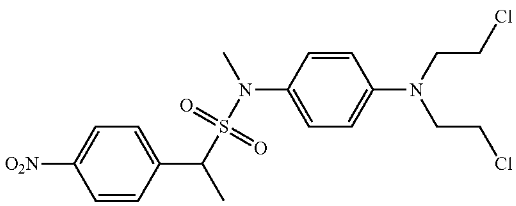 | >300 | >300 | | |
| 1123 | 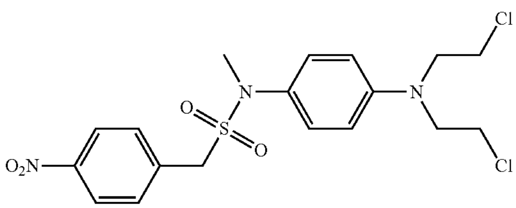 | >300 | >300 | | |
| 1124 | 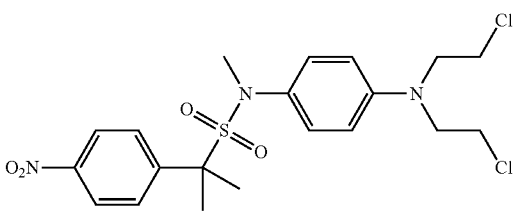 | 289 | 243 | | |
| 1125 | 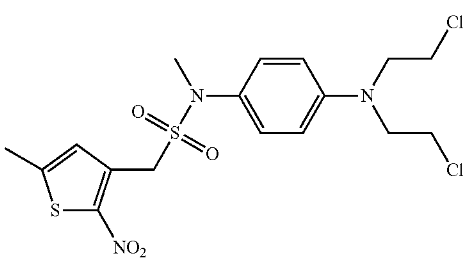 | 148 | 69 | | |
| 1126 | 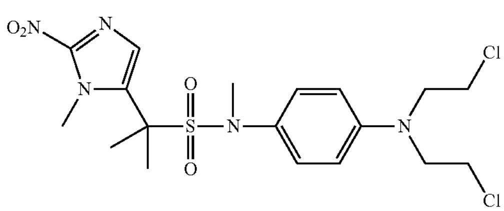 | 45 | 7.1 | <0.69 | <0.69 |
| 1127 | 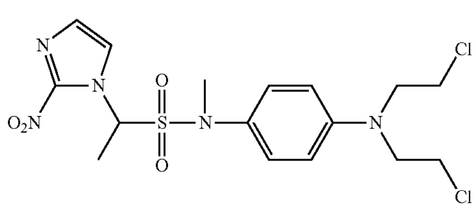 | 37 | 3.9 | <0.69 | <0.69 |

TABLE 1-continued

| TH-# | Structure | 2 h Air H460 monolayer IC$_{50}$ μM | 2 h N$_2$ H460 monolayer IC$_{50}$ μM | 2 h Air H460 spheroid IC$_{50}$ μM | 2 h N$_2$ H460 spheroid IC50 μM |
|---|---|---|---|---|---|
| 1128 | 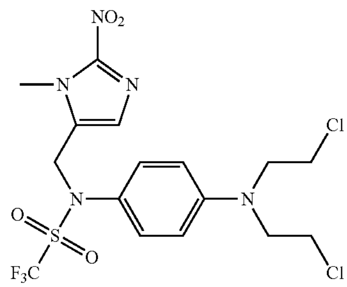 | 267 | 294 | | |
| 1129 | 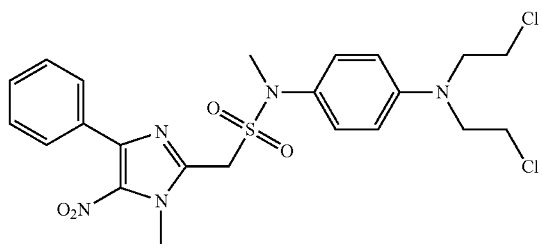 | 6.9 | 3.6 | | |
| 1130 | 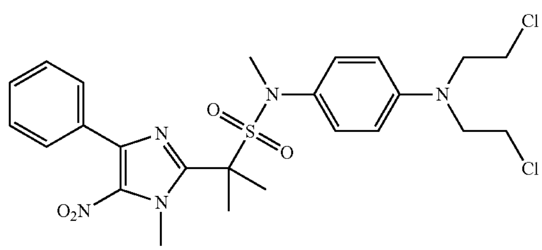 | 122 | 65 | | |
| 1131 | 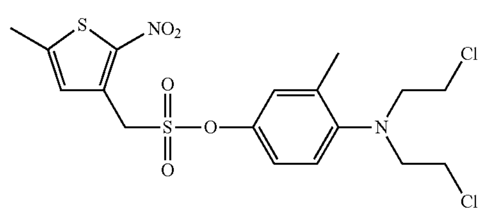 | 1 | 0.3 | | |
| 1132 | 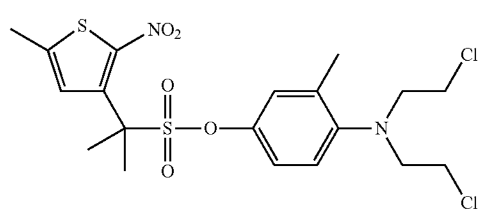 | 2 | 0.3 | | |
| 1133 | 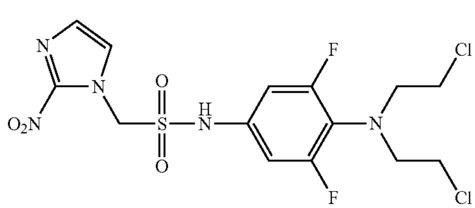 | 11.3 | 5.9 | | |

TABLE 1-continued

| TH-# | Structure | 2 h Air H460 monolayer IC$_{50}$ μM | 2 h N$_2$ H460 monolayer IC$_{50}$ μM | 2 h Air H460 spheroid IC$_{50}$ μM | 2 h N$_2$ H460 spheroid IC50 μM |
|---|---|---|---|---|---|
| 1134 | 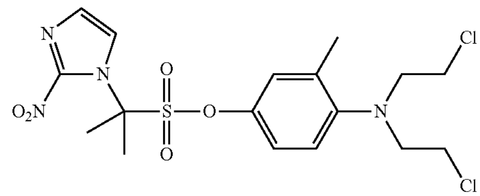 | 0.2 | <0.1 | | |
| 1135 | 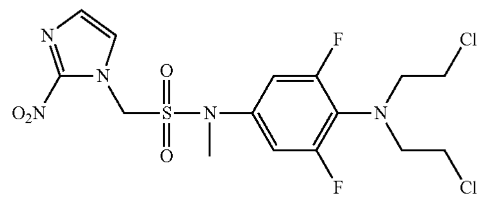 | 9.2 | 3.4 | | |
| 1136 | 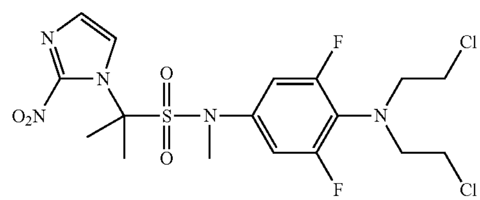 | 5.1 | 5.0 | | |
| 1137 | 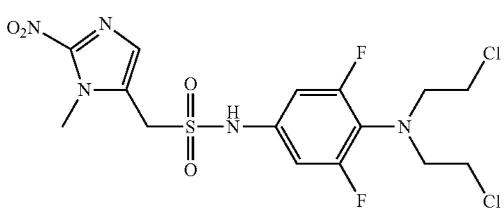 | 20.4 | 8.3 | | |
| 1138 | 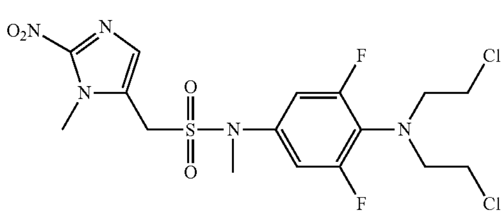 | 34.2 | 13.5 | | |
| 1141 | 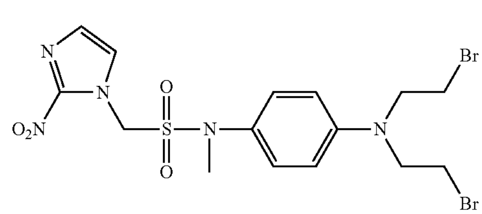 | 0.5 | 0.1 | | |

TABLE 1-continued

| TH-# | Structure | 2 h Air H460 monolayer IC$_{50}$ µM | 2 h N$_2$ H460 monolayer IC$_{50}$ µM | 2 h Air H460 spheroid IC$_{50}$ µM | 2 h N$_2$ H460 spheroid IC50 µM |
|---|---|---|---|---|---|
| 1145 | 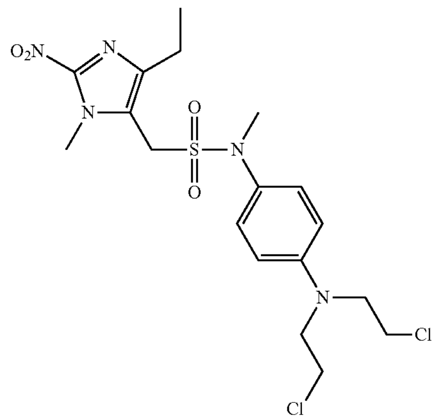 | 78.2 | 3.8 | | |

TABLE 2

| TH-# | Structure | 2 hr Air H460 IC$_{50}$ µM | 2 hr N$_2$ H460 IC$_{50}$ µM | H460 HCR: Air/N$_2$ | 2 hr Air HT29 IC$_{50}$ µM | 2 hr N$_2$ HT29 IC$_{50}$ µM | HT29 HCR: Air/N$_2$ |
|---|---|---|---|---|---|---|---|
| 1360 | 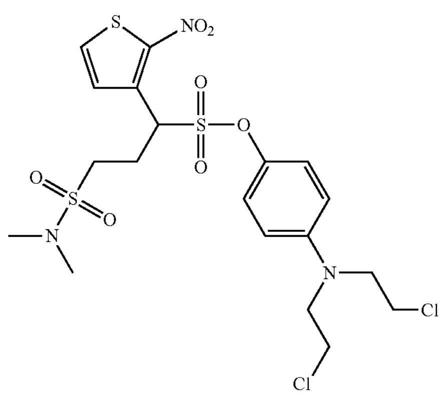 | ~300 | 4.3 | ~70 | >1000 | >1000 | |
| 1426 | 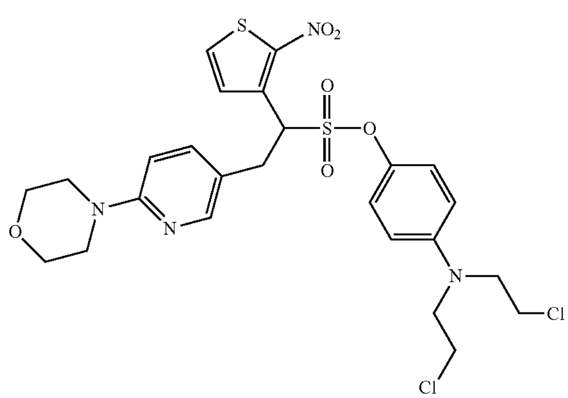 | 190 | 0.2 | 950 | >300 | >300 | |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1325 | 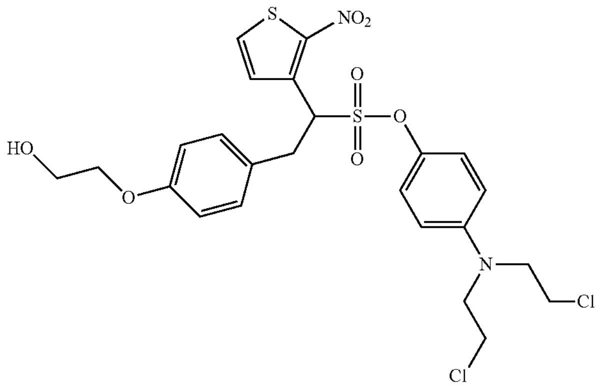 | 92.9 | 0.1 | 929 | >300 | >300 | |
| 1423 | 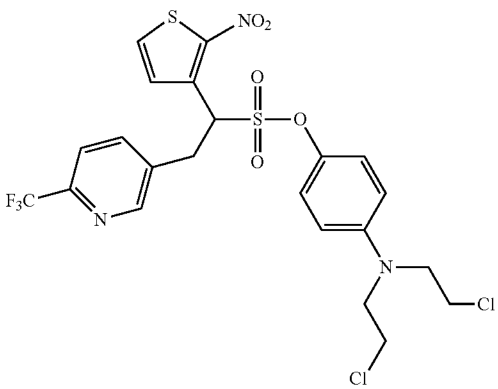 | 300 | 0.4 | 750 | >300 | >300 | |
| 1430 | 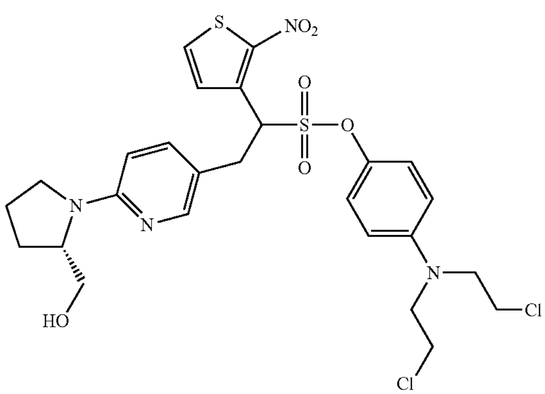 | 300 | 0.6 | 500 | | | |
| 1257 | 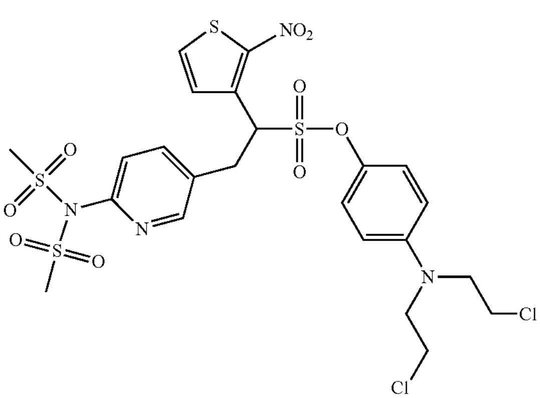 | 212 | 0.5 | 424.0 | >300 | >300 | |

TABLE 2-continued
| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1330 | 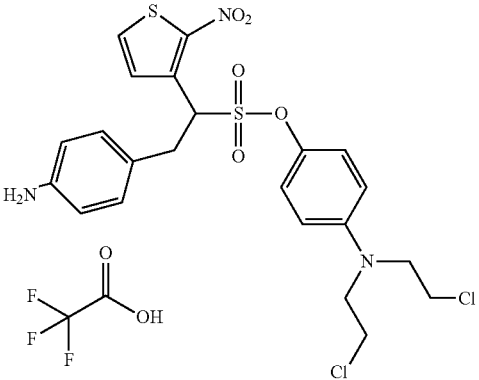 | 227.7 | 0.9 | 253 | 186 | 9 | 21 |
| 1457 | 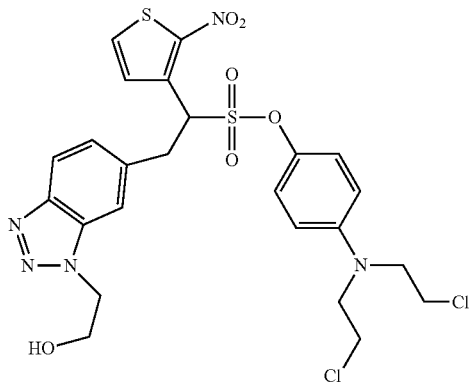 | 120 | 0.5 | 240 | 180 | 4 | 45 |
| 1271 | 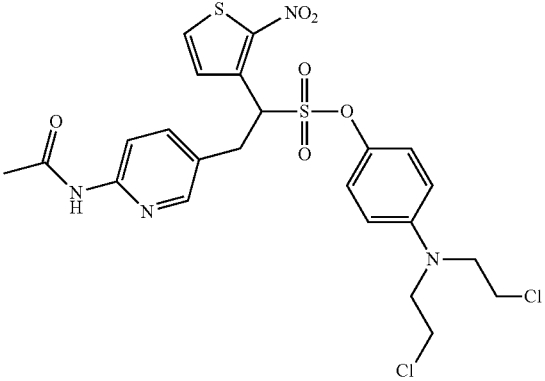 | 236 | 1 | 236 | 977 | 760 | 1.3 |
| 1376 | 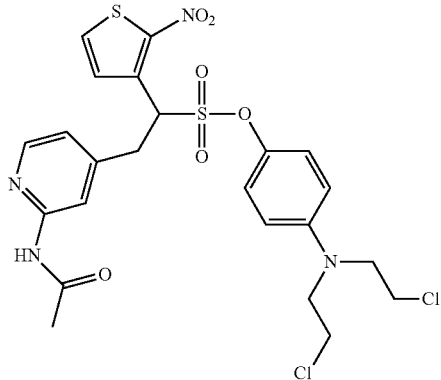 | 212 | 0.9 | 236 | 540 | 52 | 10 |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1278 | 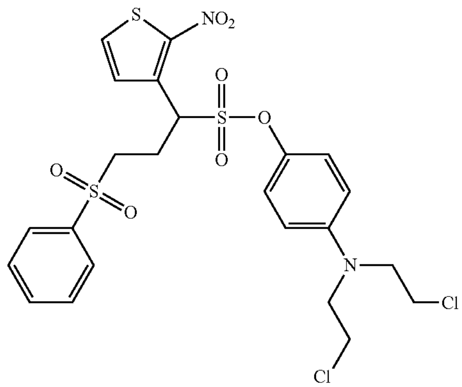 | 61.4 | 0.3 | 205 | >1000 | >1000 | |
| 1346 | 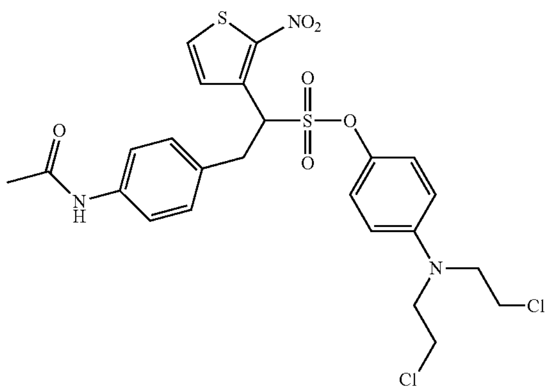 | 220 | 1.1 | 200 | 145 | 46 | 3.2 |
| 1328 | 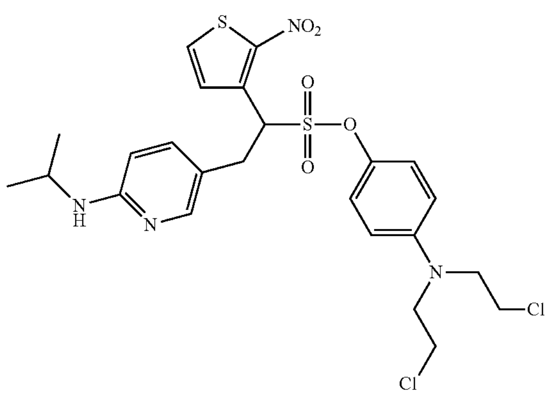 | 261.4 | 1.4 | 187 | 151 | 46 | 3.3 |
| 1266 | 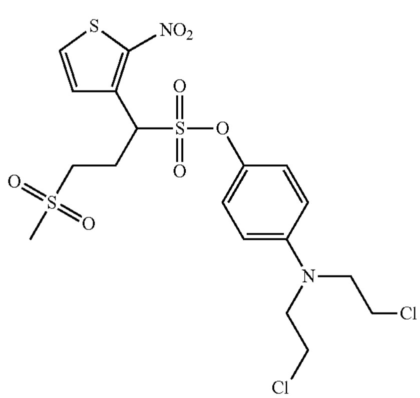 | 55 | 0.3 | 183 | >1000 | 34 | >29 |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1316 | 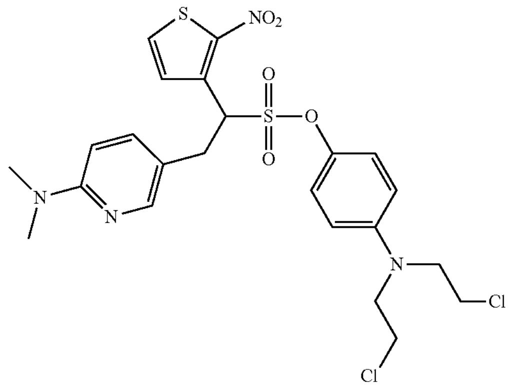 | 178.9 | 1 | 179 | >300 | >300 | |
| 1327 | 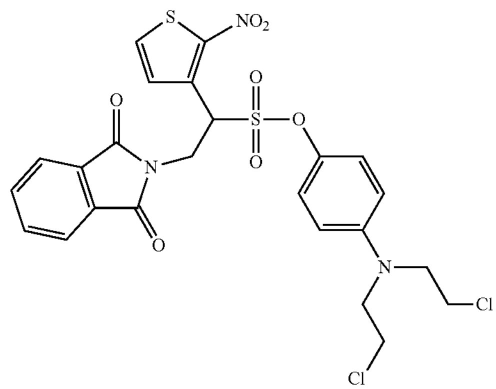 | 106.6 | 0.6 | 178 | >1000 | >1000 | |
| 1262 | 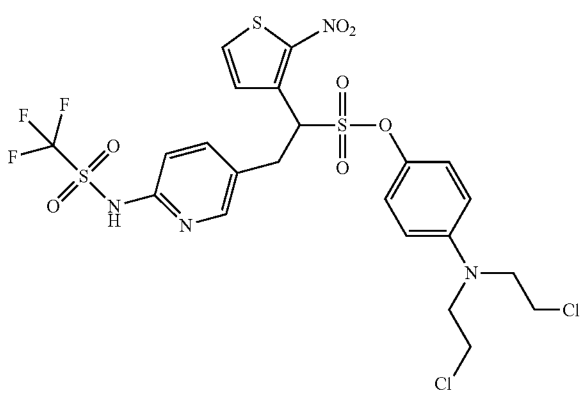 | 90 | 0.6 | 150 | | | |
| 1311 | 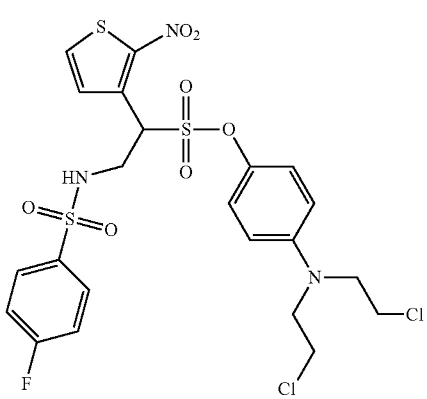 | 57.3 | 0.4 | 143 | >300 | >300 | |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1315 | 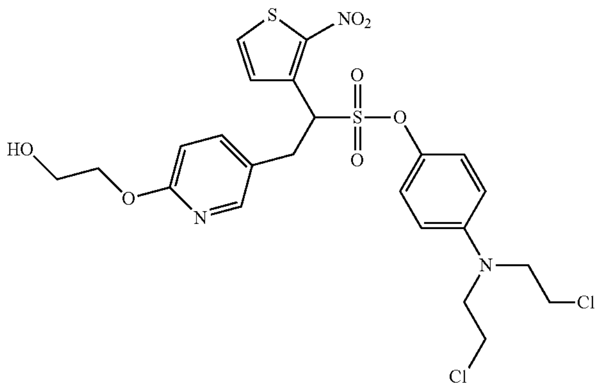 | 99.5 | 0.7 | 142 | >300 | 13 | >23 |
| 1343 | 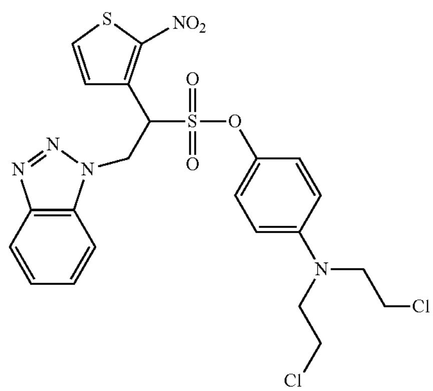 | 93 | 0.7 | 133 | >1000 | 24 | >4.2 |
| 1369 | 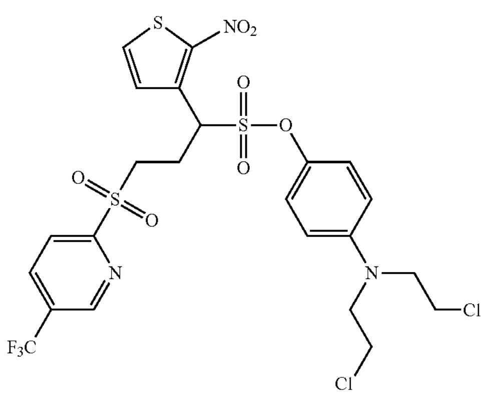 | 236 | 1.8 | 131 | >1000 | >1000 | |
| 1292 | 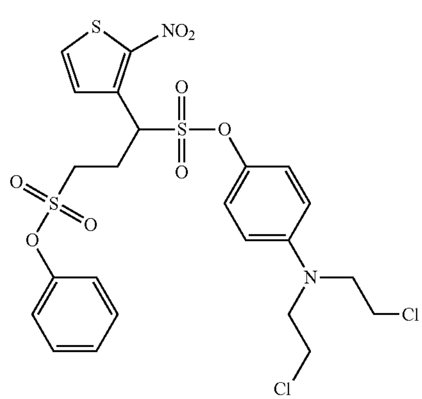 | 195 | 1.5 | 127.7 | 760 | 4.8 | 158 |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1442 | 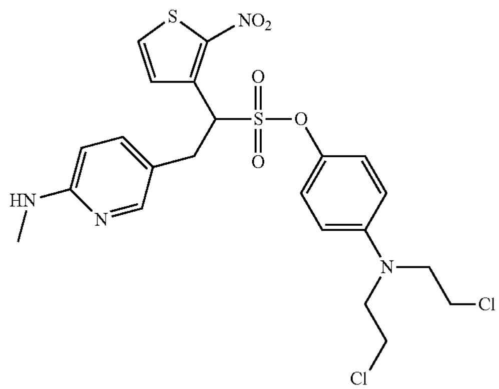 | 93 | 0.8 | 116 | 230 | 3.5 | 66 |
| 1140 | 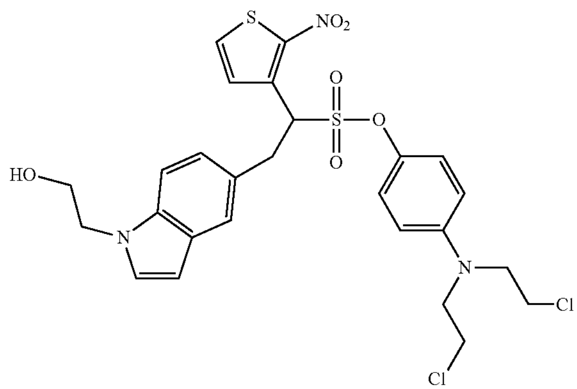 | 114 | 1 | 114 | | | |
| 1363 | 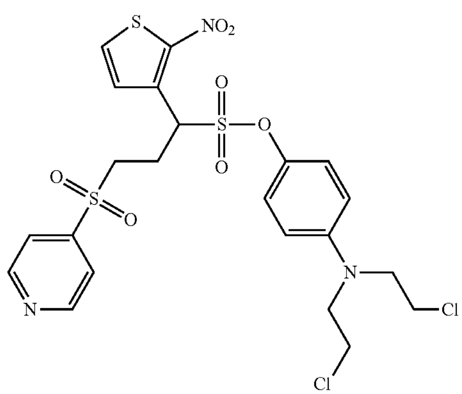 | 68 | 0.6 | 113 | >1000 | >1000 | |
| 1441 | 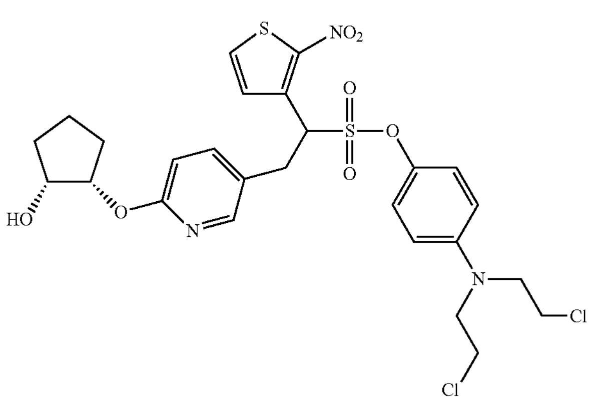 | 190 | 1.7 | 112 | 250 | 28 | 9 |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| | | | | | | | |
| 1451 | 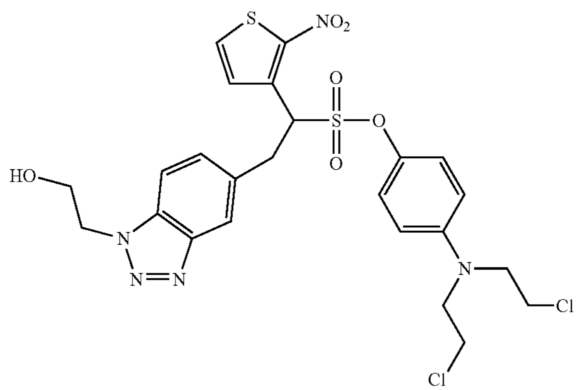 | 110 | 1 | 110 | 250 | 6 | 42 |
| 1218 | 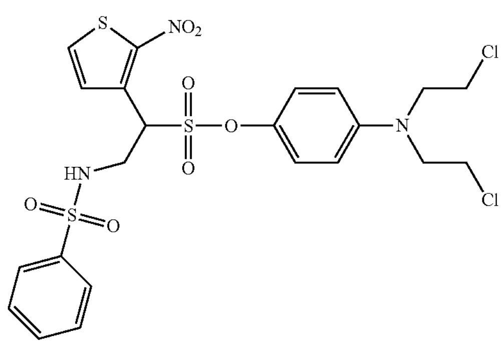 | 74 | 0.7 | 106 | >300 | >300 | |
| 1456 | 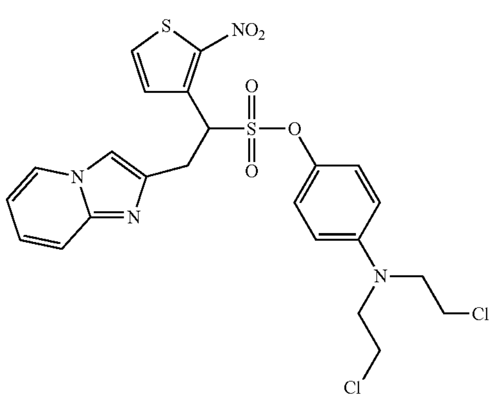 | 30 | 0.3 | 100 | >300 | 5 | >60 |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1375 | 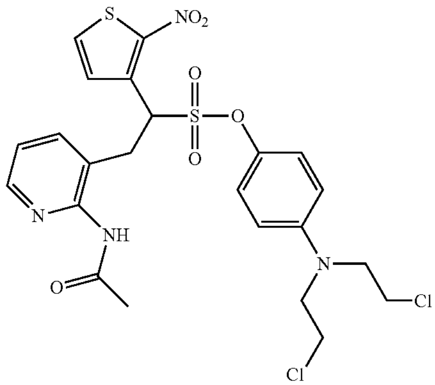 | 28 | 0.3 | 93 | 280 | 17 | 16 |
| 1402 | 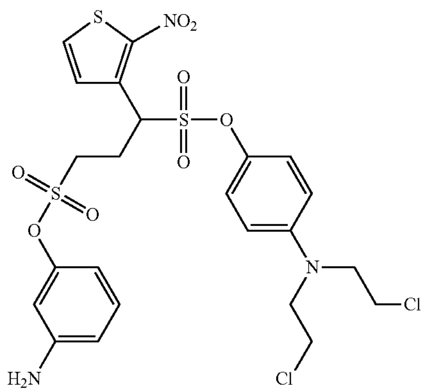 | 140 | 1.5 | 93.3 | >1000 | >1000 | |
| 1272 | 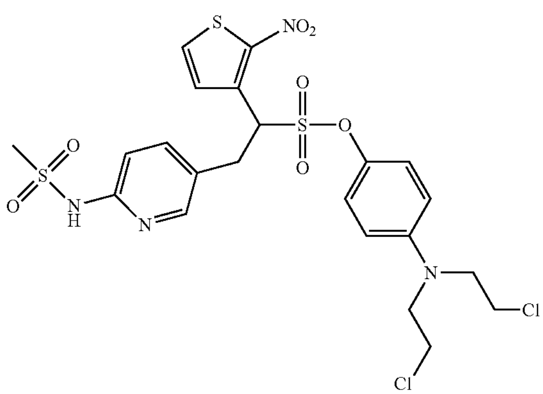 | 290 | 3.2 | 91 | | | |
| 1393 | 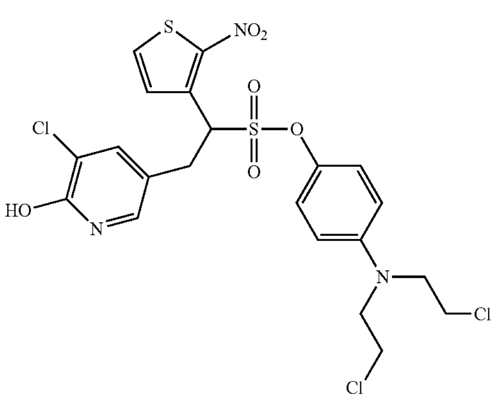 | 151 | 1.7 | 89 | 710 | 110 | |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1422 | 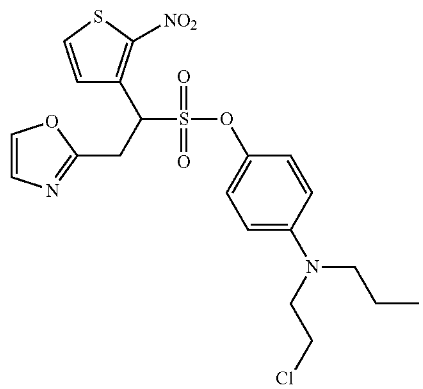 | 35 | 0.4 | 88 | >300 | 90 | >3.3 |
| 1434 | 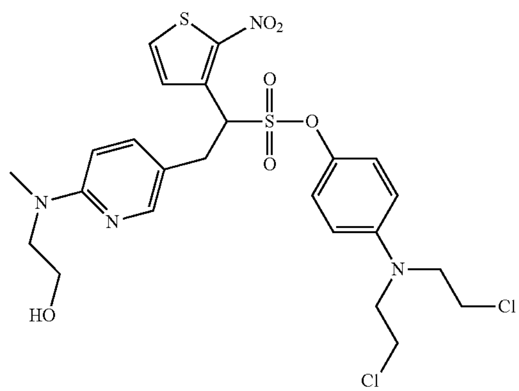 | 50 | 0.6 | 83 | | | |
| 1347 | 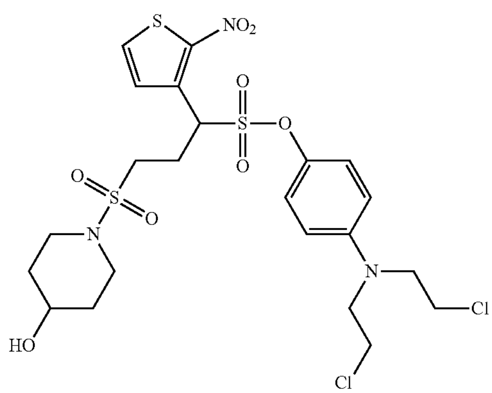 | 136 | 1.8 | 76 | 398 | 20 | 20 |
| 1468 | 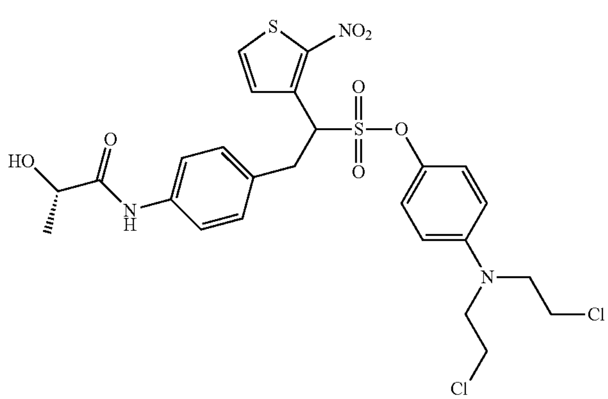 | 30 | 0.4 | 75 | | | |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1374 | (structure) | 145 | 2 | 73 | 630 | 28 | 23 |
| 1331 | (structure) | 103 | 1.5 | 69 | 166 | 11 | 15 |
| 1303 | (structure) | 75.5 | 1.1 | 69 | >300 | >300 | |
| 1305 | (structure) | 47 | 0.7 | 67 | >300 | 6.8 | >44 |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1354 | 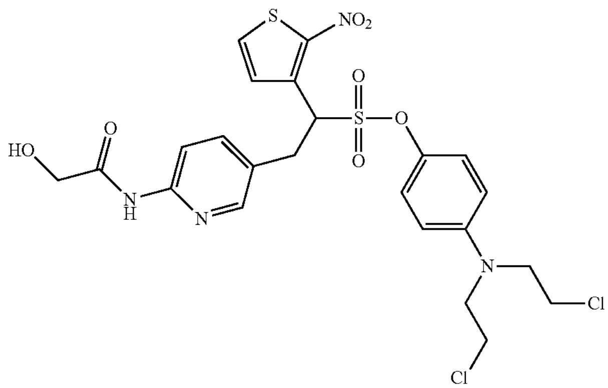 | 156 | 2.4 | 65 | 660 | 20 | 33 |
| 1420 | 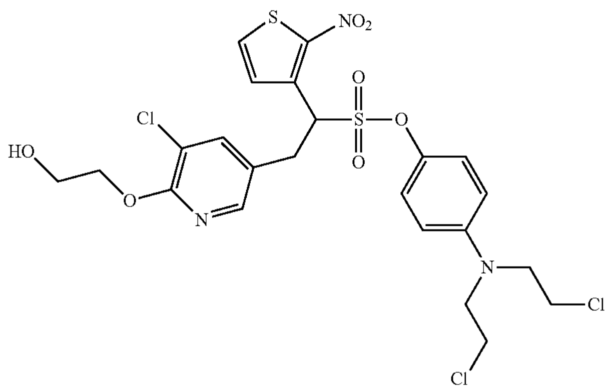 | 80 | 1.3 | 62 | >300 | >300 | |
| 1458 | 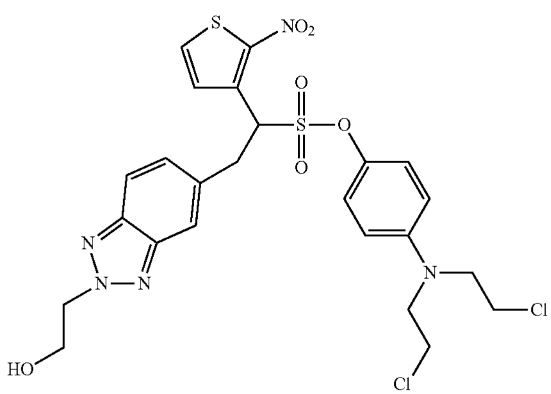 | 30 | 0.5 | 60 | | | |
| 1452 | 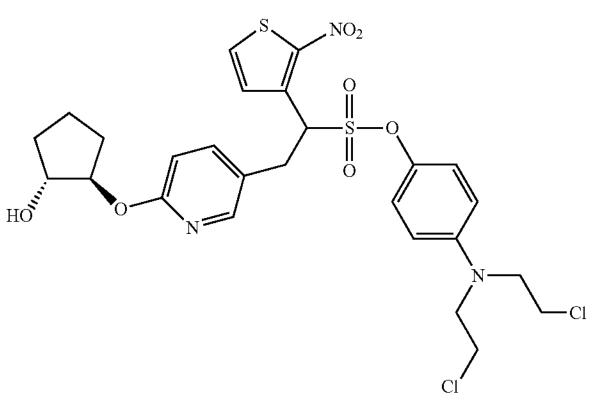 | 110 | 2 | 55 | | | |

TABLE 2-continued

| TH-# | Structure | 2 hr Air H460 IC$_{50}$ µM | 2 hr N$_2$ H460 IC$_{50}$ µM | H460 HCR: Air/N$_2$ | 2 hr Air HT29 IC$_{50}$ µM | 2 hr N$_2$ HT29 IC$_{50}$ µM | HT29 HCR: Air/N$_2$ |
|---|---|---|---|---|---|---|---|
| 1400 | 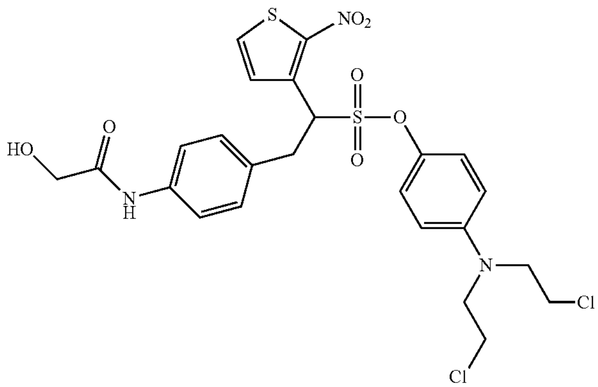 | 76 | 1.4 | 54.3 | 170 | 80 | 2.1 |
| 1414 | 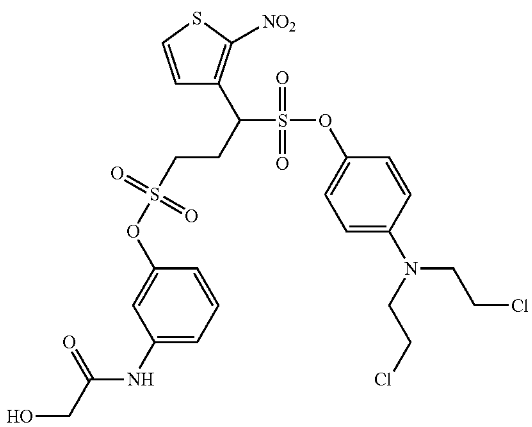 | 135 | 2.5 | 54 | 740 | 100 | 7 |
| 1465 | 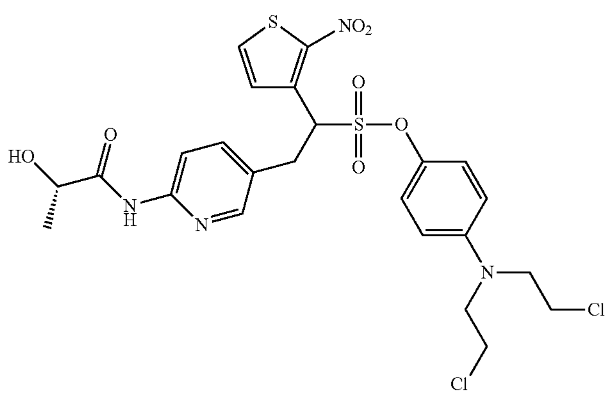 | 40 | 0.8 | 50 | 210 | 7 | 30 |
| 1351 | 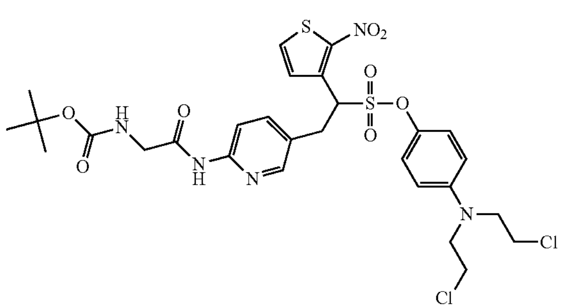 | ~300 | 6.1 | 49 | | | |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1362 | 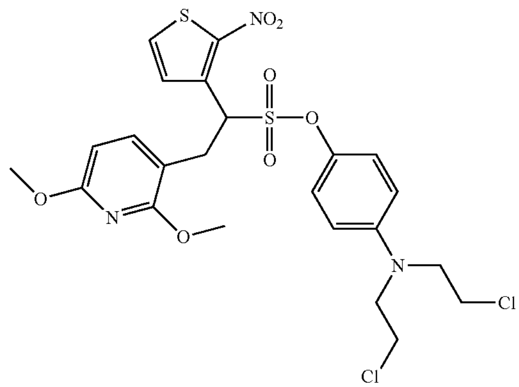 | 253 | 5.5 | 46 | >1000 | >1000 | |
| 1419 | 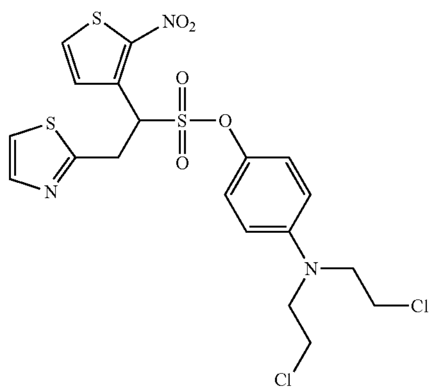 | 36 | 0.8 | 45 | >300 | >300 | |
| 1341 | 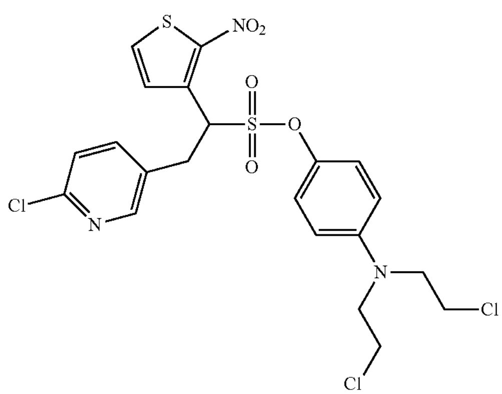 | 145 | 3.4 | 43 | | | |
| 1326 | 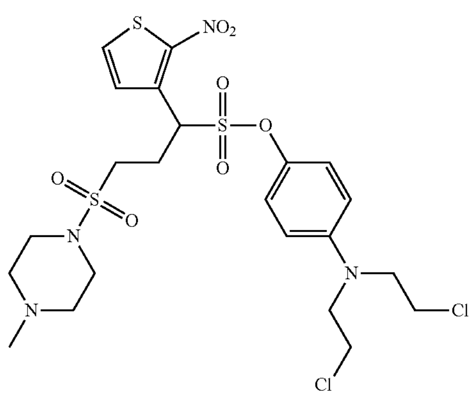 | 16.6 | 0.4 | 42 | 126 | 2.6 | 48 |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1357 | 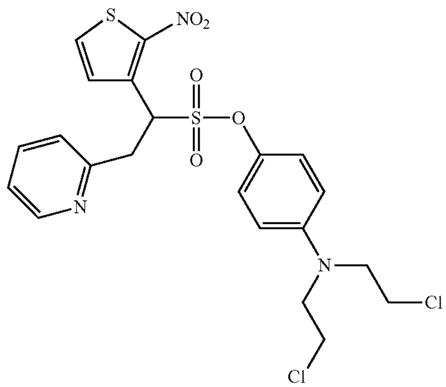 | 127 | 3.1 | 41 | >1000 | 500 | >2 |
| 1366 | 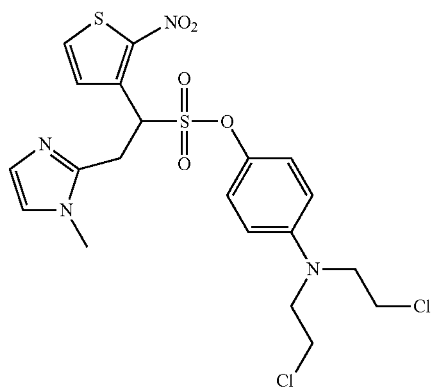 | 20 | 0.5 | 40 | 180 | 13 | 14 |
| 1192 | 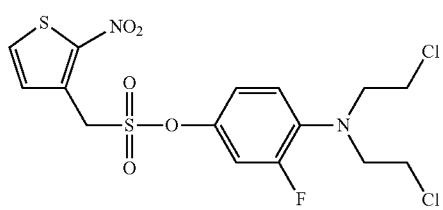 | 59.2 | 1.5 | 39 | 162 | 8 | 20 |
| 1364 | 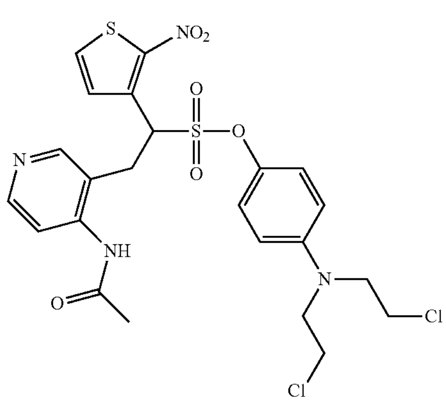 | 64 | 1.8 | 36 | 350 | 13 | 27 |

TABLE 2-continued
| TH-# | Structure | 2 hr Air H460 IC$_{50}$ µM | 2 hr N$_2$ H460 IC$_{50}$ µM | H460 HCR: Air/N$_2$ | 2 hr Air HT29 IC$_{50}$ µM | 2 hr N$_2$ HT29 IC$_{50}$ µM | HT29 HCR: Air/N$_2$ |
|---|---|---|---|---|---|---|---|
| 1388 | 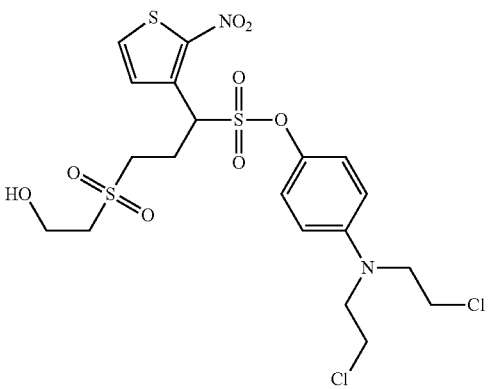 | 49 | 1.4 | 35 | 420 | 14 | 30 |
| 1365 | 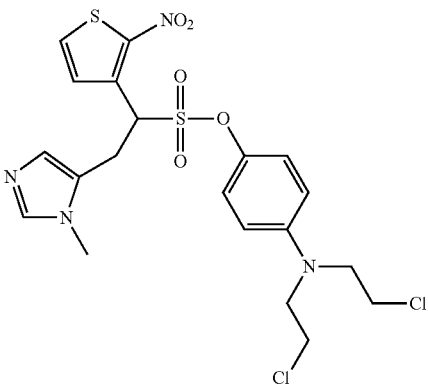 | 23 | 0.7 | 33 | 270 | 11 | 25 |
| 1312 | 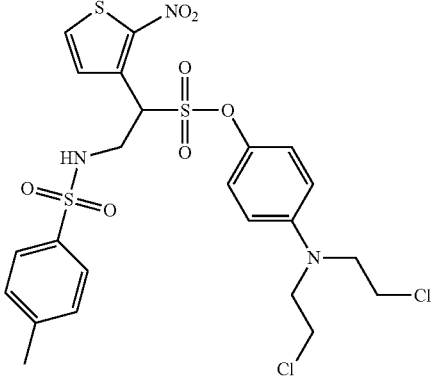 | 122.4 | 3.9 | 31 | | | |
| 1255 | 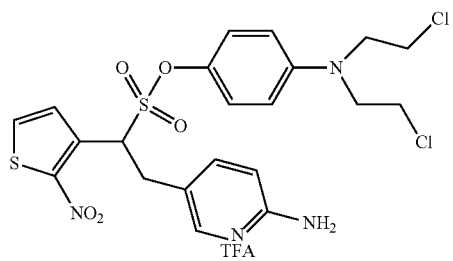 | 61.4 | 2 | 30.7 | 204 | 13 | 16 |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1384 | 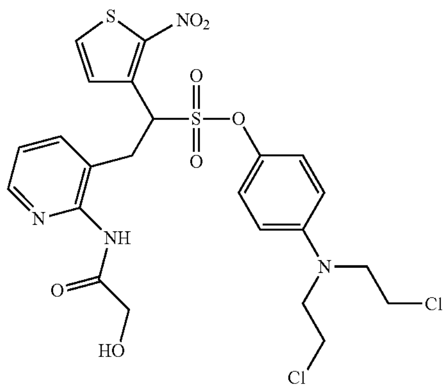 | 64 | 2.1 | 30 | 275 | 17 | 16 |
| 1435 | 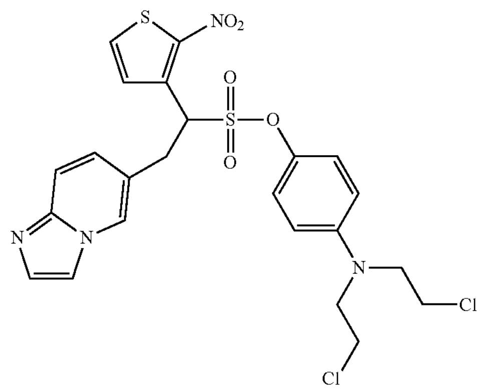 | 18 | 0.6 | 30 | >300 | 8.5 | >35 |
| 1475 | 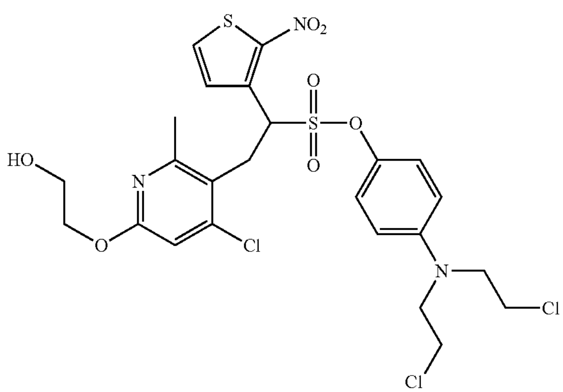 | 100 | 0.6 | 167 | >300 | 18 | >17 |
| 1477 | 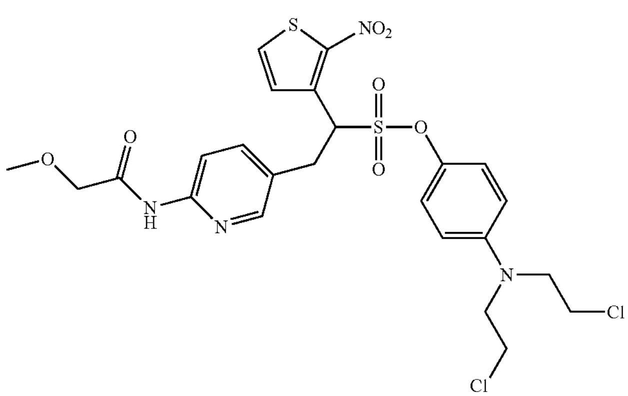 | 13 | 0.3 | 43 | | | |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1478 | 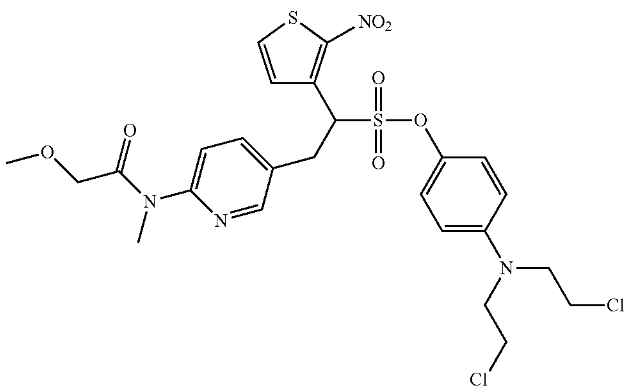 | 120 | 0.4 | 300 | 220 | 20 | 11 |
| 1479 | 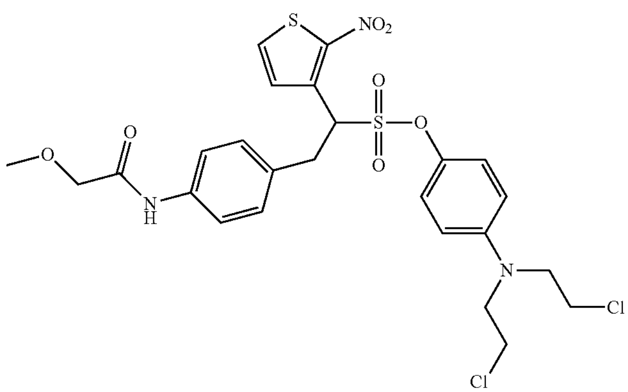 | 260 | 0.8 | 325 | >300 | 110 | 2.7 |
| 1486 | 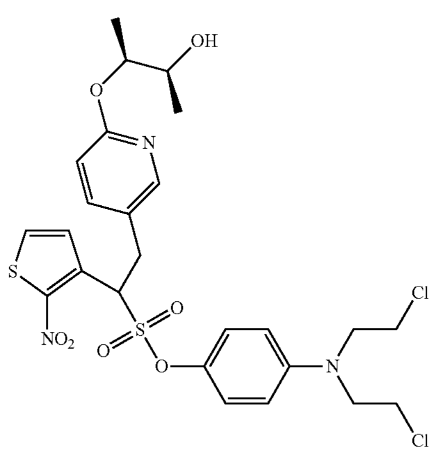 | 36 | 1 | 36 | | | |

TABLE 2-continued

| TH-# | Structure | 2 hr Air H460 IC$_{50}$ μM | 2 hr N$_2$ H460 IC$_{50}$ μM | H460 HCR: Air/N$_2$ | 2 hr Air HT29 IC$_{50}$ μM | 2 hr N$_2$ HT29 IC$_{50}$ μM | HT29 HCR: Air/N$_2$ |
|---|---|---|---|---|---|---|---|
| 1487 | (structure) | 51 | 0.8 | 64 | 240 | 280 | 1 |
| 1521 | (structure) | 234 | 1.3 | 180 | >300 | 93 | >3.2 |
| 1545 | (structure) | 102 | 2 | 51 | 60 | 5 | 12 |

B. Anti Cancer Efficacy of Hypoxia Activated Drug Compounds as Measured in Spheroids Cells were seeded (day 0) on a plate coated with 1% agar and allowed to grow while the media was spun. Spheroids were formed on day 11. Various concentrations (made by serial dilution of a test compound stock solution) of a test compound was added into 24 well plates having glass inserts and containing the spheroids and incubated for 2 h under either air or N$_2$. The spheroids were washed twice with media to remove the test compound and dissociated using trypsin into single cell suspension. The single cell suspensions were counted, plated into a 24 well plate, and incubated for 3 days under air. The fraction of viable cells were determined upon comparison with control group of cells as described in Example 2A. IC$_{50}$ was determined by plotting the viable cells as described in Example 2A. The results, tabulated in Table 1, demonstrate that hypoxia activated drug compounds of the present invention are more effective in killing cancer cells in a spheroid compared to a monolayer.

Without being bound by mechanism, a collection of cells as in a spheroid can effectively represent cancer cells in a solid tumor. Like cells inside a solid tumor, the cells inside the spheroid have lesser access to oxygen and nutrients, and are more difficult to reach for an anti-cancer agent, than the cells on the periphery of the spheroid. As the results demonstrate, the hypoxia activated drug compounds of the present invention can target cells in the interior of a solid tumor as these drug compounds are converted from being a less active drug to a more active cytotoxin under the hypoxia in which the interior cells reside. The compounds of the present invention are capable of reaching the cells in the interior, as opposed to being available to only the cells on or near the outer edge of a solid tumor. Once the drug compounds of the present invention are activated and produce a cytotoxin, the cytotoxin generated can diffuse to cells away from those where they are generated; thus these hypoxia activated drug compounds demonstrate bystander effect. Thus, hypoxia activated drug compounds of the present invention are useful in accordance with the present methods in the treatment of cancer including, but not limited to, solid tumors.

C. In vivo Anti Cancer Efficacy of Hypoxia Activated Drug Compounds of the Present Invention Compounds were tested in a H460 non small cell lung xenograft mouse model. Treatment was initiated when tumors were approximately 100 mm$^3$. Each dose group contained 10 animals. Tumors were measured with calipers throughout the study. The antitumor effect or tumor growth delay was defined as the time in days for the treated tumors to reach 500 mm$^3$ minus the time in days for the vehicle arm to reach 500 mm$^3$. The treatment regimens (with the exception of TH-1405 treatment) involved daily i.p. injections for 5 days, followed by 2 days of rest (drug holiday), followed by 5 more daily i.p. injections. The injection formulation was prepared in 5% DMSO and 5% Tween 80 in sterile water for injection. TH-1405 was freely water soluble and was tested as follows. A pharmaceutical formulation of TH 1405 in saline was administered via i.v. injection on day 1 and day 8.

All compounds demonstrated antitumor efficacy. TH 1266 was tested at the maximum tolerated dose (MTD) of 40 mg/kg and 20 mg/kg and resulted, respectively, in 25 and 21 days of tumor growth delay to 500 mm$^3$. TH-1305 was tested at 20 mg/kg (MTD) and resulted in a tumor growth delay of 10 days. TH-1315 was tested at 50 mg/kg (MTD) and resulted in a 19 day tumor growth delay. TH-1331 was tested at 60 mg/kg (MTD) and 30 mg/kg and resulted in a tumor growth delay of 11 and 10 days respectively. TH-1354 was tested at 40 mg/kg (MTD) and 20 mg/kg and resulted in a tumor growth delay of 15 and 12 days respectively. TH-1365 was tested at 10 mg/kg (MTD) and resulted in a 10 day tumor growth delay. TH-1405 was tested at 25 mg/kg and resulted in a 6 day tumor growth delay. Tumors of vehicle (the formulation excluding the hypoxia activated drug of the present invention, such as for example, saline, or 5% DMSO and 5% Tween 80 in sterile water for injection) treated animal reached 500 mm$^3$ in about 21 days.

Compound TH-1315 was efficacious both as a single agent and in combination with doxorubicin in the HT 1080 sarcoma xenograft mouse model. TH-1315 was dosed at 50 mg/kg as described above. Doxorubicin was dosed i.v. on day one and day 8 at 4 mg/kg (MTD). Antitumor efficacy was assessed via tumor growth delay as described above. TH-1315, doxorubicin and the combination of TH-1315 and doxorubicin showed tumor growth delays of 6, 10 and 21 days, respectively. The tumors of the vehicle treated animals reached 500 mm$^3$, on average, in 14 days.

3. Pharmaceutical Compositions or Formulations of the Hypoxia Activated Drug Compounds The following are representative pharmaceutical compositions or formulations containing a compound of the present invention and pharmaceutically acceptable diluent, excipient, and/or carriers.

Formulation A: Injectable Formulation

The mixture of the following ingredients forms an injectable formulation (q.s.=quantum satis or sufficient amount).

| Ingredient | Amount |
| --- | --- |
| Compound | 100 mg-1000 mg |
| sodium acetate buffer solution, 0.4M | 2.0 mL |
| HCl (1N) or NaOH (1N) | q.s. to suitable pH |
| Sucrose | q.s. |
| water (distilled, sterile) | q.s. to 20 mL |

Formulations B-D, exemplified below, are useful for compounds of the invention that are orally bioavailable Formulation B: Tablet Formulation The following ingredients are mixed intimately and pressed into single scored tablets.

| Ingredient | Quantity per tablet, mg |
| --- | --- |
| Compound | 400 |
| Cornstarch | 50 |
| Croscarmellose sodium | 25 |
| Lactose | 120 |
| Magnesium stearate | 5 |

Formulation C: Capsule Formulation

The following ingredients are mixed intimately and loaded into a hard-shell gelatin capsule.

| Ingredient | Quantity per tablet, mg |
| --- | --- |
| Compound | 200 |
| Lactose, spray-dried | 148 |
| Magnesium stearate | 2 |

Formulation D: Suspension Formulation

The following ingredients are mixed to form a suspension for oral administration (q.s.=quantum satis or sufficient amount).

| Ingredient | Amount |
| --- | --- |
| Compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.0 g |
| Sorbitol (70% solution) | 13.0 g |
| Veegum K (Vanderbilt Co) | 1.0 g |
| Flavoring | 0.035 mL |
| colorings | 0.5 mg |
| distilled water | q.s. to 100 mL |

While this invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

The invention claimed is:

1. A compound having a structure of formula:

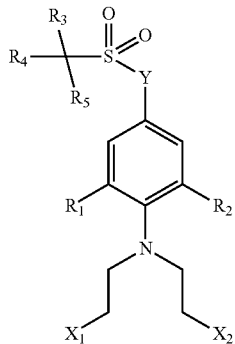

Formula I or a pharmaceutically acceptable salt thereof, wherein each of $X_1$ and $X_2$ is independently selected from the group consisting of chloro, bromo, iodo, and sulfonate;

Y is selected from the group consisting of O and $NR_6$;

each of $R_1$ and $R_2$ is independently selected from the group consisting of hydrogen, halogen, and optionally substituted $C_{1-6}$alkyl;

each of $R_3$ and $R_4$ is independently selected from the group consisting of hydrogen and optionally substituted $C_{1-6}$alkyl;

$R_5$ is a bioreductive group selected from the group consisting of:

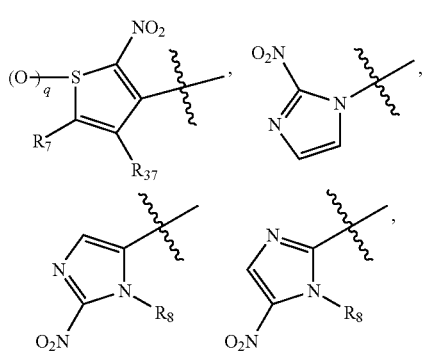

-continued

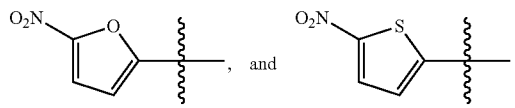

$R_6$ is selected from the group consisting of hydrogen and optionally substituted $C_{1-6}$alkyl;

$R_7$ is selected from the group consisting of hydrogen and optionally substituted $C_{1-6}$alkyl;

$R_{37}$ is hydrogen, or together with $R_7$ and the carbon atoms to which they are bonded, form an optionally substituted cycloalkyl, optionally substituted heterocyclyl, optionally substituted aryl, or optionally substituted heteroaryl moiety;

$R_8$ is optionally substituted $C_{1-6}$alkyl; and q is 0, 1, or 2.

2. The compound of claim 1 having the structure of formula:

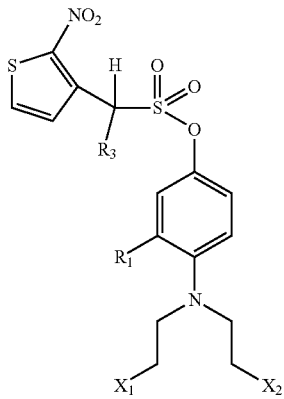

wherein each $X_1$ and $X_2$ independently is selected from the group consisting of chloro, bromo, and sulfonate;

$R_1$ is selected from the group consisting of hydrogen and fluoro;

$R_3$ is selected from the group consisting of hydrogen and an optionally substituted alkyl moiety having a structure of formula -L-$P_1$—$R_{20}$;

L is optionally substituted $C_{1-4}$alkylene;

$P_1$ is selected from the group consisting of a bond, —S(=O)$_2$—, and —NR$_{21}$(S=O)$_2$—;

$R_{20}$ is selected from the group consisting of an optionally substituted $C_{1-4}$alkyl; optionally substituted $C_{2-4}$alkynyl; an aryl substituted with a substituent selected from the group consisting of amino, substituted amino, and acylamino; aryloxy; cycloalkyloxy; an optionally substituted heteroaryl moiety containing a basic nitrogen atom that is either part of the heteroaryl ring or is a heteroaryl ring substituent; and an optionally substituted heterocycle containing up to 2 nitrogen atoms; and $R_{21}$ is selected from the group consisting of hydrogen and optionally substituted $C_{1-4}$alkyl.

3. The compound of claim 1 having the structure of formula:

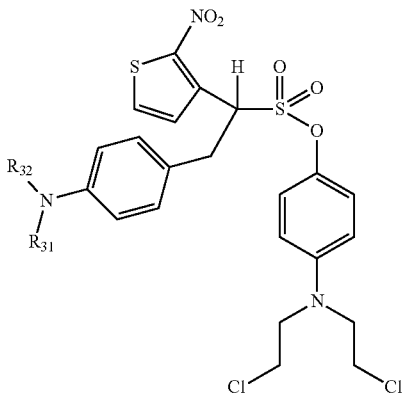

wherein each of $R_{31}$ and $R_{32}$ is independently selected from the group consisting of hydrogen, optionally substituted alkyl, and —C(=O)—CR$_{33}$(R$_{34}$)(R$_{35}$); $R_{33}$ is amino; $R_{34}$ is selected from the group consisting of hydrogen and optionally substituted $C_{1-4}$alkyl; and $R_{35}$ is $C_{1-6}$alkyl optionally substituted with a substituent selected from the group consisting of optionally substituted amino and optionally substituted guanidino.

4. The compound of claim 1 having the structure of formula:

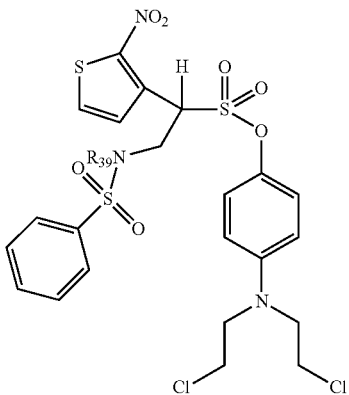

wherein $R_{39}$ is hydrogen or optionally substituted $C_{1-4}$alkyl.

5. The compound of claim 1 having the structure of formula:

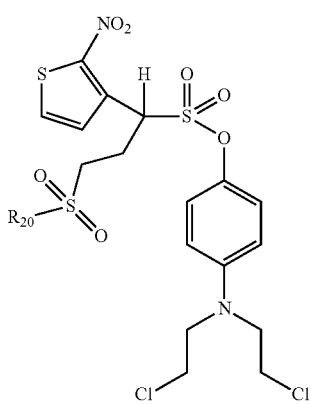

wherein $R_{20}$ is selected from the group consisting of $C_{1-4}$alkyl optionally substituted with up to 2 hydroxy groups, an optionally substituted aryloxy, optionally substituted heteroaryloxy, and a nitrogen containing heterocycle wherein the point of attachment of said heterocycle to the $SO_2$ moiety is through a nitrogen atom.

6. The compound of claim 2, wherein $R_1$ is hydrogen and L is selected from the group consisting of —CH$_2$— and —CH$_2$—CH$_2$—.

7. The compound of claim 2, wherein $R_1$ is fluoro.

8. The compound of claim 7, wherein $R_3$ is hydrogen.

9. The compound of claim 6, wherein $P_1$ is a bond, L is —CH$_2$—, and $R_{20}$ is an optionally substituted heteroaryl moiety containing a basic nitrogen atom selected from the group consisting of benzotriazolyl, imidazopyridyl, imidazolyl, and pyridyl.

10. The compound of claim 9 having the structure of formula:

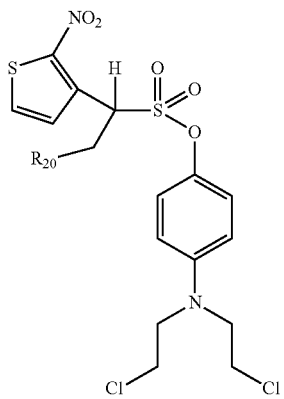

wherein $R_{20}$ is substituted pyridyl having the structure of formula:

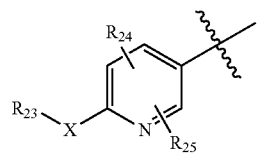

$R_{23}$ is selected from the group consisting of hydrogen, $C_{1-4}$alkyl optionally substituted with up to 2 hydroxy groups, and —(C=O)CR$_{27}$(R$_{28}$)(R$_{29}$);

$R_{24}$ is selected from the group consisting of hydrogen and optionally substituted $C_{1-4}$alkyl;

$R_{25}$ is selected from the group consisting of hydrogen and halogen;

X is selected from the group consisting of NR$_{26}$, O, and a bond;

each of $R_{26}$, $R_{27}$, and $R_{28}$ independently is selected from the group consisting of hydrogen and optionally substituted $C_{1-4}$alkyl; and $R_{29}$ is selected from the group consisting of hydroxyl, optionally substituted alkoxy, and optionally substituted $C_{1-4}$alkyl with the proviso that when X is a bond, $R_{23}$ is hydrogen and with the proviso that when X is O, $R_{23}$ excludes —(C=O)CR$_{27}$(R$_{28}$)(R$_{29}$).

11. The compound of claim 9 having the structure of formula:

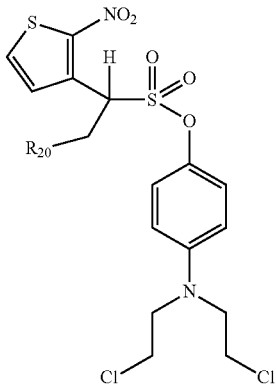

wherein $R_{20}$ is selected from the group consisting of:

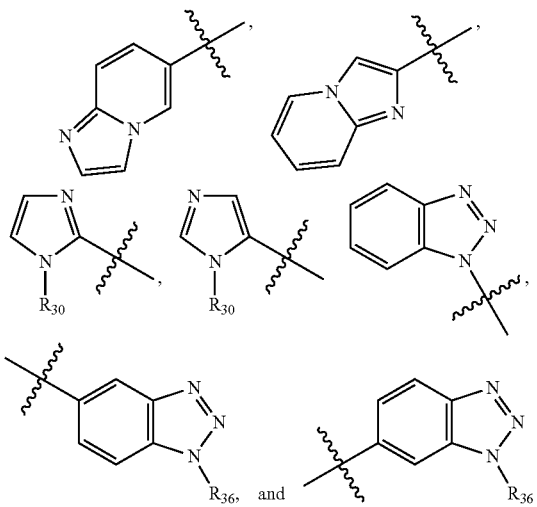

wherein $R_{30}$ is optionally substituted $C_{1-4}$alkyl and $R_{36}$ is $C_{1-4}$alkyl optionally substituted with up to 2 hydroxy groups.

12. The compound of claim 5, wherein $R_{20}$ is a piperazinyl moiety having the structure of formula:

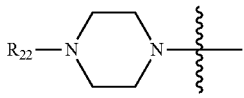

wherein $R_{22}$ is $C_{1-4}$alkyl.

13. The compound of claim 10, wherein $R_{27}$ and $R_{28}$ is methyl and $R_{29}$ is hydroxy.

14. The compound of claim 10, wherein X is O.

15. The compound of claim 1 selected from the group consisting of:
- 3-(4-(N,N-bis-(2-Chloroethyl)amino)phenoxysulfonyl-(2-methylsulfonyl)ethyl)methyl-2-nitrothiophene;
- 3-(4-(N,N-bis-(2-Chloroethyl)amino)phenoxysulfonyl-(2-(2-hydroxyethoxy)pyridin-5-yl-methyl))methyl-2-nitrothiophene;
- 3-(4-(N,N-bis-(2-Chloroethyl)amino)phenoxysulfonyl-(benzotriazol-1-yl-methyl))methyl-2-nitrothiophene;
- 3-(4-(N,N-bis-(2-Chloroethyl)amino)phenoxysulfonyl-(4-aminophenylmethyl))methyl-2-nitrothiophene (trifluoroacetate salt);
- 3-(4-(N,N-bis-(2-Chloroethyl)amino)phenoxysulfonyl-(1-(2-hydroxyethyl)benzotriazol-6-yl-methyl))methyl-2-nitrothiophene;
- 3-(4-(N,N-bis-(2-Chloroethyl)amino)phenoxysulfonyl-(2-phenoxysulfonylethyl))methyl-2-nitrothiophene;
- 3-(4-(N,N-bis-(2-Chloroethyl)amino)phenoxysulfonyl-((2-methylamino)pyridin-5-yl)methyl))methyl-2-nitrothiophene;
- 3-(4-(N,N-bis-(2-Chloroethyl)amino)phenoxysulfonyl-(1-(2-hydroxyethyl)benzotriazol-5-yl-methyl))methyl-2-nitrothiophene;
- 3-(4-(N,N-bis-(2-Chloroethyl)amino)phenoxysulfonyl-(phenylsulfonylaminomethyl))methyl-2-nitrothiophene;
- 3-(4-(N,N-bis-(2-Chloroethyl)amino)phenoxysulfonyl-(imidazopyridin-2-yl-methyl))methyl-2-nitrothiophene;
- 3-(4-(N,N-bis-(2-Chloroethyl)amino)phenoxysulfonyl-(pyridin-3-yl-methyl))methyl-2-nitrothiophene;
- 3-(4-(N,N-bis-(2-Chloroethyl)amino)phenoxysulfonyl-(2-hydroxypyridin-5-yl-methyl))methyl-2-nitrothiophene;
- 3-(4-(N,N-bis-(2-Chloroethyl)amino)phenoxysulfonyl-(2-(hydroxyacetylamino)pyridin-5-yl-methyl))methyl-2-nitrothiophene;
- 3-(4-(N,N-bis-(2-Chloroethyl)amino)phenoxysulfonyl-(2-(lactic acylamino)pyridine-5-yl-methyl))methyl-2-nitrothiophene;
- 3-(4-(N,N-bis-(2-Chloroethyl)amino)phenoxysulfonyl-(2-((N-methylpiperazin-4-yl)sulfonyl)ethyl))methyl-2-nitrothiophene;
- 3-(4-(N,N-bis-(2-Chloroethyl)amino)phenoxysulfonyl-(N-methylimidazol-2-yl-methyl))methyl-2-nitrothiophene;
- 3-((3-Fluoro-4-(N,N-bis-(2-chloroethyl)amino)phenoxy)sulfonyl)methyl-2-nitrothiophene;
- 3-(4-(N,N-bis-(2-Chloroethyl)amino)phenoxysulfonyl-(2-(2-hydroxyethylsulfonyl)ethyl))methyl-2-nitrothiophene;
- 3-(4-(N,N-bis-(2-Chloroethyl)amino)phenoxysulfonyl-(N-methylimidazol-5-yl-methyl))-2-nitrothiophene;
- 3-(4-(N,N-bis-(2-Chloroethyl)amino)phenoxysulfonyl-(2-aminopyridin-5-yl-methyl))methyl-2-nitrothiophene trifluoroacetate;
- 3-(4-(N,N-bis-(2-Chloroethyl)amino)phenoxysulfonyl-(imidazopyidin-5-yl-methyl))methyl-2-nitrothiophene;
- 3-(4-(N,N-bis-(2-Chloroethyl)amino)phenoxysulfonyl-(2-(2-hydroxyethoxy)-4-chloro-6-methylpyridin-5-yl-methyl))methyl-2-nitrothiophene;
- 3-(4-(N,N-bis-(2-Chloroethyl)amino)phenoxysulfonyl-(2-(N-methoxyacetyl-N-methylamino)pyridin-5-yl-methyl))methyl-2-nitrothiophene;
- 3-(4-(N,N-bis-(2-Chloroethyl)amino)phenoxysulfonyl-(2-(lysylamino)pyridine-5-yl-methyl))methyl-2-nitrothiophene (dihydrochloride salt); and
- 3-(4-(N,N-bis-(2-Chloroethyl)amino)phenoxysulfonyl-(2-chloro-4-aminophenylmethyl))methyl-2-nitrothiophene (trifluoroacetate salt).

16. A pharmaceutical formulation comprising the compound of any one of claims 1 and 15 and a pharmaceutically acceptable carrier, excipient, or diluent.

17. A method of treating cancer comprising administering a therapeutically effective amount of the compound of any one of claims 1 and 15 to a patient in need of such treatment, wherein the cancer is lung cancer, colon cancer, or fibrosarcoma.

* * * * *